United States Patent
Prichard et al.

(10) Patent No.: US 11,414,703 B2
(45) Date of Patent: *Aug. 16, 2022

(54) **MARKERS TO PREDICT MACROCYCLIC LACTONE DRUG RESISTANCE IN *DIROFILARIA IMMITIS*, THE CAUSATIVE AGENT OF HEARTWORM DISEASE**

(71) Applicants: Elanco US Inc., Indianapolis, IN (US); McGill University, Montreal (CA)

(72) Inventors: Roger K. Prichard, Quebec (CA); Catherine Bourguinat, Quebec (CA); Timothy G. Geary, Quebec (CA)

(73) Assignees: Elanco US Inc., Greenfield, IN (US); McGill University

( * ) Notice: Subject to any disclaimer, the term of this patent is extended or adjusted under 35 U.S.C. 154(b) by 0 days.

This patent is subject to a terminal disclaimer.

(21) Appl. No.: 15/887,164

(22) Filed: Feb. 2, 2018

(65) Prior Publication Data
US 2018/0187264 A1 Jul. 5, 2018

Related U.S. Application Data

(63) Continuation of application No. 14/896,736, filed as application No. PCT/US2014/044000 on Jun. 25, 2014, now Pat. No. 10,000,811.

(60) Provisional application No. 61/839,545, filed on Jun. 26, 2013.

(51) Int. Cl.
*C12Q 1/68* (2018.01)
*C07H 21/04* (2006.01)
*C12Q 1/6883* (2018.01)
*C12Q 1/6888* (2018.01)

(52) U.S. Cl.
CPC ......... *C12Q 1/6883* (2013.01); *C12Q 1/6888* (2013.01); *C12Q 2600/124* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | | | |
|---|---|---|---|---|
| 5,474,796 A | * | 12/1995 | Brennan | B01J 19/0046 422/547 |
| 7,250,496 B2 | * | 7/2007 | Bentwich | G16B 15/10 536/23.1 |
| H2220 H | * | 7/2008 | Wang | 536/23.1 |
| 10,000,811 B2 | * | 6/2018 | Prichard | C12Q 1/6888 |

FOREIGN PATENT DOCUMENTS

| | | | |
|---|---|---|---|
| WO | WO-2008137089 A2 | * 11/2008 | ........... C12Q 1/6886 |
| WO | WO/2011/120165 A1 | 10/2011 | |
| WO | 2013017367 A1 | 11/2013 | |

OTHER PUBLICATIONS

Godel et al. (FASEB, vol. 26, No. 11, pp. 4650-4661, Aug. 15, 2012). (Year: 2012).*
NEB catalog (1998/1999), pp. 121, 284 (Year: 1998).*
Rothstein et al. (1994) PNAS USA 91: 4155-4159 (Year: 1994).*
Stragene (1998). (Year: 1998).*
Bourguinat, Catherine, et al. "Correlation between loss of efficacy of macrocyclic lactone heartworm anthelmintics and P-glycoprotein genotype." Veterinary parasitology 176.4 (2011): 374-381.
Godel, Christelle, et al. "The genome of the heartworm, *Dirofilaria immitis*, reveals drug and vaccine targets." The FASEB Journal 26.11 (2012): 4650-4661.
Anonymous: "The genome of the heartworm, *Dirofilaria immitis*," (Aug. 6, 2012) Retrieved from the internet: http://nematodes.org/genomes/dirofilaria_immitis/ on Oct. 30, 2014.
Anonymous: "Blastn" (Oct. 30, 2014), XP05515004, Retrieved from the internet: http://xyala.cap.ed.ac.uk/tmp/blast/102371414680881.blastn.htm on Oct. 30, 2014. Sequence alignment with nDi.2.2.scaf00021.
Anonymous: "Safety Data Sheet—Random Hexamer Primers" (Apr. 23, 2012), XP055150159, Retrieved from the internet: https://ools.lifetechnologies.com/content/sfs/msds/2012/N8080127_MTR-EULT_BE.pdf on Oct. 31, 2014.
Database EMBL (online): "PV_GBa0077F16.r V_GBa Phaseolus vulgaris genomic clone PV_GBa0077F16 3', genomic survey sequence.", XP002731895, retrieved from EBI accession No. EM_GS-S:EI469912, Database accession No. EI469912 sequence, Mar. 29, 2007.
Database GenBank (online): "Dirofilaria immitis WGS project CAWD000000000 data, contig 000021_632,-Nucleotide—NCBI", XP002731896, retrieved from NCBI accession No. CAWD010000632.1, nucleotides 2461 to 2162, Aug. 20, 2013.
Godel et al. (FASEB, vol. 26, No. 11, pp. 4650-4661, Aug. 15, 2012).

\* cited by examiner

*Primary Examiner* — Jeanine A Goldberg
(74) *Attorney, Agent, or Firm* — Hoffmann & Baron, LLP

(57) ABSTRACT

Disclosed are nucleic acid molecules from the genome of *Dirofilaria* spp. nematodes that contain single nucleotide polymorphisms related to reduced responsiveness of the nematodes to macrocyclic lactones. In one example, the species of *Dirofilaria* is *Dirofilaria immitis* (the agent of heartworm in animals). Also disclosed are methods for determining the responsiveness of *Dirofilaria* spp. nematodes to macrocyclic lactones, methods for selecting a treatment to treat an animal infected with a *Dirofilaria* spp. nematode, and kits for determining the responsiveness of *Dirofilaria* spp. nematodes to macrocyclic lactones.

11 Claims, 29 Drawing Sheets
Specification includes a Sequence Listing.

Table 1. Genotype frequencies for markers representing SEQ ID NOs: 110-127

| SNP Loci | % Genotype Frequency Susceptible | | | % Genotype Frequency Confirmed Resistant | | | Comparison Susceptible/Confirmed Resistant p-value | % Genotype Frequency Confirmed Resistant + LOE | | | Comparison Susceptible/Confirmed Resistant + LOE p-value |
|---|---|---|---|---|---|---|---|---|---|---|---|
| | CC | CT | TT | CC | CT | TT | | CC | CT | TT | |
| MARKER_31307* | | | 100.0% | 2.9% | 11.7% | 85.4% | 6.3E-05 | 8.7% | 8.7% | 82.6% | 5.7E-06 |
| MARKER_26225* | | 0.7% | 99.3% | 1.3% | 48.3% | 50.3% | 3.7E-21 | 1.9% | 47.2% | 50.9% | 1.2E-23 |
| MARKER_47722_B* | 6.5% | 1.3% | 92.3% | 22.7% | 33.7% | 43.6% | 5.0E-20 | 18.9% | 23.5% | 57.6% | 2.9E-14 |
| MARKER_58162_B | 0.7% | 1.5% | 97.8% | 26.7% | 18.6% | 54.7% | 1.8E-16 | 30.7% | 14.7% | 54.6% | 1.0E-18 |
| | AA | AG | GG | AA | AG | GG | | AA | AG | GG | |
| MARKER_17709* | 100.0% | | | 74.1% | 19.0% | 6.8% | 4.3E-02 | 67.3% | 17.5% | 15.1% | NS |
| MARKER_47141* | 100.0% | | | 56.7% | 43.3% | | 4.7E-23 | 68.8% | 27.7% | 3.5% | 3.5E-16 |
| MARKER_48750_A | 100.0% | | | 54.9% | 28.7% | 16.5% | 1.3E-15 | 54.1% | 24.8% | 21.0% | 1.9E-17 |
| MARKER_63962 | 100.0% | | | 87.7% | 11.7% | 0.6% | 1.0E-03 | 81.9% | 11.8% | 6.2% | 1.7E-05 |
| MARKER_6372 | 90.2% | 2.3% | 7.5% | 20.2% | 49.7% | 30.1% | 1.8E-32 | 35.8% | 32.9% | 31.3% | 2.0E-26 |
| MARKER_15611* | 90.5% | | 9.5% | 53.3% | 26.7% | 20.0% | 9.3E-14 | 47.7% | 15.9% | 36.4% | 6.9E-19 |
| | AA | AT | TT | AA | AT | TT | | AA | AT | TT | |
| MARKER_46432 | | | 100.0% | 0.8% | 15.0% | 84.2% | 8.2E-05 | 3.2% | 10.3% | 86.5% | 3.0E-04 |
| MARKER_29594 | 1.2% | 8.7% | 90.1% | 12.7% | 32.9% | 54.4% | 1.5E-12 | 12.4% | 20.8% | 66.8% | 1.4E-08 |
| | CC | CG | GG | CC | CG | GG | | CC | CG | GG | |
| MARKER_26784 | | | 100.0% | 16.8% | 7.2% | 76.0% | 1.4E-07 | 10.1% | 4.4% | 85.4% | 1.0E-04 |
| MARKER_51661 | 100.0% | | | 45.5% | 39.4% | 15.2% | 2.7E-23 | 48.9% | 29.0% | 22.1% | 2.7E-24 |
| MARKER_7819* | 94.9% | 1.9% | 3.2% | 45.2% | 39.2% | 15.7% | 3.1E-21 | 53.6% | 23.5% | 23.0% | 3.1E-19 |
| MARKER_26704* | 90.4% | 4.5% | 5.1% | 70.2% | 27.4% | 2.4% | 2.5E-08 | 65.8% | 22.7% | 11.5% | 2.2E-09 |
| | AA | AC | CC | AA | AC | CC | | AA | AC | CC | |
| MARKER_14329 | 1.1% | 6.1% | 92.8% | 6.4% | 14.0% | 79.7% | 9.9E-04 | 17.4% | 20.4% | 62.2% | 1.0E-13 |
| | GG | GT | TT | GG | GT | TT | | GG | GT | TT | |
| MARKER_56169 | | | 100.0% | 16.0% | 1.3% | 82.7% | 5.0E-03 | 21.8% | 1.1% | 77.1% | 4.8E-04 |

*For markers designated with an asterisk (*), the genotype indicated shows analysis of the reverse complement of the sequences shown as SEQ ID NOs: 110-127.

Figure 29

SEQUENCE LISTING

```
<160> NUMBER OF SEQ ID NOS: 127

<210> SEQ ID NO 1
<211> LENGTH: 300
<212> TYPE: DNA
<213> ORGANISM: Dirofilaria immitis

<400> SEQUENCE: 1
aacataaaca tattgaactg aatcctgcaa acagttctct tataacgtga accataacta      60
aatttagaga aaatatgaaa aagaaaaata agttgctttt gctcgtgcac caactctaat     120
acccaggaaa tcaagaagtg ataatgagta atgtcatcat tagattcagt aattggtgac     180
actatcaata ttattattat tatacttaaa aatacgacga ccacttatcg taacttaaag     240
```
catgcataat acgactgtca tcatattaca tttcttcaag ttcgtattgg acaagtgatt     300

<210> SEQ ID NO 2
<211> LENGTH: 300
<212> TYPE: DNA
<213> ORGANISM: Dirofilaria immitis

<400> SEQUENCE: 2
gacaagcgtt gacgggagag acgatataat aataaagaag gcattgggta tcagaaggca     60
caatccaatt ataaatgcca aggcaaaatg aataaaattt atgctgacga tttgatcaat    120
tacgaagaat ttccgatcgg ctcgaatctt tgtttgtatg tgcactactg ttaacttaat    180
ctttgtttta tactttttg cgtgtcatat ataatatatt catgtcaact gatacgttat     240
gatgtttttt tgtaaattaa gttgatcgga aacctgaagt ctatttcaaa tttaagaaat    300

<210> SEQ ID NO 3
<211> LENGTH: 300
<212> TYPE: DNA
<213> ORGANISM: Dirofilaria immitis

<400> SEQUENCE: 3
ttttaggaaa atggtgactg tagagagata ttatcggaac gacaaggtcc acttcgaacg     60
ggtcttttat tgtcgacgga ttgtgaacca agttttggca ttcataatga caggtagcta    120
tttttccatc atcccatttt tgtattagtg caagcaagtc atgagtcgaa agaaaatctc    180
aaaagaaaaa aatgaaattt caggttcaaa ggactgcgtc cattattcgc actggttgat    240
gagaacgtac agattccaga gcggcaatgc tgcacagtat cttttgtttc acttctgaat    300

<210> SEQ ID NO 4
<211> LENGTH: 300
<212> TYPE: DNA
<213> ORGANISM: Dirofilaria immitis

<400> SEQUENCE: 4
tcgattaaaa attatcatcg ataaaattct aaaatttatt ttagtaaaat tattattatt     60
ttgatgaata agttaacaaa aaaattttaa taactttttg attcgccaaa aatctaattc    120
gttaaaaagt cgttccaaac agatatcgct tgttcgatga aaatgtccgg ttgttagaaa    180
atcataaatt ggttcaaata attttccaga acgttcgaaa aatattccc ttgtatcgga     240 taaataacca ttacaatttt ccactcgtgt tgcatgtgtt tctcgacaaa aatcagctaa    300

<210> SEQ ID NO 5
<211> LENGTH: 300
<212> TYPE: DNA
<213> ORGANISM: Dirofilaria immitis

<400> SEQUENCE: 5
tcaacagaaa tcgagattcc aaaaagtttc ctacaaatac ttaattatca atggatattt     60
agttttgtta tctgttatca taagttctgc ttccttacacg attaaaaatg tccaagaatt    120
ttttactatt caaatgaggg aaataaaaaa ccaatgccaa taatatccag aaactacata    180
catctttctt ttttcgaagc tcatctattc cggccgaaaa caatgaagaa cattaaaatt    240
cttaaaagat agtcttagcc ttttccttga ccactatctt aactgtcagc gctaaaatgt    300

<210> SEQ ID NO 6
<211> LENGTH: 300
<212> TYPE: DNA
<213> ORGANISM: Dirofilaria immitis

<400> SEQUENCE: 6
aatagtcgtc tcattacttt ttgactttta taattcgaga atcttatgta gtccttcact       60
ttacccttct tctgtcgaac taagaattac agcattattt tcgaatttaa tgtgtaaaag      120
acaatagcag attttgtaat tttgtgttaa cctcacttta tatttcgctt catatcgtga      180
cagagaatta ctatttcaga gagtattact tgtcaccaga gaatctccag aaagattttt      240
atttacgtcg gaaaatggac aaaaatggtt tcttatcatt agcactgata gctagtttcc      300

<210> SEQ ID NO 7
<211> LENGTH: 300
<212> TYPE: DNA
<213> ORGANISM: Dirofilaria immitis

<400> SEQUENCE: 7
tatctcttgt tgtgtgttct gcattgtatc aaagtgggta aattttgctt tagacgttga       60
cttattgtct tttttaagtt atattctagt ccatgttttt ctctttgcaa atatttttt      120 ccgccgccta tgattcattg ttttgtttgt aactctctat taagttgctt ttagtttgaa      180
ttgtatcaaa atttcaaaca tttaaaatac gcactagcac tattttttct tatctcaatt      240
aagcgaatcc cggaacaaga tttaatcgat ttccgaatca caattaaatc actggaaaac      300

<210> SEQ ID NO 8
<211> LENGTH: 300
<212> TYPE: DNA
<213> ORGANISM: Dirofilaria immitis

<400> SEQUENCE: 8
attttcctta acaaatcatt ttcaaacgaa aaacattaa aaagtgttaa ataaaatgg       60 tgatattgat aagaaattaa ttcaacctgc atatcaattc ttgtagcggc cattttctta      120
gcaagttcta tagcagctcg atccatatca ccttcttgct ctaatgtcaa ttccggttcc      180 ggaattttt ttatttttgcc attcttcatc ttttttttat tttttactga tatagctata      240
gaccctttct cccgtgcatg cctgtaggcc tgttctgata tacaggcttg tgaaccactg      300

<210> SEQ ID NO 9
<211> LENGTH: 300
<212> TYPE: DNA
<213> ORGANISM: Dirofilaria immitis

<400> SEQUENCE: 9
ttctggggta gttatacgga aaattagaca atgaagagaa tcaaaaaaca tgcgattttc       60
aaacagagga actttggtac ttttgcctcg acttacttta ttttaaaacc catacaaaat      120
aaatgtttca tttgattgat attgtcgtac taataattag agcttcaaca ttaggatttt      180
aataaccttc aatttatttc agaatttaag aaacttacgt atggatggag aaaatataaa      240
gaatggcgat gacaaataag atttgctatg aaaaaactaa tgccacaaga tccgaatgca      300

<210> SEQ ID NO 10
<211> LENGTH: 300
<212> TYPE: DNA
<213> ORGANISM: Dirofilaria immitis

<400> SEQUENCE: 10
tttatgaaca aaaataataa aaattaggat aacagatatc aatttctttt agctataaat       60
atacgcttcg attgaaaaaa gctttcaaat tataattaag gcatacgtta cgatatagac      120

| | |
|---|---|
| aattaagtcg acattaatta tttgaaatat tttaaatttt tttctctttc ttttttttcta | 180 |
| ttctcttcca aagtgtcaaa tagttatgaa attgtcagaa gctaaaatga taatattatt | 240 |
| caagtttatt acctaatctt ttatcacctc atttcttatc atttatctga aaatctaatc | 300 |

<210> SEQ ID NO 11
<211> LENGTH: 300
<212> TYPE: DNA
<213> ORGANISM: Dirofilaria immitis

<400> SEQUENCE: 11

| | |
|---|---|
| atgttgaatt tttaatgaaa cttttttcggt gcataagcat tacagatctg taagctgtgc | 60 |
| aaaccctgtt tctttgtaaa ttgaaacaaa gatcatttat tgtttccagc gtcgatttga | 120 |
| cctggataaa tgtggtacca aaagtagatg acgagaggta agtgcaaaca aaatgcacaa | 180 |
| aaatgatttt gatgcactca aatcattttt aagttttgtg caattttcca ttttatagtt | 240 |
| tcgtgatcgg ttgttattca tcaacttgat tttgtttgtt ttttgtgact tatatttcat | 300 |

<210> SEQ ID NO 12
<211> LENGTH: 300
<212> TYPE: DNA
<213> ORGANISM: Dirofilaria immitis

<400> SEQUENCE: 12

| | |
|---|---|
| tttgacactt tcagatacct tacaaactca tctccagcac ccaatttaca atatcgctgc | 60 |
| ctaaataaag aatttattcg gatatgagac tgtagttttc attccgtacc aatcatagta | 120 |
| gaacagatct atagcatggt gtcctactaa agttgtgact ggctattaag tatgtgggtg | 180 |
| ttttttacgtg tgcgtgggtg tttgtgcgtg tgtgcgtgtg cgtttctgca catattttcg | 240 |
| tgcgcggtgt ctgtgtgtgt ccgtttgtat atgccgagtg tagctgtgtg tatgttcttg | 300 |

<210> SEQ ID NO 13
<211> LENGTH: 300
<212> TYPE: DNA
<213> ORGANISM: Dirofilaria immitis

<400> SEQUENCE: 13

| | |
|---|---|
| cactcataat atacctgtca acaaactcag aaatctgaat aaaatgacgc aaaaatgaca | 60 |
| aaaacatttt atcaaccttt tcttcatcac tcccccgcat ttccaatttt cttccaaact | 120 |
| gttttttgtcg tgctacaaag tcatcagcca cttcattttc ttcaagatgg ttcgagacgc | 180 |
| cattcttgga ttcaccccctt atttcaactg tttccgaagt cccagcagtt gaagctgaac | 240 |
| ctagcattta tatcaccacc cgatgtcaaa aaatgacagc ggtcagagaa tacgacttcc | 300 |

<210> SEQ ID NO 14
<211> LENGTH: 300
<212> TYPE: DNA
<213> ORGANISM: Dirofilaria immitis

<400> SEQUENCE: 14

| | |
|---|---|
| gctaggtcaa cagttggttt atttggactt atacgatatt aaacataata tcgcctcata | 60 |
| tacacagaaa tatcaaaaaa acgaacacag ctaaatcgaa gaatacgaac aaatgtttta | 120 |
| aaaattatat taaatctttt aatgctctct acaatgtcgt atcttccctt ttgtctgtat | 180 |
| ttctcctttc gttccaccac tgctatttct catgcctttg aactatggtt ctcgttgcgt | 240 |
| cgaattgtcc tcgaaactgt tgtttctgtc gaattacgtc gaactgctgg actttgtcgg | 300 |

<210> SEQ ID NO 15
<211> LENGTH: 300
<212> TYPE: DNA
<213> ORGANISM: Dirofilaria immitis

<400> SEQUENCE: 15
atatctcact tctgacataa attgaagtgg cactgatttg aatgaaatga taaataaaat      60
aaagacgaca aggtagtgga aaaaaaaga ggagaaaaca ccgtttagtt ttggatgcaa     120
gctcgaatct gagttttctt gcaaaccgta cactgatcaa ttttcttaca caaacataag    180
aaaaaaagaa gtgattttac tgtagctgta tcgtataatt caaatcatat atatatatgt    240
ttcaataatc tatacattta tgtatatttt tttttgaatg aacagtgaa tgatttttaaa   300

<210> SEQ ID NO 16
<211> LENGTH: 300
<212> TYPE: DNA
<213> ORGANISM: Dirofilaria immitis

<400> SEQUENCE: 16
acaaatgcca tcgggagaga aatatcgttg gcgtactgat cacattggcg gtatcacttc      60
tttgaaaact ccagctggta ttgtgtatca tttcatgcaa tacgctattt ttgatcgaat    120
atgtcgacgg cgtagtgttt cattttccaa cgcatcttac gttgcgtgta tggatgatga    180
cggacaatta ttggaatatc aaacaccgga tcgattgcat ccgtaaccct tgaaacgtga    240
catatatggg agagtagtgc aaataacttc agatggcgaa atattttct tcgaatatgg     300

<210> SEQ ID NO 17
<211> LENGTH: 300
<212> TYPE: DNA
<213> ORGANISM: Dirofilaria immitis

<400> SEQUENCE: 17
ataatatata tttccattga taatattttt catattatgt gatgtttgaa attttctgca      60
attgctacat tccgattaaa aacttttatt atccgtactg gagaattttg cttttttttg    120
acggtttgtt caataagttg tcaatatatt gtctgcctta gtaaaaccct tctaatctat    180
ccgttcgaat tggaagttga aagttcagca tcattctttt agtgaggtgt ttaagttgtt    240
caatagatat tattagaac gatctcaatt aaaatcttct gaatgatttt atgttttat     300

<210> SEQ ID NO 18
<211> LENGTH: 300
<212> TYPE: DNA
<213> ORGANISM: Dirofilaria immitis

<400> SEQUENCE: 18
gcagcacatt gcacacagta aactgcaaac tgaattaaga gatattgggt tgaattattt      60
ctaatttaaa aggatataat aaatgacttt gatgattgtt gatttaaagg tatctcggaa    120
gactccatca gtctcagtgc tctagcaatc gctataggta ctaaaagaaa agaaaagatg    180
tctcgttatt cactttgaaa tgtacatatc aaatcatttt gtcgtatgaa attaagtata    240
ttatgtctaa tcgtatcatt cgaaatgaat ttactgtcac tgttagaact atttaggcag    300

<210> SEQ ID NO 19
<211> LENGTH: 300
<212> TYPE: DNA
<213> ORGANISM: Dirofilaria immitis

<400> SEQUENCE: 19

```
agagttcaat cgccaagttg ttcttttttct cgctcgcaga gatcaaaacg gtgttggcta    60
tacactcatt catcaggctg tgatagacat ctcttagaat tcagtgctt ttctggatga    120 aaacattatt tctcaaacat gacacttaag gacaatagtg cgtgacttct tgttaacgt    180 acacgagaaa acaaaacaga tgatgcttgt tatcttggtg ataaatgtgt attcagaata    240
atgttatata tctttgcgtg acaaatatca tttcgttata cttcggatac gccttttat    300
```

<210> SEQ ID NO 20
<211> LENGTH: 300
<212> TYPE: DNA
<213> ORGANISM: Dirofilaria immitis

<400> SEQUENCE: 20

```
aactttactt gaactttttt ggtgttcaat tttgaatatt ataccaacca ttcagaagac    60
tgtatataga aatgaacctt caagaattaa tcgaaatttt tattaaaatc ttttatttga    120
atatttcatt atttaaactc attactattt gcagtatatt attagatcta atgtagaaaa    180
aaaaatcaga tggcaaaaat aatatcatag gtttgttttt aaaattcatt gcaaaattca    240
gtgcgccgtt ccagtcgctc gtaattaccc tatccctgag ctttacaaaa gaatgctttt    300
```

<210> SEQ ID NO 21
<211> LENGTH: 300
<212> TYPE: DNA
<213> ORGANISM: Dirofilaria immitis

<400> SEQUENCE: 21

```
aggtatctag atagcataat aaattactac acaaaccgat ggaaacgcaa gtttggcgtt    60
gcgtgttgat acaaaatatt agagccaagg atggtatcac atgtaaaact gcaattttgc    120
tatttgttta aagcaaataa gaaataaata tttcgttctt attctttaat ttatttcatc    180
agatggcttt gttataccat aattgtaaat ctgtcatatc ttaattgcgc aatagcccaa    240
gattcttgta tattcttaca tttcacaatt tattttctta tttctagttt tagaattata    300
```

<210> SEQ ID NO 22
<211> LENGTH: 300
<212> TYPE: DNA
<213> ORGANISM: Dirofilaria immitis

<400> SEQUENCE: 22

```
aatagctact cacagcttaa gttaactaat ggattcttga atttatttaa gcgtgtagtt    60
aagcgattaa tatgatggat gcccagaatc gctttgtctt atagttttgt ctcgacagaa    120
aggatgcatt gttgtcttga atttgttcaa gggaaaatta aataggtttc tttcaatgac    180
tcctattaaa tttttttgaa tttaggcttg cattgcgtgt tctgatccac tattagcacg    240
tacgggtatc gcagtgccat gtgatgcagc actatgcaaa accacctcc atgtcacttg    300
```

<210> SEQ ID NO 23
<211> LENGTH: 300
<212> TYPE: DNA
<213> ORGANISM: Dirofilaria immitis

<400> SEQUENCE: 23

```
tctgttgtaa gtttcacaat ccagttaatt taagctcagc ttatttgaaa ttttcaacaa    60
aattacgaaa attactttct cggttcattt ttttcaacca ccaaatattt agcataattg    120
gcctgaaatc gtcaaagttt acaaactttt gttcagcaat cttctcttac tcttacaata    180
aacatgatta acttgtcgtc ataccaatct cgtttatagc aaattctttt caaaaaaaca    240
```
ttgctacaaa ttttatatcg catcatttca acacgcataa ttattttca tatatgaaaa    300

<210> SEQ ID NO 24
<211> LENGTH: 300
<212> TYPE: DNA
<213> ORGANISM: Dirofilaria immitis

<400> SEQUENCE: 24
ttcacaatcc agttaattta agctcagctt atttgaaatt ttcaacaaaa ttacgaaaat    60
tactttctcg gttcattttt ttcaaccacc aaatatttag cataattggc ctgaaatcgt    120
caaagtttac aaactttat tcagcaatct cctcttactc ttacaataaa catgattaac    180
ttgtcgtcat accaatctcg tttatagcaa attcttttca aaaaacatt gctacaaatt    240 ttatatcgca tcatttcaac acgcataatt attttcata tatgaaaaac catattataa    300

<210> SEQ ID NO 25
<211> LENGTH: 300
<212> TYPE: DNA
<213> ORGANISM: Dirofilaria immitis

<400> SEQUENCE: 25
attaactctg aacccaaaga ctgttggtta aaataaagat ctattttagt tatacatcta    60
acattaaagg ttttcgtacg gaaacaagta ggtttgataa ttttcatgta actgtaaaga    120
acacctgtga aagggatcag taaaatttgg gggatgtagc acggaaatat gaagctgagt    180
gttttgtacc caaaagtttt tcaaatctgc gaaataacga gaggtgtaat gatcgttttt    240
aaccaaattt tttgattcta atccttccca cagttttgaa attcagtaag catttctttt    300

<210> SEQ ID NO 26
<211> LENGTH: 300
<212> TYPE: DNA
<213> ORGANISM: Dirofilaria immitis

<400> SEQUENCE: 26
ttgcaacaaa tcaataataa aagacttgcg gctaacaata tatttgattc ttttttaccg    60
ttattattat gacaggtaat aatagtatta caagcatatt tgtaggtgtc aattttttca    120
attcaaattt tcttaattca ttatttcttc ctttccttaa taaatagtct ttccatttaa    180
gaattaactt tttgaaatct ttaatgagaa gacacaaaag attccggata attttgcatc    240
atcttttcta tttcgcgtta gtattttatg ttttcaacag attttttatga tttaactata    300

<210> SEQ ID NO 27
<211> LENGTH: 300
<212> TYPE: DNA
<213> ORGANISM: Dirofilaria immitis

<400> SEQUENCE: 27
gataaaatgg gttcttgtca agctcatttg gcatatcttc gtcttctata tttatatcct    60
ttaatatctt ctcttttttc aaattttcct tcccgacgtt ttccatatcg acctctttct    120
tcataaattt atcttcctca tttgcctcat ttttgactt ttcatccgtt tcatccttat    180
ttttcttttt ttcatctcct atttaccctt ttccttatc aacttctatc ttaactttct    240
caatgttttt tttatttcct ttcatctttt tgttttcttc tattgacata ctataacaaa    300

<210> SEQ ID NO 28
<211> LENGTH: 300
<212> TYPE: DNA

<213> ORGANISM: Dirofilaria immitis

<400> SEQUENCE: 28

| ttttacgaac aattatttca taaaagattc gtattttttga ttagttttta agaatttttt | 60 |
| tttattattt ttagccaaca aatatatttt tcaaaattgt taaatttgaa attataaatt | 120 |
| tcaactaaaa aaaagcaaaa agctaagcca atagaaataa catacatgtg taatataaaa | 180 |
| tataaagtat tcgaaatgaa aatcaaagtt tcataacaaa aaacaaaaaa tattctaacc | 240 |
| ttttagattt catcaaaact tcactaaaaa gttaaattta aattttcaaa ttgttataca | 300 |

<210> SEQ ID NO 29
<211> LENGTH: 300
<212> TYPE: DNA
<213> ORGANISM: Dirofilaria immitis

<400> SEQUENCE: 29

| cgaacaatta tttcataaaa gattcgtatt tttgattagt ttttaagaat ttttttttat | 60 |
| tattttttagc caacaaatat attttttcaaa attgttaaat ttgaaattat aaatttcaac | 120 |
| taaaaaaaag caaaaagcta agccattaga gataacatac atgtgtaata taaaatataa | 180 |
| agtattcgaa atgaaaatca agtttcata acaaaaaaca aaaatattc taacctttta | 240 |
| gatttcatca aaacttcact aaaaagttaa atttaaattt tcaaattgtt atacaatgat | 300 |

<210> SEQ ID NO 30
<211> LENGTH: 300
<212> TYPE: DNA
<213> ORGANISM: Dirofilaria immitis

<400> SEQUENCE: 30

| tcaaagacaa aatgaagaac ttaacaaaaa aaaggccaat aaataaaggc tatttcgtga | 60 |
| aaaatctaaa aaaaaaaaga tctgttcctt tcgaatcaag tgattcttcc tactacattc | 120 |
| gtgttgtaat tcttacttgt atacagtccc cagttttttcg acgataaaaa acatttcgat | 180 |
| aagtgagttt gaattaattg aattttaaaa gatcataaaa ataaaatcaa ataaaaaga | 240 |
| ccaaaattaa gtctgataat tccagaaaac acaataataa atatacaaat aataaaaact | 300 |

<210> SEQ ID NO 31
<211> LENGTH: 300
<212> TYPE: DNA
<213> ORGANISM: Dirofilaria immitis

<400> SEQUENCE: 31

| aaataattca ctaatttctc atcatcaaat tatttcgtac aatcgataaa tcaacgatta | 60 |
| taatagcgaa gagaatgaaa attaatgtgg tgcacagtat acggacccca tatacaatgt | 120 |
| tcaacagaga tgaacatttt ttttctatta agttttctg ttcggcgaaa gaaagacact | 180 |
| ttctaacgat gctttcctcc caactcccct tgcaatgata gaggatgcag ccaagattcg | 240 |
| tcgactcaag cagcatcact caaccggcca tcacttcggg acctttttcc ctgccttta | 300 |

<210> SEQ ID NO 32
<211> LENGTH: 300
<212> TYPE: DNA
<213> ORGANISM: Dirofilaria immitis

<400> SEQUENCE: 32

| cattgcgaat gaccgctatg gaatatcaat tagcagatat taatcgtgaa ttaagcacat | 60 |
| tggtggaatt tttacgacca aatcgaattt caaaaaatgc tacacttgca acatcagcaa | 120 |

```
ccattgcaac atataacagt acttcgatgc gtaatgtaaa aaagaaatgt aatgcatctg      180
aaagctgaaa attcatctga tatattgaag caaaaggtaa gattattttt aagatatcat      240
tcttgatgct ctcataattt ctacatcaaa tttaatcaaa cgattcattt atgttcattt      300
```

<210> SEQ ID NO 33
<211> LENGTH: 300
<212> TYPE: DNA
<213> ORGANISM: Dirofilaria immitis

<400> SEQUENCE: 33

```
ttcttgttgt acctatcata gatgataact taagtaccaa tagcaatagt gcaacgatgc      60
aaggattctg attaatgatt ataaaagttt aaccaatctt cttcattcct tctaatcaag     120
agaaaaaaaa atgagaacat ttttatgaca tttgaagaaa ggcaatttat cgctgaaaat     180
tctactgcga tatggaagta tcagatagag aaaataaata ttaaaatatg gatttcatac     240
gaaaaatgat aaaagataat aatttacatt ttggtgcttt actgatatga ttggagtatt     300
```

<210> SEQ ID NO 34
<211> LENGTH: 300
<212> TYPE: DNA
<213> ORGANISM: Dirofilaria immitis

<400> SEQUENCE: 34

```
cgatatttt tggacgaatc aaaccttttt gggaaatcat ttgatgtcac aagcatggtt      60
tgagaaattt ttttccgaat tagttctgct aaaaatactc caaatgagtc tagtggaatt     120
aagctaagca ccttaagtaa gttgagaaaa acgtttccat ttgactaaca aggctagtat     180
atcgacatga gacagaaatg gttattactt cactcacttc atgaagcgaa tacgaaatat     240
ctgttcactt tagtttcaat ctactatttt accaataaac gtgttctttt ccggataaat     300
```

<210> SEQ ID NO 35
<211> LENGTH: 300
<212> TYPE: DNA
<213> ORGANISM: Dirofilaria immitis

<400> SEQUENCE: 35

```
tcttaattga ttttcttaac tcgaaacact tgtcttgatt actgtgctgt actttatctt      60
attaaattaa ataatttcca tgaccacttc ataccattga ccatcaaact ttgatgaagt     120
ttatgtgtga agtgccaaac aatcattcat cccttcagtt taacttattg ctggtcaaat     180
tcataaaaat gcaaattatc aagcagatag taattcagtg aacgtagcgt attctcgaaa     240
tttctttcct tgtatttacc ttatatagaa caacgtatat ttgtagcata tattcaatat     300
```

<210> SEQ ID NO 36
<211> LENGTH: 300
<212> TYPE: DNA
<213> ORGANISM: Dirofilaria immitis

<400> SEQUENCE: 36

```
tttctgagtt tgcgttacag cgccaaatct tcacggagat agataaaata cttatcgtga      60
aattttggcg ccatgattta aaaacacgg agataaaaat aaaatgctta tcggtgataa     120
tttagcgcca taatatgaat gaattgaaaa acaatttga gtagaaacat gacatagagt     180
tttcgttttc tggctacgaa aatggatgaa ttttctgga atcgaattca gtcaaagaaa     240
taggaacgtt gttactaaat gatcgaaaag ctttctaaaa ttaaatttat gacgtctaag     300
```

<210> SEQ ID NO 37
<211> LENGTH: 300
<212> TYPE: DNA
<213> ORGANISM: Dirofilaria immitis

<400> SEQUENCE: 37

| | | | | | | |
|---|---|---|---|---|---|---|
| atctaaatct | tcgttttata | gtggtaagac | ttccatttgc | tgcattcttg | caaattaagc | 60 |
| tgttgaaaat | acttttttt | ttgatagatt | tccaatttaa | tcatattata | agaagaatta | 120 |
| atttcgaata | gaattttaa | atcatttaaa | ctttaagttt | taaaactaat | ataagttatg | 180 |
| cagatttcgc | gaaaaagtct | catttgttaa | ttcaattatt | ccaaaatgta | ataattttat | 240 |
| aaattcaaat | ttaaactact | actaacttct | gaagtcagga | gccagtagca | acaacgtaat | 300 |

<210> SEQ ID NO 38
<211> LENGTH: 300
<212> TYPE: DNA
<213> ORGANISM: Dirofilaria immitis

<400> SEQUENCE: 38

| | | | | | | |
|---|---|---|---|---|---|---|
| aactttacat | ttatattcaa | ttttttttta | ttttgtttgt | tttagaaat | ttgaaaatgg | 60 |
| gtactaatca | gtgtcatttg | cagcctctta | gaccctcttt | ataacgaccg | attcgatgaa | 120 |
| atacgtcatc | aatatgccag | tttattgttc | gggtggagaa | tgttttcaaa | agttgctgaa | 180 |
| gtgatgaagt | atagtgagaa | tgcaccttat | tcagcaccat | taagaagtaa | attttgtctt | 240 |
| tggaatttga | caaagacaaa | gcaggaagtt | gacaacgatg | ttctgatgaa | acggtttcga | 300 |

<210> SEQ ID NO 39
<211> LENGTH: 300
<212> TYPE: DNA
<213> ORGANISM: Dirofilaria immitis

<400> SEQUENCE: 39

| | | | | | | |
|---|---|---|---|---|---|---|
| gtctattttg | gctgtcttct | aataattcat | tttgtaacct | tttgaaatat | gataaatgta | 60 |
| gaaattttt | cttcctggtc | tataatagtt | taataatgtg | ttgtagtaat | agttttggtg | 120 |
| ccgttgaaat | atttcaatga | tatgctatcg | caaaattagg | aattcaaatc | aaggttacaa | 180 |
| gataattcaa | aaacaaacaa | cgtaaaaatg | aaataatttc | ttcttcttac | ttaccaacag | 240 |
| gcatatcatc | atcatcctca | aattcatgac | tatatttaac | attgtcatat | ttgaataatc | 300 |

<210> SEQ ID NO 40
<211> LENGTH: 300
<212> TYPE: DNA
<213> ORGANISM: Dirofilaria immitis

<400> SEQUENCE: 40

| | | | | | | |
|---|---|---|---|---|---|---|
| cgacgcaaaa | atctttcaaa | ttgtcaccca | gttctctaag | tgattccaat | gatgttggta | 60 |
| aacattctgc | atgatgtacc | gggtaatgaa | ctaccaagtt | gttttttgct | tttaatacaa | 120 |
| ctcgcaaaga | ttctgaaaac | catgaaatta | agaaagatta | aataatctg | aactcttttt | 180 |
| ttcattttc | cttgaactta | gcaatatact | gagttggata | aaatttagaa | acgaaatttc | 240 |
| gcaaatttat | tcagtaaatt | caggaaaact | cggtttcggt | attctaaata | taaatagata | 300 |

<210> SEQ ID NO 41
<211> LENGTH: 300
<212> TYPE: DNA
<213> ORGANISM: Dirofilaria immitis

<400> SEQUENCE: 41

```
gtttctttgg tttatctcag taagatttgg gcggaaattt cagttatact tttcatttcc    60
atgtgctgtt ttaaatttct tccatattag tataattttc aaataattgt agcgtcactg   120
gtttatttaa ggataacagg ttggactgca gtggctgaga agtgtcttgc cggtcaattg   180
tttgttggtg atcaacttgt acgagttact gatatcgaca tatataatac acggcaaatt   240
ccattcgttt tcagtactgc atcaaaaacg ggattatcgg tactttgtaa atcgcagtat   300
```

<210> SEQ ID NO 42
<211> LENGTH: 300
<212> TYPE: DNA
<213> ORGANISM: Dirofilaria immitis

<400> SEQUENCE: 42

```
gacccctgct cacaaggcag ttcccacaga caatcacaca tctaatcaca cacatcaact    60
catccgacgt aggctatcaa taaggaaaat tgcattgctt tatcgtctaa ctgtaataaa   120
catctacata atgaaattat ttcgccacta tgacaactaa tatcgcccaa tgcaaatatt   180
tgtctcagag ttattccctt ttaacagctg ttgaacgaat agataggacg tcatgtggat   240
gatctacttg tttcaaaggt tgaggtaaca catgaaacac atgaaaacgg taatttaaaa   300
```

<210> SEQ ID NO 43
<211> LENGTH: 300
<212> TYPE: DNA
<213> ORGANISM: Dirofilaria immitis

<400> SEQUENCE: 43

```
aaagaatggt cagcaagatg tggaaaatcg attactatag ttgaagtatg aatcgaagag    60
gttttttaa attctaagag aacgaataat cggcaaagag aaagttgagt aaccttattt   120
tgccttgttt tcagtcaatt tataatatgc ggttaattgt gttaaagaaa gtacaaggta   180
tgaaatctaa gccaagaaat aagagaaaac agctaatgat tatttctgca ttttttcttt   240
ttcgacacaa acttggaacc agaatcaatt gaactagtaa tcagattttg attattgctt   300
```

<210> SEQ ID NO 44
<211> LENGTH: 300
<212> TYPE: DNA
<213> ORGANISM: Dirofilaria immitis

<400> SEQUENCE: 44

```
ttagattttg ctgaagcatt gttggttaga tcgatgaaaa tataattatg agagattttg    60
ttgaaattca gcaacaaaat tattattcat gtcttcatgc tgtcagtttt gttttattt   120
cttctttgac atcggttata ttttgtctt ccaacaatat aaaaaaaaaa ttataatcaa   180
ttggtaatca aattaaaact ctaattgtta gctccctaaa tcagctttaa aaaataatt   240
gcttaattgg tatttgctac tattagcaaa ctgaaactat ccttttctcg aatggtgaac   300
```

<210> SEQ ID NO 45
<211> LENGTH: 300
<212> TYPE: DNA
<213> ORGANISM: Dirofilaria immitis

<400> SEQUENCE: 45

```
atgagctgat atttgatatg catattaaaa atagggtaaa ttacattaag ttagatatcg    60
ttcggataaa ttaattagaa aaaatgttta ccaattagat cgcaatgatg taaaatttca   120
cgtatttta ttcttaagat ttatttgcaa aattcaaaaa tatgtcttat gaaaaataat   180
```

```
atttctgtgt aagaacaagg gaccgattca cttgatttat tcgcaaacaa tcgaaattca    240
aaattagtaa ttttaaatat tgctttattc aaaccatacc aataataatt tgagagattt    300
```

<210> SEQ ID NO 46
<211> LENGTH: 300
<212> TYPE: DNA
<213> ORGANISM: Dirofilaria immitis

<400> SEQUENCE: 46

```
attgattgat tcaaataaga aatttaaatt atttcccctt tttttcaaaa gatttaacaa     60
atattattta tttgatctcc tcgttcgttc ttatcttttt gattatcaat ccatcctcct    120
ccatcatata gctaatttat tttttgcatc gtaaatcaat tgatgtatga ttgatttctt    180
gattataaaa agttagaaga attgaattgc ttaaatttaa ttattgataa tgaaatatta    240
ttatatttca aaatgatacg aagaaatatg acgatgataa gagaaaatat gatatttatc    300
```

<210> SEQ ID NO 47
<211> LENGTH: 300
<212> TYPE: DNA
<213> ORGANISM: Dirofilaria immitis

<400> SEQUENCE: 47

```
tacgataagt tattttattt tacacatctc catccttgac tagtgtccgt gccgactgtc     60
ggacttgaac cgacaaccta ctaattacaa gtcagttgct ctacccaatt gagctaagcc    120
ggccatctag aatgtgcgac cccgtcgtgg tacatcttct ataatcgttt ggtattcagg    180
actctcttct ttcgtgggtg gaggatcttg atacagttga ctattaaaaa tagggccttt    240
gttagtctgt tacaactcat agacaaaggc gacaattta gcttacatct tacgttatgc    300
```

<210> SEQ ID NO 48
<211> LENGTH: 300
<212> TYPE: DNA
<213> ORGANISM: Dirofilaria immitis

<400> SEQUENCE: 48

```
atggtagaaa attatatgaa aaatatcat actaaaaata taacagattg ttataaggta     60
tggtttaaga atttacaaca attgattatt tatgataaaa aaaaaaaaag taaatcagtg    120
aatcattaag atagttatga taagcagttt gtattcggta aagcgaatga ttagaggaat    180
tatgggacga aacgtctata acctattctc aaacttttaa tgagtatgac gtgtcttgct    240
tgcttaaaat tatttcaatg atcatttcac tttaccagta tgatcatgat tagacttgaa    300
```

<210> SEQ ID NO 49
<211> LENGTH: 300
<212> TYPE: DNA
<213> ORGANISM: Dirofilaria immitis

<400> SEQUENCE: 49

```
ttagtatcga tattatcaca aatgatatca ctttcatcaa tactggatac gattttatta     60
gtatcataat tttgtggctc gcattccgaa agttttacac gtagaagatt aacctgcaat    120
atgatttatt ttatcatttt cgaatatcca actttgaaat aattcgaaaa tgttgaaaaa    180
ttttgaaaaa ttgttaacaa atattacaa aaatatcaaa tgaaattaaa taactgtcca    240
tttcaaaaaa agaagaaaaa ttatgaaatt accaattaaa aacaggactt attaattaaa    300
```

<210> SEQ ID NO 50
<211> LENGTH: 300

<212> TYPE: DNA
<213> ORGANISM: Dirofilaria immitis

<400> SEQUENCE: 50

| tgtggaaata | aagtacaatt | aattgctgtt | cgcttaataa | tattatttc  | attcttggct | 60  |
| ttttttttct | ttcccgtga  | tattataaaa | tatagttttt | taatttaac  | aaatcgtcat | 120 |
| aattatttaa | aaaatactga | ggtgagtaaa | tgtaattggt | tgctggaaaa | aaagtgggtg | 180 |
| atgagaggtg | aatgaaagca | gaatagttta | tgattgcatc | aaatttcctc | cttaatctgt | 240 |
| gattaaaatc | aaacaaaacc | cgaaaagttt | cttcttcgcc | ttttcttct  | ctttgtttca | 300 |

<210> SEQ ID NO 51
<211> LENGTH: 300
<212> TYPE: DNA
<213> ORGANISM: Dirofilaria immitis

<400> SEQUENCE: 51

| cgaaatccgc | cgcgtgcatt | actttgcgct | tgttgattac | gacgcatttg | ttcgtcgttg | 60  |
| ataaccttat | caatcatcat | acgtccgtta | cgtatgcaat | caacatcgcc | agttaggctg | 120 |
| aaatcaaatg | gatggcgatg | atatcaaaaa | caaaaataag | gagtatttgc | tgaatcattt | 180 |
| cttttctgt  | attattatca | aaattttctc | ctttccattg | tttccttctt | aatcaagtga | 240 |
| atgctcattt | catttgaaa  | taatccaacg | taataattcc | ccatattccc | aattactttc | 300 |

<210> SEQ ID NO 52
<211> LENGTH: 300
<212> TYPE: DNA
<213> ORGANISM: Dirofilaria immitis

<400> SEQUENCE: 52

| agaaatatta | aactttgaaa | agatgtgaca | tgttctgtaa | caaaagccca | aaatttcgac | 60  |
| tgctgcggct | tgaagtaaaa | ttttggaata | tgctacatca | gtagtgcaac | agatggttcg | 120 |
| ataaatagtg | gtaagtgatg | ggaatcctag | gaatagatgg | gaattgtatt | tcagatataa | 180 |
| atttgatgca | tattttcata | gttgattata | tctacgatca | cacgttgaat | attctaaaag | 240 |
| caaactgtaa | ttaactaatt | gaatttgaaa | atttccaaga | attaaaattg | gtaacaaaaa | 300 |

<210> SEQ ID NO 53
<211> LENGTH: 300
<212> TYPE: DNA
<213> ORGANISM: Dirofilaria immitis

<400> SEQUENCE: 53

| attgtcagga | atgagaagca | agttttggat | acttaaggga | tgaatggaac | acatacatgg | 60  |
| cagaaaatgt | tagtaatcaa | accatttaaa | ttacttagcc | actatgctaa | actttctaga | 120 |
| agtatggttg | aacgtttaaa | aaccttcgca | aaaattgtat | tagattatct | taatcttccc | 180 |
| tacatcaaaa | cagagaattt | tgttctacg  | acgtgagtct | gcatgtatta | aggaagttcg | 240 |
| tatcatgacg | taaatatcct | gagtgattat | tgaattcaga | aaatgagctt | tttcatttgg | 300 |

<210> SEQ ID NO 54
<211> LENGTH: 300
<212> TYPE: DNA
<213> ORGANISM: Dirofilaria immitis

<400> SEQUENCE: 54

| atatgagtgt | tacatgtgta | cgttacatgt | aaatattata | tgttatatgt | aaaaatgtca | 60 |

```
tgtatagcat ctattcacgt gtacgtacac gtgtatatac atatacattg atacttaata    120
cgtatacgca tgaatgaaca gatattatat atttacgtac actagactca catgtacctc    180
tgtatacgca tacatgtaca gatatatgtt tgacatacgt aaattcatat atgctttat     240 ttatgcttat attaattgtc acatacatgc cttatatttt cgttgttata aacacataaa    300

<210> SEQ ID NO 55
<211> LENGTH: 300
<212> TYPE: DNA
<213> ORGANISM: Dirofilaria immitis

<400> SEQUENCE: 55
gaaaataaaa ttagctgaaa atatatgcga ggtaaagcac acagaagaat taacttaagg     60
taatatattg taagaatttt tatattcggc gcacctaata attttagac cgcatatgcc    120 cagtatttga aactggtagc gctgttcgta cttgctgttg ccatgttat gtatatgata    180 ccattcctaa atactttgc ggctgtggtt ccagtgttg atgtgactgg tatgatgcct    240
aacactggat ccttccatct gcggcatttt gttgaaattc ttattgatgt gagctgttta    300

<210> SEQ ID NO 56
<211> LENGTH: 300
<212> TYPE: DNA
<213> ORGANISM: Dirofilaria immitis

<400> SEQUENCE: 56
caactgtgaa tcataaacat tacttaaatt aatgaagcta gttaacgaca aatatatttt     60
tttatgtatc agtgctatca tataacataa aaacttactt tcattaataa atgagctcaa    120
atattgactt ttgtccaaaa tgctcaaaat gtcgtcataa tatttgaaat gaagataatt    180
tcacgctttt cgaagcctcc tctcacgtct tttaatcttc ttttcttctt cttgctctaa    240
tggttctgcg aaaaaccacg gtgcaataat cactttccat aatttataca gtacataagc    300

<210> SEQ ID NO 57
<211> LENGTH: 300
<212> TYPE: DNA
<213> ORGANISM: Dirofilaria immitis

<400> SEQUENCE: 57
ctgcttaact cttttcattt ttcagagaat cttctctaaa attgtgaatt gatccaaacc     60
aaagaatatg gataatgtga ttcgaattcc tggaatttag attttgagag ttttgaagtt    120
tttaaagaga ttgaatttct gtgaccttct ggtatatttg atgtcatttc gggatgcgta    180
tttttgccga aaattttggg cctcactgca atcttgttaa aagtcaaaaa aattcaatcg    240
tagaatttcg ggtttacctg atattactgg aaatctctga tctttgttct agattgctgt    300

<210> SEQ ID NO 58
<211> LENGTH: 300
<212> TYPE: DNA
<213> ORGANISM: Dirofilaria immitis

<400> SEQUENCE: 58
ataaagaatt tgcaactctg tataccttt tgcagtgcaa aagcggatga attcttcact     60
gcagtgtgac agattccttt gataaaattg cttcgttctt atgtaaactt ggaaattctc    120
ggtagttatg cttttgctag ttgaaaatgt tctgctcttg taaaacatgc aaaaagagat    180
tatctttgtt ctattatgga aagattcttt tgaaattttg acgactgaga agacaaattt    240
tatcccaact tgtcatctgc aataaaaatt tttcctgacc tgtttcttaa ccttccaagt    300
```

<210> SEQ ID NO 59
<211> LENGTH: 300
<212> TYPE: DNA
<213> ORGANISM: Dirofilaria immitis

<400> SEQUENCE: 59

| | | | | | | |
|---|---|---|---|---|---|---|
| aaaatcaaat | caatatgatc | agataactca | tacttatctt | actgaaaatt | cctcattcaa | 60 |
| gggaaataaa | taattgcaat | tcttgattcc | gatcatggat | gattttcaag | caaattacca | 120 |
| atgatatcta | tcgataacga | ttacagcata | cagctataac | ttattattga | ttgaattgat | 180 |
| gaaaataatt | ttaccagaaa | tttatcaatg | tttatctcat | tgcagtatac | gatgtttagt | 240 |
| gtgacaacac | ttttcttgg | aataattgtg | cataaatcat | tgattgcatt | tagtattgga | 300 |

<210> SEQ ID NO 60
<211> LENGTH: 300
<212> TYPE: DNA
<213> ORGANISM: Dirofilaria immitis

<400> SEQUENCE: 60

| | | | | | | |
|---|---|---|---|---|---|---|
| tcctgcccac | attctttcta | ctttagataa | tcaacaggag | ttagttgaaa | gagaagacta | 60 |
| ggaacagttg | caacttctga | atctttctga | ctttctttcg | ttttgtaaat | tatttatttg | 120 |
| tataaattta | aaattcgaag | agaaataatc | caaggtccaa | cttctttttc | tgttagttct | 180 |
| tgcgaatgct | ccatcaaaat | gcaaaaatat | gattagaatt | ctgatggaaa | ttaacaaaat | 240 |
| cgattagata | agaaaagtac | aaaacagaaa | ctaactttt | ctcccatttt | catattatag | 300 |

<210> SEQ ID NO 61
<211> LENGTH: 300
<212> TYPE: DNA
<213> ORGANISM: Dirofilaria immitis

<400> SEQUENCE: 61

| | | | | | | |
|---|---|---|---|---|---|---|
| tcattgcttt | aatactttt | aacgagaatt | ttctcgatca | aaataagatc | tgcaattgat | 60 |
| atacgtcaat | aagcgaacat | tagctgtatt | acacgctaat | attcacatat | gatgaacgtt | 120 |
| gtaagcgtca | tacatcaaca | tatatccatc | cgataaataa | tgaccactac | acattgctac | 180 |
| caaccatcct | atcccgccac | tatttgaaat | gaactgagaa | ggagttatcg | acacaggctt | 240 |
| cctagcaacc | aaacaaaaga | cgagacagat | gaatagatag | acagacagac | gaacatacaa | 300 |

<210> SEQ ID NO 62
<211> LENGTH: 300
<212> TYPE: DNA
<213> ORGANISM: Dirofilaria immitis

<400> SEQUENCE: 62

| | | | | | | |
|---|---|---|---|---|---|---|
| agattctggt | tattattgta | tttctgattt | atttaatccc | aacttaaaga | ttcattggct | 60 |
| attgtttagc | atctatatca | attttataaa | taaatagtaa | tacctgatga | aaagcaataa | 120 |
| ataattagat | gcaaattta | attagataca | gtttgatgga | aacattgaa | gccatgtaca | 180 |
| actaatttat | gcatgttgaa | ttatgcatgc | ataattaatt | tatgcatgac | agcaagtttg | 240 |
| gtataaaatt | aattttgtat | gaagataaaa | ttttataaat | aatgataata | atgctggtaa | 300 |

<210> SEQ ID NO 63
<211> LENGTH: 300
<212> TYPE: DNA
<213> ORGANISM: Dirofilaria immitis

<400> SEQUENCE: 63

```
attattgaaa agaataatgt agctaattag ttgaagctgt taaaagtaaa gctaaaaaga    60
tgatggaaat tattcgtata aacattcttt gtaaacaaac agtcatttct gtgaataaac   120
aattataatt ataaacaata cttttcaaga caataaaaaa attaggaagc attgttgtga   180
taatcaatag ttgatagact gtcaatgtat ttttatcagt cgtgctgctt ttttttccctt  240
tcttgactca tttattttat tatttattga tagaatgtca atattctagt catttgttat   300
```

<210> SEQ ID NO 64
<211> LENGTH: 300
<212> TYPE: DNA
<213> ORGANISM: Dirofilaria immitis

<400> SEQUENCE: 64

```
atcttaactt gctttaaaca aataaattaa aacagcccaa tgttccaaga aaaaagata    60
agttaaaagt ggggtgtcca aaatttatg aattgaattg acagttatt cagatcctga   120
aaatacgctt ctctgatcac tgcaaatatt cccgataaat aagtgaacat taggttaatc   180
ttaattttcc cttaactttc cttagccttt tttaaatttt tggattattc aagcattttt   240
attgcggtat cgttttgta aaaaaaaag tataattcaa cattcaggct cgacgttatg    300
```

<210> SEQ ID NO 65
<211> LENGTH: 300
<212> TYPE: DNA
<213> ORGANISM: Dirofilaria immitis

<400> SEQUENCE: 65

```
aattaataaa agaaaggaa tacgataaaa tatctattt ttgaaactaa tcaaacatat    60
tcctcactgc tcaccggata gttgctttct aattttacat taagaaatat atttttttt   120
ttcaataagg aaagttatgc agactaggag aattctactc tgaagaagag ataagcatgt   180
tagaattatt aaaatctatg gaaatatcct taaaagaatg cctatagtag ctctgatttc   240
gaaaaaaaaa gcaaaaaaca aaataacaaa ttctgctcaa ttgaaataaa aaactttcct   300
```

<210> SEQ ID NO 66
<211> LENGTH: 300
<212> TYPE: DNA
<213> ORGANISM: Dirofilaria immitis

<400> SEQUENCE: 66

```
taaaatatct attttttgaa actaatcaaa catattcctc actgctcacc ggatagttgc    60
tttctaattt tacattaaga aatatatttt ttttttttcaa taaggaaagt tatgcagact   120
aggagcattc tactctgaag aagagataag tatgttagaa ttattaaaat ctatggaaat   180
atccttaaaa gaatgcctat agtagctctg atttcgaaaa aaaagcaaa aacaaaata   240
acaaattctg ctcaattgaa ataaaaaact tccttcaac ttccagcatc actgctgtga   300
```

<210> SEQ ID NO 67
<211> LENGTH: 300
<212> TYPE: DNA
<213> ORGANISM: Dirofilaria immitis

<400> SEQUENCE: 67

```
aactgctaaa aaattgaaac tagtgttaga ttgataagtg ggcagattaa aaccaattgt    60
gttattggcc cgttaattag tgactctgaa tagctatggc gaatcgtata gtgttgtacc   120
gacgacgtat ctatcaaatg tctgccttgt taaatttcga tgatagttta tgtgcctatt   180
```

```
atagttgtaa cgagtaacgg agaataaggt ttcgactccg gagagggagc ctgagttgcc    240
acattcaagg aaggaagcag tcgcgaagat tacccactct tagaatgagg aaagagtgac    300
```

<210> SEQ ID NO 68
<211> LENGTH: 300
<212> TYPE: DNA
<213> ORGANISM: Dirofilaria immitis

<400> SEQUENCE: 68

```
gaaaactaag aagtaagtga aatttctaag ttctttccca gaaaggttag atccaatatt    60
tgttttcatt ttagcatttt tatccaatga aaaatgtgcc caataaatac ttgtatatag    120
tattgcattt aaaaacttca gaaagcacaa tgagatctaa gctcagaaat atgacgaata    180
ccaatccttt tcctagtctt accgcttctt aactttgtg tcgctttata aaaattaaaa    240
ataaaaagtt gaacaatggg aattacatca ttttcatctg aatggtttat ttcctattct    300
```

<210> SEQ ID NO 69
<211> LENGTH: 300
<212> TYPE: DNA
<213> ORGANISM: Dirofilaria immitis
<220> FEATURE:
<221> NAME/KEY: misc_feature
<222> LOCATION: (36)..(45)
<223> OTHER INFORMATION: n is a, c, g, or t

<400> SEQUENCE: 69

```
cttccctagc tatgcctttt cgtcacttaa gcttcnnnnn nnnnntctag ctacgtatcg    60
ttatcattta tgcttcttta gctacgtttc tccatcattt atgcttccta agctacgtat    120
cttcatcact tacgcttccc tagctatgtc ctttcgtcac ttaagcttct ttggctgcgt    180
gtcttcatca ttaatcttct ttagctacgt atcgttatca tttacgcttc cttagctacg    240
tctttccatc atttatgctt cccaagctac gtattttcat catttatgct tccttagata    300
```

<210> SEQ ID NO 70
<211> LENGTH: 300
<212> TYPE: DNA
<213> ORGANISM: Dirofilaria immitis

<400> SEQUENCE: 70

```
gatcttaaaa ttctatgaaa cttcttctgc atggtattgt ttccaacaga atataatgac    60
aatagcaaca gtattggtta tataaaaata ttgactgcag caggattata tttcaagttc    120
ttttaatttc atttatttat tctttcattt acttttactg tttttatgtt tttcttcttt    180
aaaaaatatg atttctctca ctgttctctt tcatctatct atatttattt gataattgct    240
tatatgataa ctagctaaag ggaaataaac tttcagtcat catagcttca ttttagtaaa    300
```

<210> SEQ ID NO 71
<211> LENGTH: 300
<212> TYPE: DNA
<213> ORGANISM: Dirofilaria immitis

<400> SEQUENCE: 71

```
ctatactaat cagtccacta tccattttta ggttgcaaaa gttgcaatga cggtttgatt    60
tcatcctcca atgcaatttt gagtctcaat ctcgagagat agatcgatcg cttttagctt    120
gatttagctt ggttaatgtt gtgagggata ttgggcagaa attctgtcaa gcgttactta    180
atgaaatagt aaatgatcac tgatatttat tgttaatgat acttgagctc tctagattat    240
```
gaactggaag gttttcgata gaaataatcg atacatatat tagaatcgac ttcttttttc    300

<210> SEQ ID NO 72
<211> LENGTH: 300
<212> TYPE: DNA
<213> ORGANISM: Dirofilaria immitis

<400> SEQUENCE: 72
tcatcttttt cacatttcat ttaatcatca ttttatcaat tcctattttt aaacaaattc     60
ttttcaaata ttctctcttt ccttctcttt ttgttttccg cttattcatt ctaatgatga    120
acagatgtag aaaatttgca ttctattgct cactacaatt ttgagtagaa tatatttaat    180
tatttgattc gagacagatg gttatagcct ttagcttcag cttctcgttc aaattaagta    240
cttgtgacct ttccaagtac cattaaagct ttcctgcgtt tcctaattag aaaaaaaagg    300

<210> SEQ ID NO 73
<211> LENGTH: 300
<212> TYPE: DNA
<213> ORGANISM: Dirofilaria immitis

<400> SEQUENCE: 73
gcattttaag ttaaaagtat cacgctgcat gacacctcac gtttgctatc tcaaattgag     60
taggttagaa tctttttttg gctactattc aaatattaat aataaattgc tgcaaacaga    120
tttcacaccg gaaaaaaatt aaattttttct agcaatgttt taactccctt attaaatatt   180
tatagaaaat cgactactta aaaagaattg actaacattt ctgaatctct gcagagattt    240
atagatggat tagcatccta caagttttta tcttttttgct atatttccat tattttttta   300

<210> SEQ ID NO 74
<211> LENGTH: 300
<212> TYPE: DNA
<213> ORGANISM: Dirofilaria immitis

<400> SEQUENCE: 74
gataagacgt cttattttgt aataattcaa aaattaatta atatagaagt aagatcttga     60
taataattaa tatgctcaaa tttcttaatg agaaatatgtt caggatgaag atgaagtgaa   120
agaaattgat agattgagga agcaattgct aattgaaaca gaacagctcg tttccaattc    180
tcttaaagat ttactgaaga aaatttatta tccacttgaa gaagctattg atctcaaaat    240
tcatcagaaa ttaattcaac aaattgctgc cttgttgaag tgtattagta tcttggataa    300

<210> SEQ ID NO 75
<211> LENGTH: 300
<212> TYPE: DNA
<213> ORGANISM: Dirofilaria immitis

<400> SEQUENCE: 75
accgcaaaat acctaaaaat ttctataaca acgattaaca cggcctcgaa ctggaagcat     60
attaatccat gcgtggctca aacttcaatc ataaagacaa gatctagaga tcaacacaaa    120
atggtgaatt gttaccctat cgttgctaaa gtttgagaga aaaagtgct aaatcaagta     180 gtacaccaaa tttagttaat attaagaaat caatttagta ctgaatttaa acaaatgaaa    240
ttttacgata aaataaaaaa gtacctgatc aaacagcgtc ctcccgttat tcccattgct    300

<210> SEQ ID NO 76
<211> LENGTH: 300
<212> TYPE: DNA
<213> ORGANISM: Dirofilaria immitis

<400> SEQUENCE: 76

```
tataagacta gtaaacagat cgtaatataa taaatatcga ttttatttta aattttcgaa      60
aacttccaaa tctatcgata tgaaattaaa gatcaatttt taatttccat aatatattta     120
gattctatcc caacatcact catcttatg tcaacttatt taattctctt attaacatta     180
tatttcttgt ttacaatgat aaattttatc aattttctaa tatgatagaa catcttcatc     240
atctgaagat atgcttttct catctttgta acaattcgta tcgcttctga ttttactttc     300
```

<210> SEQ ID NO 77
<211> LENGTH: 300
<212> TYPE: DNA
<213> ORGANISM: Dirofilaria immitis

<400> SEQUENCE: 77

```
gttttattat tgcttattga atagtgataa taacactttg atatgatatt gttttgttgc      60
gatcattgta ttgattataa ccttaattaa acgaggatat tatgggaaat gtatttatta     120
caaaattaaa tatgaaaggt tgaagtcttg acgaaacttt caaacacatt tctcgaattt     180
tctctgcaaa aatatcgtta cgattttttgg aaattatgaa gtccaagaat tcaatcgaga     240
gttcgccatg tcactttggc tagtttcgtt tgttttttaat atttcaatca aaagtcaatt     300
```

<210> SEQ ID NO 78
<211> LENGTH: 300
<212> TYPE: DNA
<213> ORGANISM: Dirofilaria immitis

<400> SEQUENCE: 78

```
ccttggatat tgttcttgac atcgttgatc agaaggtcac cgtagtgttc ggtgagcgag      60
atggaattgg actcaggttt attctccgtt tttttcatgt ttttgaattt tagagagaaa     120
ataatgtttg tctgaatggt tagcaaacta attagttttt aagttatcag gaactcgaag     180
tatcttcttt tgcacttctt taacctttt catcaaattt tttaacagta acaagatttt     240
tttgagaatt ttcaaaatat ttttgacttc tgatgatatt tgatgagaaa accatcactg     300
```

<210> SEQ ID NO 79
<211> LENGTH: 300
<212> TYPE: DNA
<213> ORGANISM: Dirofilaria immitis

<400> SEQUENCE: 79

```
agagtattat tatacatgat gatgatgatg atgatgatga tgatgatgat gatgatatga      60
tgatgatgat gatgatgatg atatgatgat gatgatgata atgataatga tgatgatgat     120
gattaattgc ttattttaa tgattgataa ctttaaaaga aatcattgaa atttgatcga     180
ataaaattt tcttaaaaaa agcatttgct atttatatag taaacctata aaaaattact     240
tattttatt actaatattc atttgattgt atgaaagaga agagaaaaaa aacctttgca     300
```

<210> SEQ ID NO 80
<211> LENGTH: 300
<212> TYPE: DNA
<213> ORGANISM: Dirofilaria immitis

<400> SEQUENCE: 80

```
tggtatcaca gcactgggtt taatttcaac aatcggttga cgatcttttc gggatatgcc      60
tatacccaga aatgaacgta tgccaaacga tggtatgttt gatgcaacag acgacgtcaa     120
```

-continued

| | |
|---|---|
| cttaaaatgt gtttttttt caaaaattca atatttttag tttaaaattg cacgtcagta | 180 |
| aaaattaatt cataataaat ctctttgatt tcttcgttct cctttttttt cagaaaaaat | 240 |
| tgaaattta catacctgat ttccaagagc atataaagca tcacttaaag cattctgcga | 300 |

<210> SEQ ID NO 81
<211> LENGTH: 300
<212> TYPE: DNA
<213> ORGANISM: Dirofilaria immitis
<220> FEATURE:
<221> NAME/KEY: misc_feature
<222> LOCATION: (263)..(272)
<223> OTHER INFORMATION: n is a, c, g, or t

<400> SEQUENCE: 81

| | |
|---|---|
| tccttttcat gatttgtagc taaccaataa gatgtgtata tgttcatata tttactctcc | 60 |
| cctgactctt ttacactctc attctctcat ttgttcattt agataagtaa tatgcgcctt | 120 |
| tctcttcctg attctctcaa tctttcatcc cttcatctcc tcaatctttc tcccattctc | 180 |
| tcaatctttc ctgcattgca ttcattgatg aaacacgata gtattaataa gcataatttg | 240 |
| ataaattgaa ataatttttt ttnnnnnnnn nntcattctc tcaatctttc ctgcattgca | 300 |

<210> SEQ ID NO 82
<211> LENGTH: 300
<212> TYPE: DNA
<213> ORGANISM: Dirofilaria immitis

<400> SEQUENCE: 82

| | |
|---|---|
| tttgaattaa caaatatta acaattacaa ctatttcgga atttaattta agaataatttt | 60 |
| aattaatcaa tttcctatttt tgtatttaa aaattaccac aataattatg taattttgg | 120 |
| gatatttgaa actttgaaaa aagtggtatt gtatttgaga ataaattaat taatgtaatt | 180 |
| cttgctgctc atcgttccat aacttacaaa tatttctcgg tatttatttt gagataattc | 240 |
| ttatcatttc ttccatagct ttcaatatat ttataactta tttgtaatca ctcttatcac | 300 |

<210> SEQ ID NO 83
<211> LENGTH: 300
<212> TYPE: DNA
<213> ORGANISM: Dirofilaria immitis

<400> SEQUENCE: 83

| | |
|---|---|
| ttgagatatc aaatcaagcg ttgcatattt atagtacact ggtgtagctg aaatcgcgaa | 60 |
| gagaacacga aaatcagaga agtcaatggt tcctttgtgt tggatttcac atgaaagcat | 120 |
| ccttatgttg tacatgcgtg attacaatat gatacaagat gtaagctaaa aattgtttta | 180 |
| tctttgtcta tgagatgtag ttcatactct ataataaagt cccaaccctt aattctcata | 240 |
| ttcacaaccg tatcagaatc caacaccaaa ccattataaa gaatgttctt cgtcgaggcg | 300 |

<210> SEQ ID NO 84
<211> LENGTH: 300
<212> TYPE: DNA
<213> ORGANISM: Dirofilaria immitis

<400> SEQUENCE: 84

| | |
|---|---|
| ccactatcgc ttacactttc tttatcctgt tcttcttcat ctttcgttttt ggactttatt | 60 |
| ttactgtcag gtgacaagca aagtaacgat gttggactttt gcgaagatgt ggatggtacg | 120 |
| ctagaaaaaa aatgaggatt ggttaatatg tctaattatt acatcgcttt ttttttaaatc | 180 |
| ttttctaaaa ttaaactgaa taatcaactt atttgctatt cagtttatct tattttttat | 240 |

```
caacaaaatt cgaggaaaca aatcgcttat cagaataatt gttttgatca acaaataaag    300
```

<210> SEQ ID NO 85
<211> LENGTH: 300
<212> TYPE: DNA
<213> ORGANISM: Dirofilaria immitis

<400> SEQUENCE: 85

```
caatcccaca aattcagtgt gtcggcgggt cagcgaaggg aaagtttgaa ccgagggtat    60
gtacaaattg tgataatttt gtgatgacgt agtaaatttc atagttttgc atgctttaat    120
gttgatagtc gcacaatcct acgttgatta aatttagcta ttagatatcc tactaaatta    180
tgttgttcat aattttttgtt tttaaaatgc tccacttata ttttcaggtt gtgcagtgct    240
acaatagggg ttatgacggc aatgatgtcc aatgggagtg taaagcggaa atgagcaatc    300
```

<210> SEQ ID NO 86
<211> LENGTH: 300
<212> TYPE: DNA
<213> ORGANISM: Dirofilaria immitis

<400> SEQUENCE: 86

```
tcagataaat tgtatttgat gttaattcaa agaagaaaaa aataatcagt agaatatgaa    60
tcgaataata ttcatacaac cagtttattc attattattc acttttaacg tctaaatgac    120
gtagctacgc ttttttttctc gctttcaagc ctttactgac caagattaat gtacattctg    180
ttgaacaaga ttaatcgaca ttctatcgat caagatcaag cttttactga tcaagattaa    240
taatgacatt cttctgttga tcaagattaa tcgacattcc attgatcaag attaatcgac    300
```

<210> SEQ ID NO 87
<211> LENGTH: 300
<212> TYPE: DNA
<213> ORGANISM: Dirofilaria immitis

<400> SEQUENCE: 87

```
ctctctaaaa cctattggtc actaaacttg cactgactaa aaactattgg tcatcagact    60
tgtgattcat tgaaaagacc gttagccgct aaaattatga ttcactaaaa aaatctatt    120
gatcattaaa tctgtaatca ttgagaaact acaatcattg gtcattaagt ttgtgctctc    180
taaaacctat tggtcattaa actgactaaa aactattggt cactgaacct agagtctatt    240
aaaaaaaaaa tcattgtatc aataaattta ttgtttacta tcaaatccat tgattactga    300
```

<210> SEQ ID NO 88
<211> LENGTH: 300
<212> TYPE: DNA
<213> ORGANISM: Dirofilaria immitis

<400> SEQUENCE: 88

```
tctaaaacct attggtcact aaacttgcac tgactaaaaa ctattggtca tcagacttgt    60
gattcattga aaagaccgtt agccgctaaa attatgattc actaaaaaaa atctattgat    120
cattaaatct gtaatcattg agaaactgca ttcattggtc attaagtttg tgctctctaa    180
aacctattgg tcattaaact gactaaaaac tattggtcac tgaacctaga gtctattaaa    240
aaaaaaatca ttgtatcaat aaatttattg tttactatca aatccattga ttactgaata    300
```

<210> SEQ ID NO 89
<211> LENGTH: 300
<212> TYPE: DNA

<213> ORGANISM: Dirofilaria immitis

<400> SEQUENCE: 89

```
aaaatgtatc aaattcttcg atgccataaa ttatacagac ttgattggca ttttttctaa    60
ctttcatcat gaaccattct atttctaaat tgatccatta caaaatcaac tttgtgatat   120
catcaatctc agtcataacg agaaataatg ataatataaa gcgactatca tttgaatttc   180
ctgaatattc aagatgtaat tacatctttt ttttaatgta atcaaaattt cttgccatca   240
ataattttc aacatatgct ttcatcgact gccttatgca gatcgtaatg atgacagcca   300
```

<210> SEQ ID NO 90
<211> LENGTH: 300
<212> TYPE: DNA
<213> ORGANISM: Dirofilaria immitis

<400> SEQUENCE: 90

```
attgattaaa aagaatcaac attaaatttt tgatatagtc gagaaatcct tcgtgataat    60
tcttttagaa caattcttta cactaaactt gtatttactt gcttattatt tgtctaaaga   120
tactaactat tgtcagtgg aatttatgat cttggcatta ttgcatataa cgctttccta   180
aaatctgaaa ttttcagta ttttaaaaac taagacgatt attaaatatt actcaaagct   240
tagaactttg attatactaa tcaaatcaaa aatttcatca gcgattttg ttgtgtcatt   300
```

<210> SEQ ID NO 91
<211> LENGTH: 300
<212> TYPE: DNA
<213> ORGANISM: Dirofilaria immitis

<400> SEQUENCE: 91

```
atttttcca gcagaattgt catcaaaaat cccatttttg atatcctctt catcgaaact    60
tgctcctgaa tccagagaac aacgaagaat gtgtaaatct atttcagtag cctgctcatt   120
gtgcaattca gcgactttat ttctgtgctt caagctaact tcttcattat gccactcctc   180
ttctctcgct attttttcgc tatctaattc aaaatcttcg tctgaaacgg aatcaactcc   240
tgacgatgta ctcgacactg ataatatttt catgccgatt tttctctcaa acgaatcttt   300
```

<210> SEQ ID NO 92
<211> LENGTH: 300
<212> TYPE: DNA
<213> ORGANISM: Dirofilaria immitis

<400> SEQUENCE: 92

```
gaatgaagag caaaaaaata gtcacgacca cctgcaataa aaacagcatc tccgtaaaaa    60
tgattgaatt gattcccgaa atacgagttt atcaaattga gaattatgca aattaattat   120
cagcatgcag atttactgat tttatatctc tcataccgaa attaaggtga tgttttccat   180
ttctttgttt ccacaatgtc ttctttgtga atcgttttgg atcaactatt aatccgatcg   240
aatcaatcct ccaaatatga gtttattcaa cgtaacaaaa cattgtccga gataatcaaa   300
```

<210> SEQ ID NO 93
<211> LENGTH: 300
<212> TYPE: DNA
<213> ORGANISM: Dirofilaria immitis

<400> SEQUENCE: 93

```
tggaaatttc gaaatcgaaa ggatgaagaa aaaggatcct tgatctatac attaaatatc    60
accatatcaa ctagcatggc aagtcaaagt aatgttatca tttaaataaa aaagatgaat   120
```

```
agtaggacta caggttatat tgttaaaagt cgacaaattt ggagtaattg acagagatca    180
acgattaaat gtaatggatg atcttatctt ctttttcaa ctacgccaaa atgaaaataa    240
caattgaatt tgtcgaataa gaaactaaca ttttgaaaat aagattgaac atttataaat   300
```

<210> SEQ ID NO 94
<211> LENGTH: 300
<212> TYPE: DNA
<213> ORGANISM: Dirofilaria immitis

<400> SEQUENCE: 94

```
ggttggatca ttatcgacag aactttagaa gtttcttgat aaggacgaaa agaagcagca    60
ccattgctga tctaaacaag gaaaaaagac ctttttgga atattgaagt ttttactgat    120
aggtgcgtgc tgtgtactgt gggcataagt acaagcttca tgctccgcag cgtgaatacg   180
tgctgcatgc atactatgca gtaaaggtgc gtgtcgtatt gctcaataag tgtataaatt   240
gctgcttttc ttgcatagtt aaatattttg ttttcatttt ttccgctatt caaaataaat   300
```

<210> SEQ ID NO 95
<211> LENGTH: 300
<212> TYPE: DNA
<213> ORGANISM: Dirofilaria immitis

<400> SEQUENCE: 95

```
gttgggattt cagactctca ctcggtgtcg tttcacagtg atatctgaat cgaagtcaca    60
agcaggtatg aatgcataac aactaatatc cattgcagaa acaaggcaaa actgagaagc   120
tcgagcaata tagctataga agctggtacc acagatgaca ttacatggta tttccatttc   180
agcttcacaa acattgtaaa tagcttgctt cgatgattca atatctcgtt ctacgatatt   240
cttaaagtaa tttttattta tttgaagtat agattacatc catgttctat ctatcatttc   300
```

<210> SEQ ID NO 96
<211> LENGTH: 300
<212> TYPE: DNA
<213> ORGANISM: Dirofilaria immitis

<400> SEQUENCE: 96

```
tgttctgaac atctctttt gattatcttt tttaattcct ccattatttt cgttttttc     60 gttgtgaatt aatattgttt gtctttgatt cagatgatat tttcggatcg taaatagatg   120
gcatcggcat aagcgtattg agaagcattc aatggtgcac tcttgcttct ttttttttg   180 aaatctttct cgataatcaa ataagtgcag gatgccaatc attaacaatt tcgttccact   240
ttttcagttc ttattcttat aacaccacat ctcatttgca attttgtcgc caatgatttt   300
```

<210> SEQ ID NO 97
<211> LENGTH: 300
<212> TYPE: DNA
<213> ORGANISM: Dirofilaria immitis

<400> SEQUENCE: 97

```
tttttcgag gtcactctgg aaaaataaat catattttaa aaagacataa ataaaaaat     60 atgtatatat aagaaaattt ttactctgaa tttcttaaga aaattctcga ttctgttttc   120
cataaattcc ggaatatgtt gtccctgaat taagaattcg attccttgca caccattatt   180
tcgtctagtt cctgtgtgaa caatgtaacc tggaaatgaa cacataaact gtaatatttt   240
gagcttaaaa taattatgag gatgcgaaac tgaagatatt cataaatgtt taaaaaaaaa   300
```

<210> SEQ ID NO 98
<211> LENGTH: 300
<212> TYPE: DNA
<213> ORGANISM: Dirofilaria immitis

<400> SEQUENCE: 98

| | | | | | | |
|---|---|---|---|---|---|---|
| gtccatgcat | tgcttttcgg | aagttagtgt | agattcagtg | aatatttaat | accagtctct | 60 |
| ttctaattca | aaagagcctc | ccatttcttt | tttcagtttc | agtctctgaa | tcagagcgtg | 120 |
| taatctacca | ctccattgcc | gaaaacagct | cgatgtattt | cctgctacgt | agtgtttaga | 180 |
| attggcgtat | gccacttgct | cattattcgc | gcatgaagtg | taactgtgaa | tagaatgata | 240 |
| ctactgttag | aagagaatgc | gttcactttta | tttaacatta | tactgattca | tttcttcttt | 300 |

<210> SEQ ID NO 99
<211> LENGTH: 300
<212> TYPE: DNA
<213> ORGANISM: Dirofilaria immitis

<400> SEQUENCE: 99

| | | | | | | |
|---|---|---|---|---|---|---|
| agtgaacgag | aaaaaacaga | agaagagata | gcacatcaag | atcgtgagaa | attaattaga | 60 |
| caagaaaaag | ctcgtcttac | acaaatatat | caggttttct | ttttcttgct | ttcgaaagtt | 120 |
| atttgaatta | tctcatttct | ttgaattta | taagaaataa | tttaattttt | ttttgaaatt | 180 |
| ttgcctattg | agctctaaat | tttgtaaaaa | gttttctagg | atgatgttag | caaagcaaaa | 240 |
| aagaaatcca | aaagtgatgg | taacaaacag | gaagatttta | tagtgaggta | cgataatacg | 300 |

<210> SEQ ID NO 100
<211> LENGTH: 300
<212> TYPE: DNA
<213> ORGANISM: Dirofilaria immitis

<400> SEQUENCE: 100

| | | | | | | |
|---|---|---|---|---|---|---|
| tagacaatat | catccttcct | tttttttgc | tcaatttctc | tgctcattgc | tttgatgata | 60 |
| atggtaggtg | gtataatgaa | acgaatagat | aattgatgtt | cgcaaacatt | tgctgttaaa | 120 |
| tttcagtaaa | gaaattgacc | ttttttgcttt | gtgttggatg | tttagcttca | ttttcttctt | 180 |
| gttcattgtc | atattcattc | tctcaaaact | tcttgcttag | cgatgctaat | ataaatactg | 240 |
| gaagaatgcc | tttgctttgt | tttagttgta | aatcatcacc | aaggtatttt | tttgcaaaat | 300 |

<210> SEQ ID NO 101
<211> LENGTH: 300
<212> TYPE: DNA
<213> ORGANISM: Dirofilaria immitis

<400> SEQUENCE: 101

| | | | | | | |
|---|---|---|---|---|---|---|
| aagatgaaac | taaaaaaaat | tatttcgaaa | aaagaaaat | aaaattaatg | aaataaaagc | 60 |
| aaaaatgaac | aaaccgtatt | aattttaaac | aataaacaat | atcgaaatcg | aaaaatggac | 120 |
| tattattgat | gaactatatt | ttcaaaatgt | gaaaggtcaa | agtttgtttc | aattatgata | 180 |
| aatacaattt | aaaataagat | taagctaaca | aataagttga | gcaaattgat | gaaacaaaca | 240 |
| aatcagaata | tattacagaa | aatgatataa | catgaaaata | tattagacca | attatttta | 300 |

<210> SEQ ID NO 102
<211> LENGTH: 300
<212> TYPE: DNA
<213> ORGANISM: Dirofilaria immitis

<400> SEQUENCE: 102

```
ttgaagtttt cagataaact ttgataaaaa attgttctat gaattctcaa atttcaatta      60
gtgatactta tttcgaaggt aattatgcct gattgaatct tcaatatcaa caaaatgaaa     120
attttagtat gattgttaac tcatacacct ctaattaaag gtattttctt tatcccatga     180
aatgaaaatt tattaagaac ttagaaagct acggtatgcc tttgatgcaa aagaaagatt     240
cattttcatt aaatcatgtt taaaaaaaag agcaaagagc aaaggtgat gaaagttttt      300
```

<210> SEQ ID NO 103
<211> LENGTH: 300
<212> TYPE: DNA
<213> ORGANISM: Dirofilaria immitis

<400> SEQUENCE: 103

```
ttctatacga aatatttgtc tgccataaat ctactcagga actcgataca tcaaaacata      60
agtacgcttg ctctttattt ttcgtttgaa aaataaatag atcatttttcg cacttacatt    120 tcaatttcaa ttgctttatt catatctttc tgtttttact tactggtatt taacagtcgt     180
tgttcacaat ttaatgatct atgaaacacc atttaattgt atttggacta acttttcgac     240
aagcaaaaga ttaaaattgt cttcagatac agttataaat ttacattgaa gataaatgaa     300
```

<210> SEQ ID NO 104
<211> LENGTH: 300
<212> TYPE: DNA
<213> ORGANISM: Dirofilaria immitis

<400> SEQUENCE: 104

```
taacgatctg tatatcaatg gaataatatt cagttcatgt tgtactcgat atgagataga      60
attacaattt tggaacaaga taatctcaac agctattttc aagaatagtt aaattaggat     120
accattcaaa gaaactttaa aaaatgattt ccatacatta atgctttttg tgttttcgct     180
ctcgaccaga atccaggaat tgtccattat catcaatttg attaactttt atctttattc     240
taattcttca acatttctct aattgatatt agtttcaata ttttaataag taaaaattta     300
```

<210> SEQ ID NO 105
<211> LENGTH: 300
<212> TYPE: DNA
<213> ORGANISM: Dirofilaria immitis

<400> SEQUENCE: 105

```
ataatgtgtt attgatcaaa ggattttttag ttacctacca gatggaaaaa aagcaagttt     60
acgaaaacag aagttagcat caactttcat ccatggttac accgtatata atccaatcga    120
ctcatacttt atgttgatct gattttatag cagataacta gttaccttgc tcagcagcag    180
ctaaatcctt tctatttgct taataacaga aatattttc attaacaaag aaattatact     240
ccgtgtttga catttcattt taatttcgtt ccaaaaatga aaaagcttc gtccggaaat      300
```

<210> SEQ ID NO 106
<211> LENGTH: 300
<212> TYPE: DNA
<213> ORGANISM: Dirofilaria immitis

<400> SEQUENCE: 106

```
attattttgt agttttcat ttttagttc aattttcctt tgcttatttt aaatatgcca       60
ttctttattc agactcatag cgaatgcata tgttcattaa tttttttagt tacagttaca    120
aattctcaat ttctctttaa tcatttttt ttccaaaaat agtctgagca ctcaaccatt    180
```
cattcaacaa ttgcagcttt ttttattgga gccttgtcaa attatcaatt cgtttccatg    240
tttattattg aaataataaa cggtatttag gataacgaag ttcgcttagc ttctttgact    300

<210> SEQ ID NO 107
<211> LENGTH: 300
<212> TYPE: DNA
<213> ORGANISM: Dirofilaria immitis

<400> SEQUENCE: 107
aaaaattcag gtaatgagat cagtaatttt ttttggtcac tttgctgttt cttatcagct     60
cattgttatc catatcaaat gagcgaaagt gtgtatcaca tattggcaga gtgtaatcta    120
tgaagatttt gcgtatcaaa gtaattatga gagaactgat aattttattt taaagtagta    180
gaaaactcga attaagctaa taaataatcg gttgatatcc atgaaatgaa ttactaatga    240
aatggataat tgagtaataa caaatgatat tcatgaagaa aggcaggttt ttttaatag    300

<210> SEQ ID NO 108
<211> LENGTH: 300
<212> TYPE: DNA
<213> ORGANISM: Dirofilaria immitis

<400> SEQUENCE: 108
tatacttaaa acaagaaata caattaatgc caatagcaga gtgaaacttc tgaaaaataa     60
tgagttgaaa ctggtaaaat taacatttta ttagaaattt cagaaactta tgactcctca    120
tggcactatc acaaaatgtt tgaaaaaaat tgacagctcg cgtcgattgc aaaaatcatg    180
attcctgata tttagtatcg aacatgtgac aaataatata aagacctaac cataaagcac    240
tgaaacaact cgcggaaaca aaaaattaat ttgcataaac acggaatacg atcagaaaat    300

<210> SEQ ID NO 109
<211> LENGTH: 300
<212> TYPE: DNA
<213> ORGANISM: Dirofilaria immitis

<400> SEQUENCE: 109
gaattttttt agaaggcttg aagtcgagaa tattagagac tatatcgaag acttaaataa     60
tcctggtaat cttctgtatg aatcaaaatt acctcgaaca gaaccattca gcacatcacg    120
agataattca tggaatgaaa ctagccaatc agagcgttgt aaaagaagaa agttatgaaa    180
tgaccttaaa atcaatttaa agcatgtcct cgccatataa gcgttgaaaa gttaggatag    240
aatcaattat caaaaaaata tgttaactag atcttatcaa tcaaaacatc agaaggaaaa    300

<210> SEQ ID NO 110
<211> LENGTH: 300
<212> TYPE: DNA
<213> ORGANISM: Dirofilaria immitis

<400> SEQUENCE: 110
atatgataat agtgaaacaa ttccatcaca ataaatatta tcgattagga gataaattaa     60
cattgatgcc tcaattttgg tcaacaatat atatttgcta ttagcatttt tattaaatcg    120
tttttatctg acttgacata aattgaaata gaaaaaattg aatctgttcc ttgttagatt    180
ttcttctaaa aattcttgaa atacaaataa tttcttaaat ttcaatattt ctacataatg    240
tattgcgaca aaaatgctaa tgattggctt attattattt cgaataattt tttaatcaaa    300

<210> SEQ ID NO 111
<211> LENGTH: 300

<212> TYPE: DNA
<213> ORGANISM: Dirofilaria immitis

<400> SEQUENCE: 111

```
agctcgaaga tcggacaaaa tttgttcagc ttgttgcctt gaggctttag tctgaaaaga    60
cacttaaaag tataaacaaa ttatattcaa aaaatcttat tttgcatttg cgtcttaatt   120
tttgcttttt gcaaagtttt ttccgagcaa gttttctat cttcgaaaag attatatcaa   180
ttaaaatttc aatttaagca atcattgcct cttcgagttt ctgtttcagc aaataaatat   240
caccaccacg acgctgtcgg aagaaagaaa cgcctttccc aatttctcgt ctcaacttt    300
```

<210> SEQ ID NO 112
<211> LENGTH: 300
<212> TYPE: DNA
<213> ORGANISM: Dirofilaria immitis

<400> SEQUENCE: 112

```
taagaaagct gggagatttt ccaaaaacac tatttcccac gatttgttgt tttctatgat    60
caattcttaa tcaaactctg aaattctcaa attttcgatt tctatccaac ttctacatat   120
ttttttagaa aattcatatt tagcaaagct gagtgtagaa ataattcata cttgcaattc   180
attttctta aattttcgaa tttcttaaaa aagtatttca aattacctac caattttgat   240
tggaaaattc gtggatgcta aaaattcaaa tcaaaatagt taaacagtat tcctaattgt   300
```

<210> SEQ ID NO 113
<211> LENGTH: 300
<212> TYPE: DNA
<213> ORGANISM: Dirofilaria immitis

<400> SEQUENCE: 113

```
aatttaaaaa acacatcgac attttgcggt acggtaatga ttgtttacag taactaaatg    60
tgtcctacgg tagtaatact cgtgtacgta atgaatgagt atagtgaccg gatatttcct   120
tcactagtag gcaatattaa gaagtatttt cattttcata ttctatctaa aataaaccga   180
taaaatggtt tttgaattat tactttttca ttgttatttt ttgatcctaa attgtaaaat   240
actgtaataa tttagctaat ttctatgatt ctattcaata tgcttaaatt aaaattctaa   300
```

<210> SEQ ID NO 114
<211> LENGTH: 300
<212> TYPE: DNA
<213> ORGANISM: Dirofilaria immitis
<220> FEATURE:
<221> NAME/KEY: misc_feature
<222> LOCATION: (63)..(72)
<223> OTHER INFORMATION: n is a, c, g, or t

<400> SEQUENCE: 114

```
tcgtatttgt tgtatgtaat atagaaatat tgtttaaatt caatatgtag aaaaaatttc    60
tannnnnnnn nnaattaatt acatattaac tcgtatttgt tgtatgtaat atagaaatat   120
tgtttaaatt caatatgtag aaaaaatttc cataataaag acgaacagca tttataatta   180
tcaatgataa gttgaaatta attcatcaat gataagttga aattaattta tttgaaataa   240
tttcttgaa attcgaatat agacgagaat tttttttttt ttgctaatcg tttatcaaat   300
```

<210> SEQ ID NO 115
<211> LENGTH: 300
<212> TYPE: DNA
<213> ORGANISM: Dirofilaria immitis

<400> SEQUENCE: 115
tctagcaata taaattacaa gaatatgccg tccaagtatt tcagaattta ttattaattt    60
ggataataat acattgtaaa tactgcgtat tctggattat tatgcactgc ataataacat   120
gcaatttcgt ctacatatcg cgaataaacg ccaaaagatt tctcgataaa agaaaatata   180
agaattcgta aatgaatgtt gtgtcagaga tatgtgttaa ttcataagtc aagatgttgt   240
aaatcgatcc atattagtaa tcatatttac gtgctcgtaa ataaaagcgg tgattcttgt   300

<210> SEQ ID NO 116
<211> LENGTH: 300
<212> TYPE: DNA
<213> ORGANISM: Dirofilaria immitis

<400> SEQUENCE: 116
atcgaaaaaa gatgatctga tgacggaagg cgaaatgtct gcagaagcta agatgacgga    60
agaaaaaagt gaagaaatga agaagaagc tggtaaaact cagaaggaat gtaaaactgg   120
agaatcgaaa aagatgatc tgatgacgga gggcgaaatg tctaaagaag ctaagatgtc   180
ggaagaaaaa agtgaagaaa tgaaagaaga agctgataaa actcagaagg aatgtaaaac   240
ggaagaatcg aaaaaagacg atctgacgac agaaggcgaa aaatctgaag tagatgagcc   300

<210> SEQ ID NO 117
<211> LENGTH: 300
<212> TYPE: DNA
<213> ORGANISM: Dirofilaria immitis

<400> SEQUENCE: 117
actaatgata agaaacggag ccgacgattt taggaaatga ataataacga cattgacaac    60
cattgttaga aaattgatag tactgataat aaaagctagt tatagaaaat tgataataat   120
aataaaattg ctggtagcaa atgtctagaa gtgataataa aattaatgat agcaaatgga   180
ttagcaatga taattaaact gatgatagcg aatggattag taatgataat aaaattgatg   240
atagcaaatg actaataatg gtaataaaag ttaatgctag tgataacttg tattttaagt   300

<210> SEQ ID NO 118
<211> LENGTH: 300
<212> TYPE: DNA
<213> ORGANISM: Dirofilaria immitis

<400> SEQUENCE: 118
acagtttata gttacaatat tctccggtga ctaactgtat tttacaactt ataattatag    60
attacaaaat atattatagt agttttataa ttacagtatt cttaagtgaa taactatact   120
ttacagctta cagttacagt agttttctat gttttttgaat attaattta catggttttt   180 cctagtttca gtttcaaaat tttcagatat tttatgtgtt aaagcaaatt atattcgaga   240
tataaaaagt actggtcata tcttacaatt ctcatccttc tatattggaa agaattgagt   300

<210> SEQ ID NO 119
<211> LENGTH: 300
<212> TYPE: DNA
<213> ORGANISM: Dirofilaria immitis

<400> SEQUENCE: 119
gtattgggac cgcgtatcgg gaaatctgaa agaagtcttt aacagtattt taaatgaata    60
attcaaatcg ttacttctta atatattaat ttatgcgtat atatgcagta catagcattg   120
cttaaattct tattttttccg cggttaaaac cctatgtaag ataagggagg tgattgtatc   180

```
tgcgccgtac tccttgtttt aatctacctg cttgttgtat atcctccaca tattgtaact    240
gcagcttcac atttgcatat atagtaaggg catcgttgtc tccagaagag atatattatc    300
```

<210> SEQ ID NO 120
<211> LENGTH: 300
<212> TYPE: DNA
<213> ORGANISM: Dirofilaria immitis

<400> SEQUENCE: 120

```
gctgcccgaa tgttacaatt aggacgaaag taaaagtagt tgactgtagg tatgacgata     60
aaggaaaaat ttgtatctta agactttaca atttctaaat attacgtgtt ttatcgtgct    120
aacatcacga attccatatt cacaaaaaaa attttgtaga actccatctg gtttggatga    180
atttgctaca gttgaactgg atgatggaac gaaattgcaa acatctctta ttgttagtat    240
tttctaaatt ctgtgaaatt ttgcaacggc attcatgttt aattattaat ttggagaaag    300
```

<210> SEQ ID NO 121
<211> LENGTH: 300
<212> TYPE: DNA
<213> ORGANISM: Dirofilaria immitis

<400> SEQUENCE: 121

```
aaataagcaa atccgaaagt attacatata cggactaaat attgccattc attcgggagt     60
ataccattgc aaccattggt atttcatttg atcgagaaaa ctagtttttg tagtttggga    120
taaagagaaa tggagagagg aactttcatg atcaatttct ttacgtactg aaattcattt    180
ctatggatgt tctttttcta tttcattctc ctcagcaaat acagtccgaa cagtcatcaa    240
ataagtctaa aaggcatgaa taatataaac atcagcaact ttttaaatga atgcttatta    300
```

<210> SEQ ID NO 122
<211> LENGTH: 300
<212> TYPE: DNA
<213> ORGANISM: Dirofilaria immitis

<400> SEQUENCE: 122

```
atttctataa acatctcttg cattgattaa tttaacatgt tgcaataaat atttcttact     60
tttgaatgta tcatttacta gaaaaaactt caatcgagga ataagtttt aaaataaatt    120 catatttgaa ttcatgtcag ttcaaaaatt ctattactat aatacatgtc tcttggttgt    180
atcttttttt cttttgaaat aatacaatca aacggtttcc taaattttca tagacatcat    240
attttaaaaa aaaatgcatt tgaaaatttt cgaaatcaa tgaacttaat tgatgaaaaa    300
```

<210> SEQ ID NO 123
<211> LENGTH: 300
<212> TYPE: DNA
<213> ORGANISM: Dirofilaria immitis

<400> SEQUENCE: 123

```
gcatgtgtat gtagtatttc tttgtaaaca acatatctaa tctgtctgtc cctttaacat     60
tatagaatag tcagttagtc cgctatttat tttaataaca aaatatctca cttaacttcc    120
atttctttcc taaataattt tgtttcgcta gatctttcct ataattttca aattttcaaa    180
aatgaattaa tcttttattt atatatgtgt atgtatgtgt atgtatgtat gtgtacgttg    240
catatatgta tatgtatgtg tgtatgtgtg tatatgtata tgtatatgtg tgtatgtgtg    300
```

<210> SEQ ID NO 124

```
<211> LENGTH: 300
<212> TYPE: DNA
<213> ORGANISM: Dirofilaria immitis

<400> SEQUENCE: 124
tatgcataat gtgcgaccag ccaataatgt cttcaaacca taattatgca gaaataaatt      60
ttttccagaa ataatttttt tttttttaca tatacttccg atctgtgaga aaatacattt     120
gaagtgaagt gtgaagcaat gctacttttt caaacaacat tgtgaaaatg gattaaaacg     180
caccaatgga gcaagagatc gtaagtttcg ttccgcatgt cctgtggcaa cgtgtaaacc     240
atccgttaac gatatatgat gtaaaagccg acacacccaa attaaaatcc attataaaca     300

<210> SEQ ID NO 125
<211> LENGTH: 300
<212> TYPE: DNA
<213> ORGANISM: Dirofilaria immitis

<400> SEQUENCE: 125
aaatggatcg tattcacttc gtaagaactt agtgaacgaa aaatcaaacc atcacaataa      60
ctttactttt tttctttttt tactaaacac actatcctat gaaaacaaaa tgtccaaata     120
gattcatatg ataatgaact gtgaagttat ccaatctatc agttctcgaa gagggaataa     180
ataaaaacat taagcaaccc accgatcttc gctgaccatc tccttcttca ttagcaagaa     240
gcaaatcttg tggtgatatt tctgcaacca tctgcaaaat aaagcacgaa aaattaagga     300

<210> SEQ ID NO 126
<211> LENGTH: 300
<212> TYPE: DNA
<213> ORGANISM: Dirofilaria immitis

<400> SEQUENCE: 126
tttgatatgc aatcaactaa ccaaatcaga attcaatgca ttctgataaa tttcttcaat      60
atcgtgcatc aattcgacat catattttga cagtgatgct acctttttag ccgtatttcg     120
gaaaaatatg aattcaacca gctgcgtccc aaaatttaag gctgtagcaa gtccagcaac     180
aaccagccct acaactgaaa attctaaaaa ctggttcacg tgcttatcat taataatttc     240
aacactatca ctatctccac atgaacttga tcgattataa tttagtagaa ctgaaaaaaa     300

<210> SEQ ID NO 127
<211> LENGTH: 300
<212> TYPE: DNA
<213> ORGANISM: Dirofilaria immitis

<400> SEQUENCE: 127
acaaattcgt tttaatattg gattacattg aaattgctga ataaagtgg aaatattgaa       60 aagcatttta caatatttgt taacaacatt atatttaaag aatatacacc ttggtttaaa     120
tggtaaaata atctcaagaa ttttcattag gttaattttt ttttatttat ttatattcac     180
aaaaaattgt aaaagaaaac aaaaacaaca ataataacgg tgacaacaac aacaataata     240
ataacaaaac tatttgttgt gattttgcag cattgatgta gtggggatct tttggagcga     300
```

MARKERS TO PREDICT MACROCYCLIC LACTONE DRUG RESISTANCE IN *DIROFILARIA IMMITIS*, THE CAUSATIVE AGENT OF HEARTWORM DISEASE

The present application is a continuation application of U.S. application Ser. No. 14/896,736 filed Dec. 8, 2015 which is a national phase entry under 35 U.S.C. § 371 of International Patent Application PCT/US2014/044000, filed on Jun. 25, 2014 and published in English as International Patent Publication WO2014/210097 A2 on Dec. 31, 2014, which claims benefit of priority to U.S. Pat. App. Ser. No. 61/839,545, filed Jun. 26, 2013 all of which are incorporated by reference in their entirety.

FIELD

Disclosed are genetics related to macrocyclic lactone (ML) endectocide resistance in nematode parasites (e.g., *Dirofilaria immitis*). Single nucleotide polymorphisms within the genome of *D. immitis* are disclosed that, singly or in combination, correlate with reduced responsiveness of the parasites to MLs. Also disclosed are methods for detection of these parasites, methods for treatment of these parasites, and methods and kits for determination of responsiveness of these parasites to MLs.

BACKGROUND

Dirofilariasis is a parasitic disease of animals and occasionally in humans, which may result from infection by a species of *Dirofilaria* such as *D. immitis, D. repens, D. tenuis, D. ursi, D. subdermata, D. lutrae, D. striata* and *D. spectans*.

*Dirofilaria immitis* (heartworm) is a parasitic nematode that commonly infects dogs, foxes, wolves, coyotes, and cats. Heartworms may cause serious vascular damage and may be fatal, especially in highly active animals.

The life cycle of *D. immitis* is well known (reviewed in McCall et al., Adv. Parasitol. 66:193-285, 2008). In brief, a mosquito may become infected when it draws blood from an infected host (e.g. a dog). In the mosquito, microfilariae (mf) develop to the infective larval stage. When the infected mosquito feeds, it may transmit larvae to a new host (e.g. another dog). In the new host, the larvae continue to mature for eight to ten weeks, after which time they move to the right side of the lungs and the pulmonary artery, where they become adult. Adult worms mate and females produce eggs, which develop in utero into the long thin embryos (microfilariae) that are released into the bloodstream. A mosquito that takes in the circulating mf when it draws blood from the infected host starts the cycle again.

*D. immitis* may be found wherever its vector, the mosquito, is found. Generally, *D. immitis* may be found on a world-wide basis, but are very common in areas with mild and warm climates.

Macrocyclic lactones (MLs) are often prescribed as therapeutics or prophylactics in the management of *D. immitis* in veterinary applications. Example MLs include ivermectin (IVM), milbemycin oxime (MO), moxidectin (MOX) and selamectin (SLM). However, resistance to MLs is common in a variety of parasitic nematodes and appears to be developing in *D. immitis*. A number of tests have been described for the detection of anthelmintic resistance in nematodes of livestock and horses, including, faecal egg count reduction test, the egg hatch test, microagar larval development test and molecular tests based on benzimidazole resistance (reviewed in Coles et al., Veterinary Parasitology 136:167-185, 2006). Prichard et al. (European patent EP 0979278) describes a P-glycoprotein sequence in *Haemonchus contortus* which may be useful for the diagnosis of ML resistance in parasitic nematodes. However, there remains a need for methods to detect *D. immitis* (heartworms) that are resistant to a ML.

SUMMARY

Genetic variations (e.g., SNPs) have been discovered in the genomes of *Dirofilaria* spp. nematodes that relate to reduced responsiveness of the nematodes to macrocyclic lactones. In one example, the nematode is *Dirofilaria immitis* (the agent of heartworm in animals). In one example, the macrocyclic lactones are ivermectin, selamectin, milbemycin oxime or moxidectin.

Methods for determining the responsiveness of a *Dirofilaria* spp. nematode to a macrocyclic lactone are disclosed. In one example, the method involves determining the genotype of the nematode at a polymorphic site in a nucleic acid molecule that includes one or more of SEQ ID NOs: 1-127 from the nematode. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

In one embodiment of the method, the presence of an alternative nucleotide at the polymorphic site in the nucleic acid molecules indicates that the nematode is likely to be resistant to the macrocyclic lactone. In one embodiment, the method may include isolating the nucleic acid molecule from the nematode, and optionally purifying the nucleic acids prior to determining the genotype of the nematode. In one embodiment of the method, the genotype of the nematode is determined by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

Isolated nucleic acid molecules comprising one or more of SEQ ID NOs: 1-127 are disclosed. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

Kits for determining the responsiveness of a *Dirofilaria* spp. nematode to a macrocyclic lactone are disclosed. In one example, the kit contains a probe capable of determining the genotype of the nematode at a polymorphic site of one or more of SEQ ID NOs: 1-127. The probe may be an oligonucleotide, a primer or an aptamer. Using the kit, the genotype of the nematode may be determined, for example, by DNA sequencing, hybridization-based methods including using allele specific oligonucleotides, microarray analysis, enzyme-based methods, single strand conformational polymorphism (SSCP), high resolution melt (HRM) or approaches based on PCR, RT-PCR, or qRT-PCR.

Methods for selecting a treatment to treat an animal infected with a *Dirofilaria* spp. nematode are disclosed. In one example, the method involves determining the genotype of the nematode at a polymorphic site in a nucleic acid molecule that includes one or more of SEQ ID NOs: 1-127 and selecting the treatment based on the genotype of the nematode. In one example, the nucleic acid molecule possesses at least 80% sequence identity to one or more of SEQ ID NOs: 1-127. In other examples, the nucleic acid molecule possesses at least 90% or at least 95% sequence identity to one or more of SEQ ID NOs: 1-127. In one example, the nucleic acid molecule includes a fragment having a length of at least 100 nucleotides of one or more of SEQ ID NOs: 1-127 and includes the polymorphic site. In another example, the nucleic acid molecule includes a fragment having a length of at least 50 nucleotides of one or more of SEQ ID NOs: 1-127 and includes the polymorphic site. In one example, the nucleic acid molecule includes a fragment having a length of at least 100 nucleotides and that possesses at least 95% sequence identity to one or more of SEQ ID NOs: 1-127 and includes the polymorphic site.

In one embodiment, the method involves treating the animal with one or more alternative agents when an alternative nucleotide is found at the polymorphic site. Alternative agents may include one or more of an arsenic-based therapy, diethylcarbamazine, and antibiotics. In one embodiment, the method may include isolating the nucleic acid molecule from the nematode, and optionally purifying the nucleic acids prior to determining the genotype of the nematode. In one embodiment of the method, the genotype of the nematode is determined by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

BRIEF DESCRIPTION OF THE DRAWINGS

FIG. 1 illustrates the genotype frequencies for the SNP within Marker 617 (SEQ ID NO: 1), Marker 714 (SEQ ID NO: 2), Marker 814 (SEQ ID NO: 3), and Marker 887 (SEQ ID NO: 4).

FIG. 2 illustrates the genotype frequencies for the SNP within Marker 1514 (SEQ ID NO: 5), Marker 2557 (SEQ ID NO: 6), Marker 3367 (SEQ ID NO: 7), and Marker 3488 (SEQ ID NO: 8).

FIG. 3 illustrates the genotype frequencies for the SNP within Marker 4553 (SEQ ID NO: 9), Marker 5266 (SEQ ID NO: 10), Marker 5365 (SEQ ID NO: 11) and Marker 5667 (SEQ ID NO: 12).

FIG. 4 illustrates the genotype frequencies for the SNP within Marker 6568_A (SEQ ID NO: 13), Marker 6568_B (SEQ ID NO: 14), Marker 7633 (SEQ ID NO: 15), and Marker 9400 (SEQ ID NO: 16).

FIG. 5 illustrates the genotype frequencies for the SNP within Marker 9473 (SEQ ID NO: 17), Marker 9858 (SEQ ID NO: 18), Marker 10349 (SEQ ID NO: 19), and Marker 10520 (SEQ ID NO: 20).

FIG. 6 illustrates the genotype frequencies for the SNP within Marker 10678 (SEQ ID NO: 21), Marker 11676 (SEQ ID NO: 22), Marker 11933_A (SEQ ID NO: 23), and Marker 11933_B (SEQ ID NO: 24).

FIG. 7 illustrates the genotype frequencies for the SNP within Marker 12716 (SEQ ID NO: 25), Marker 12925 (SEQ ID NO: 26), Marker 13063 (SEQ ID NO: 27), and Marker 15000_A (SEQ ID NO: 28).

FIG. 8 illustrates the genotype frequencies for the SNP within Marker 15000_B (SEQ ID NO: 29), Marker 15709_A (SEQ ID NO: 30), Marker 15709_B (SEQ ID NO: 31), Marker 17333 (SEQ ID NO: 32).

FIG. 9 illustrates the genotype frequencies for the SNP within Marker 18110 (SEQ ID NO: 33), Marker 19999 (SEQ ID NO: 34), Marker 20570 (SEQ ID NO: 35), and Marker 20587 (SEQ ID NO: 36).

FIG. 10 illustrates the genotype frequencies for the SNP within Marker 20698 (SEQ ID NO: 37), Marker 21554 (SEQ ID NO: 38), Marker 22174 (SEQ ID NO: 39), and Marker 22254 (SEQ ID NO: 40).

FIG. 11 illustrates the genotype frequencies for the SNP within Marker 22259 (SEQ ID NO: 41), Marker 24708 (SEQ ID NO: 42), Marker 25276_A (SEQ ID NO: 43), and Marker 25443 (SEQ ID NO: 44).

FIG. 12 illustrates the genotype frequencies for the SNP within Marker 26447 (SEQ ID NO: 45), Marker 26730 (SEQ ID NO: 46), Marker 26974 (SEQ ID NO: 47), and Marker 27080_A (SEQ ID NO: 48).

FIG. 13 illustrates the genotype frequencies for the SNP within Marker 27349 (SEQ ID NO: 49), Marker 27461 (SEQ ID NO: 50), Marker 29128 (SEQ ID NO: 51), and Marker 29168 (SEQ ID NO: 52).

FIG. 14 illustrates the genotype frequencies for the SNP within Marker 29455 (SEQ ID NO: 53), Marker 29816 (SEQ ID NO: 54), Marker 30575 (SEQ ID NO: 55), and Marker 30991 (SEQ ID NO: 56).

FIG. 15 illustrates the genotype frequencies for the SNP within Marker 31796 (SEQ ID NO: 57), Marker 32164 (SEQ ID NO: 58), Marker 32223 (SEQ ID NO: 59), and Marker 34439 (SEQ ID NO: 60).

FIG. 16 illustrates the genotype frequencies for the SNP within Marker 34903 (SEQ ID NO: 61), Marker 35336 (SEQ ID NO: 62), Marker 36040 (SEQ ID NO: 63), and Marker 37881 (SEQ ID NO: 64).

FIG. 17 illustrates the genotype frequencies for the SNP within Marker 38662_A (SEQ ID NO: 65), Marker 38662_B (SEQ ID NO: 66), Marker 38622_C (SEQ ID NO: 67), and Marker 38622_D (SEQ ID NO: 68).

FIG. 18 illustrates the genotype frequencies for the SNP within Marker 39492 (SEQ ID NO: 69), Marker 42291 (SEQ ID NO: 70), Marker 42411 (SEQ ID NO: 71), and Marker 45689 (SEQ ID NO: 72).

FIG. 19 illustrates the genotype frequencies for the SNP within Marker 45719 (SEQ ID NO: 73), Marker 46063

(SEQ ID NO: 74), Marker 47481 (SEQ ID NO: 75), and Marker 47722_A (SEQ ID NO: 76).

Figure 1:
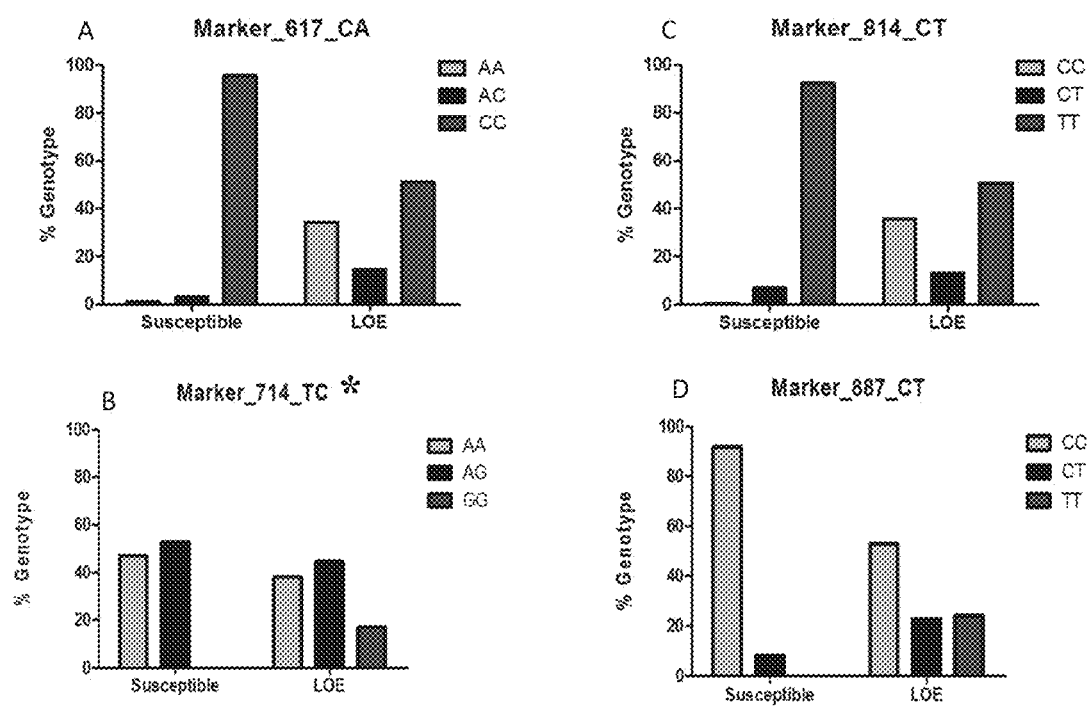
FIGS. 1-28 illustrate the genotype frequencies for the SNP within each of the indicated markers, for susceptible and LOE isolates. The graphs are representative of markers that are also designated as SEQ ID NOs: 1-109 within the application. For markers designated with an asterisk (*), the genotype indicated shows analysis of the reverse complement of the sequences shown as SEQ ID NOs: 1-109 within the application.
Figure 2:
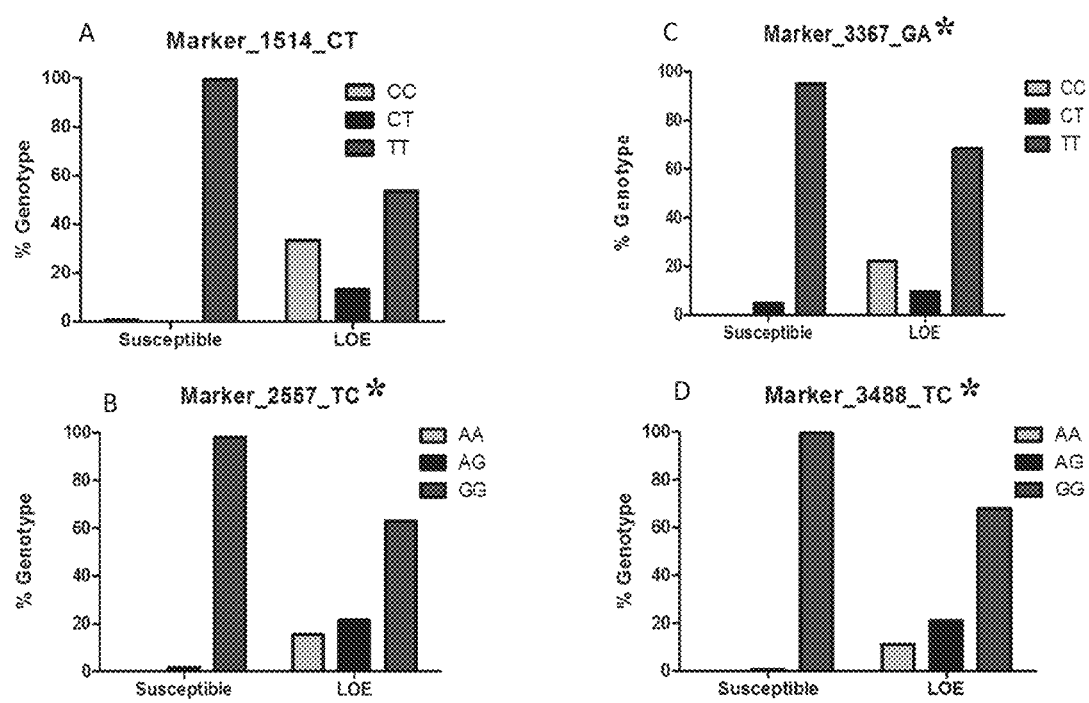
Figure 3:
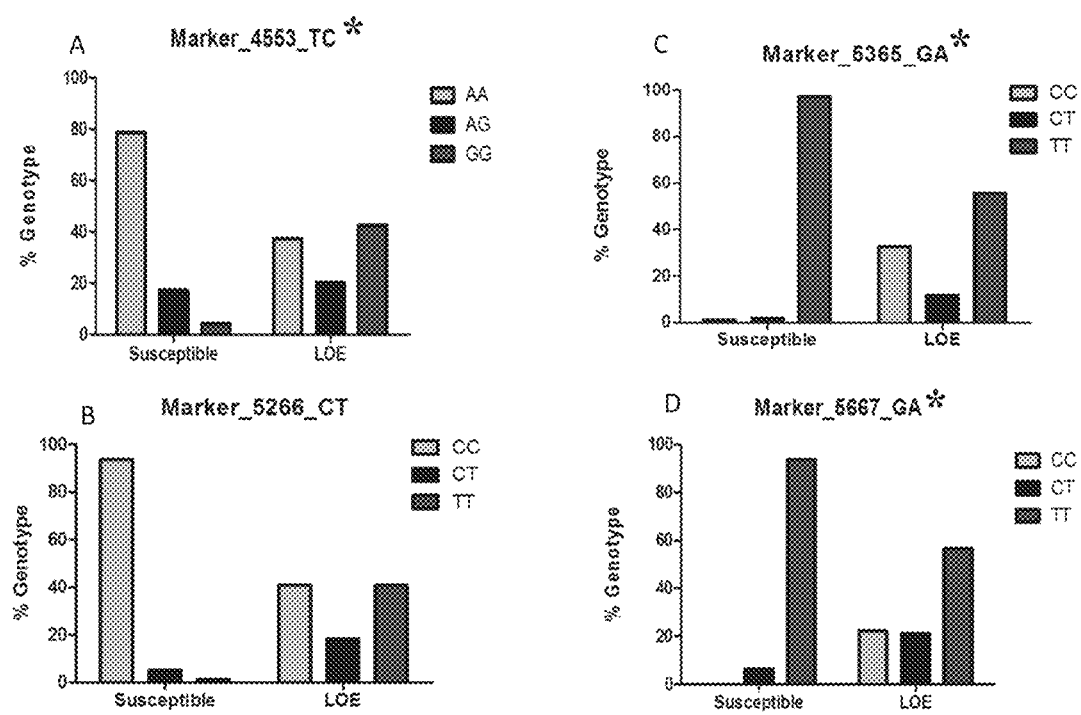
Figure 4:
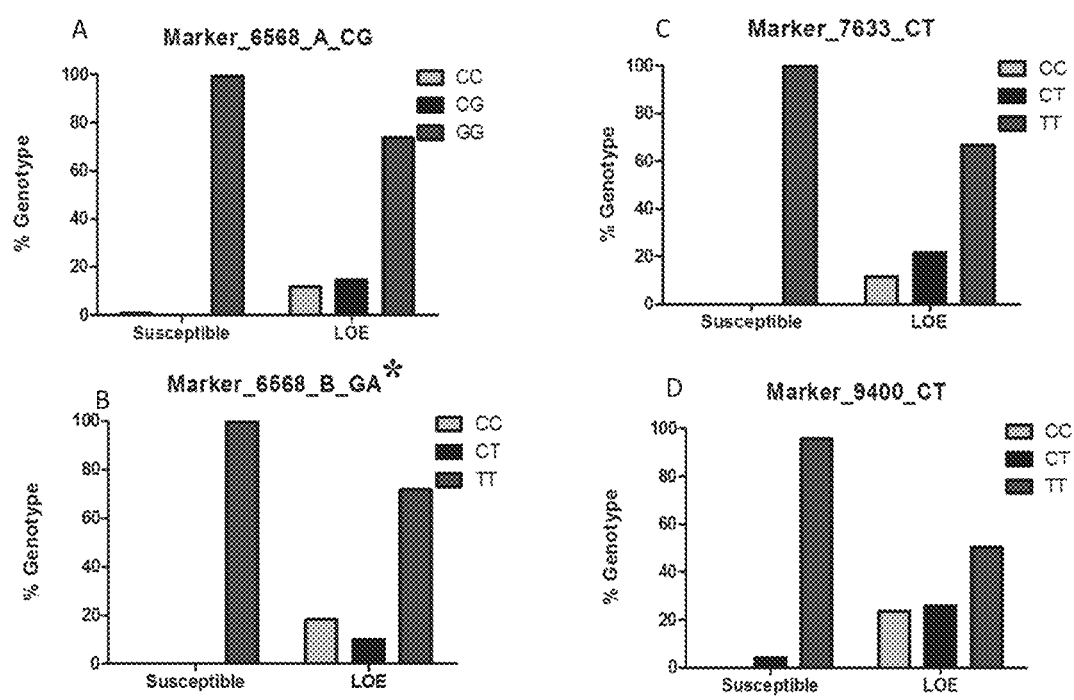
Figure 5:
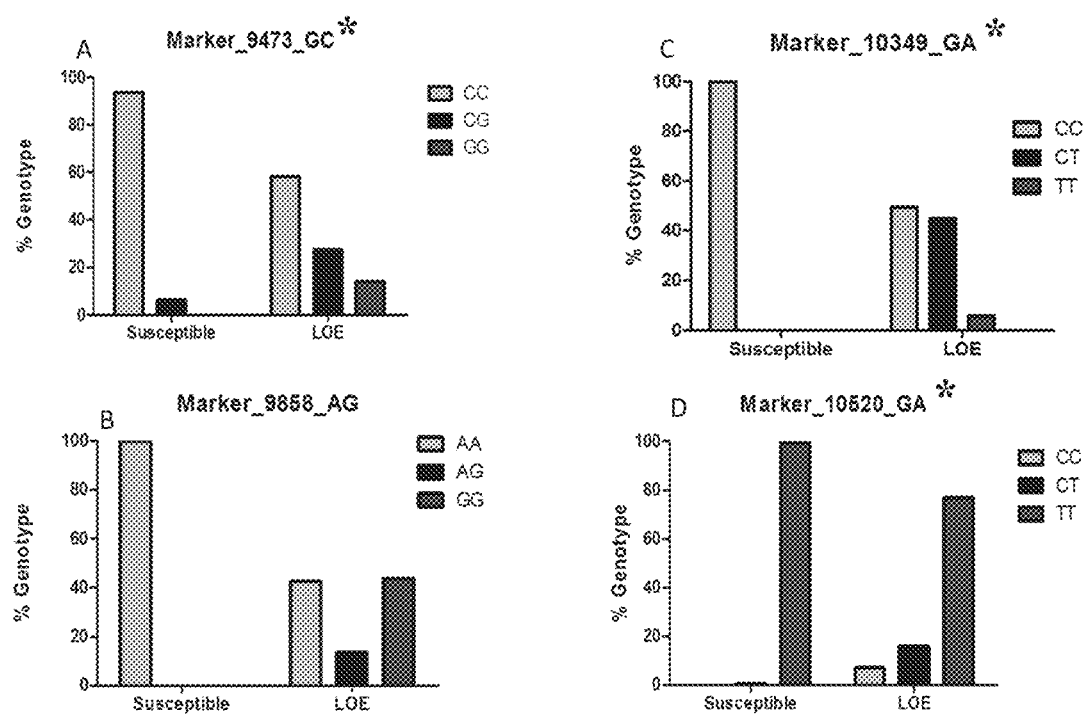
Figure 6:
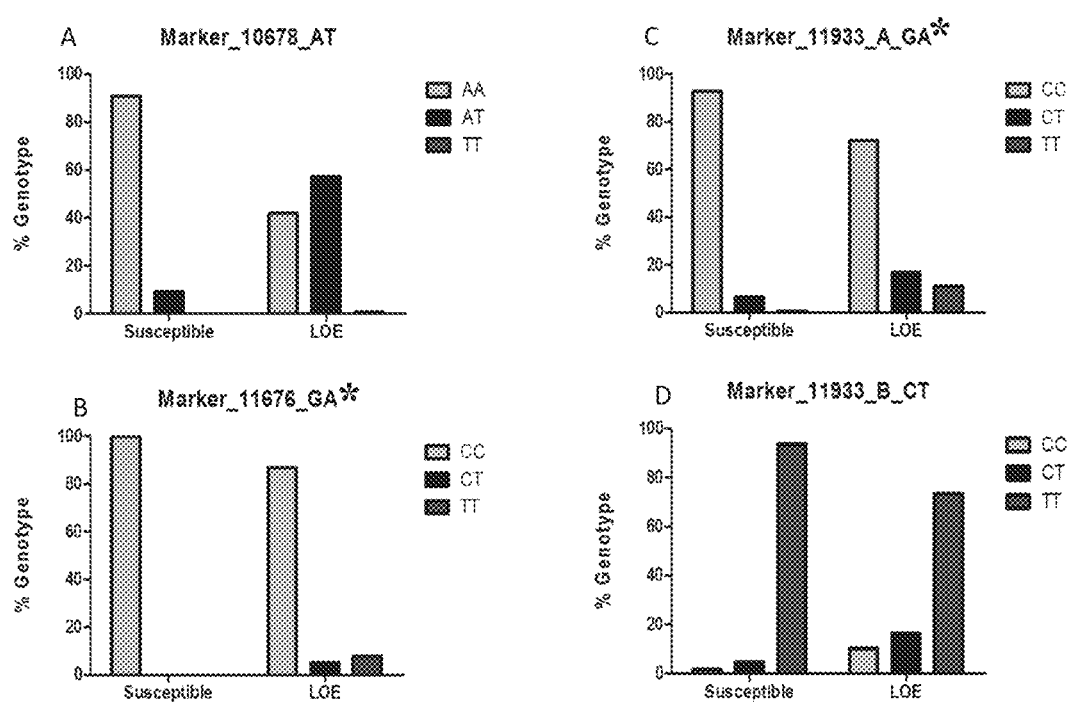
Figure 7:
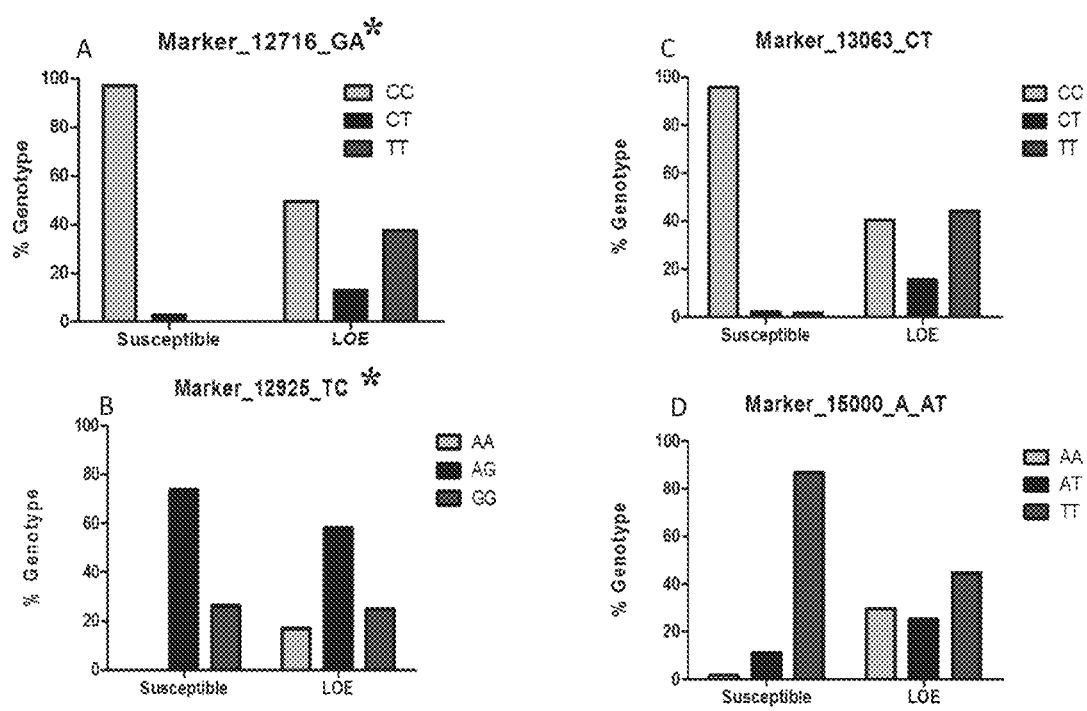
Figure 8:
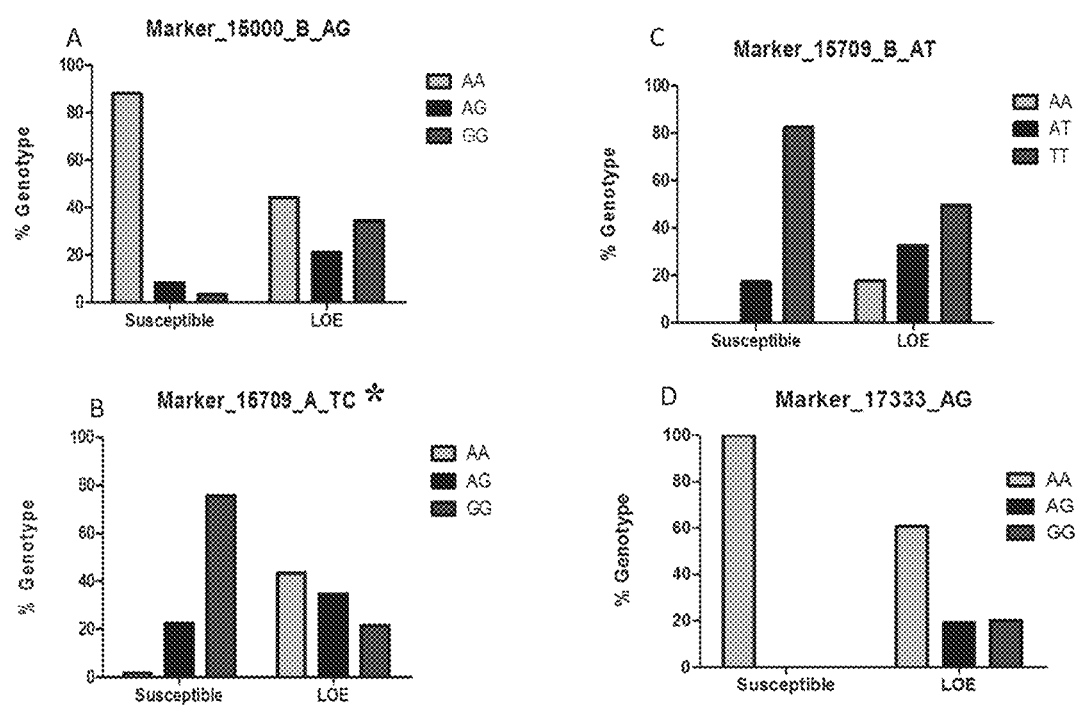
Figure 9:
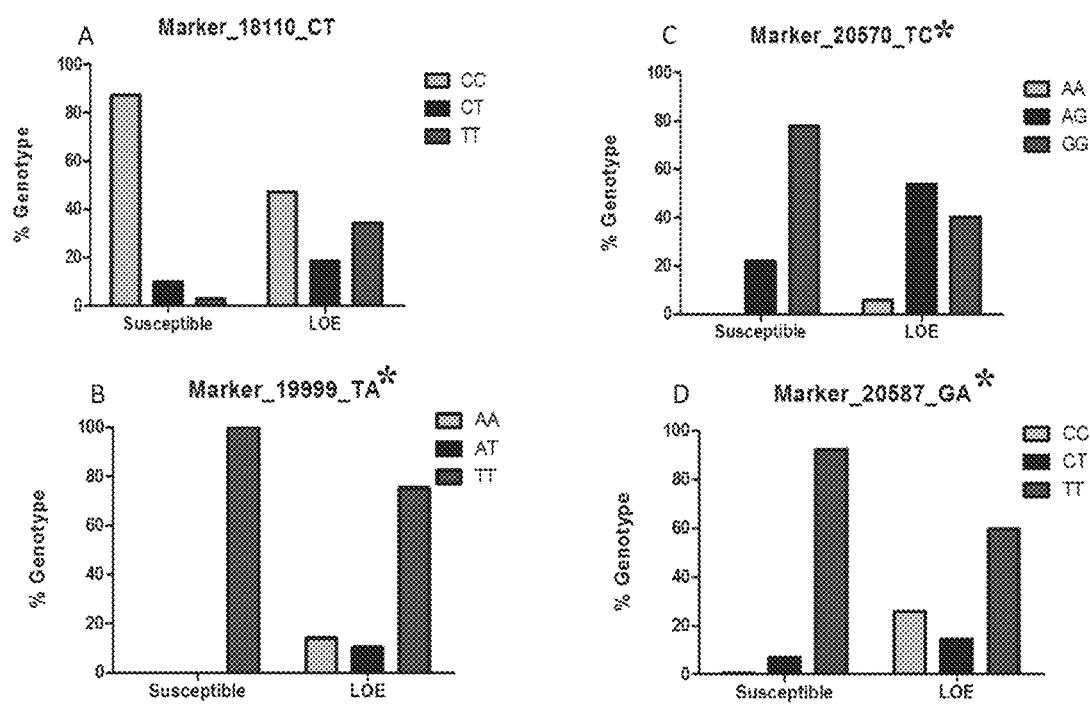
Figure 10:
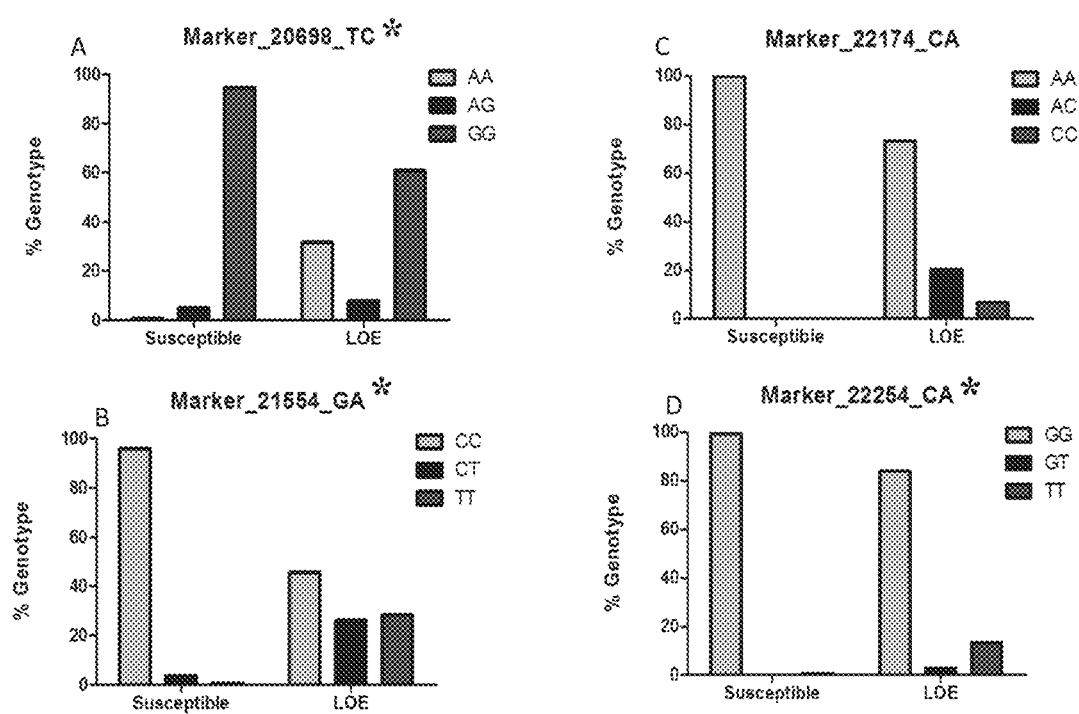
Figure 11:
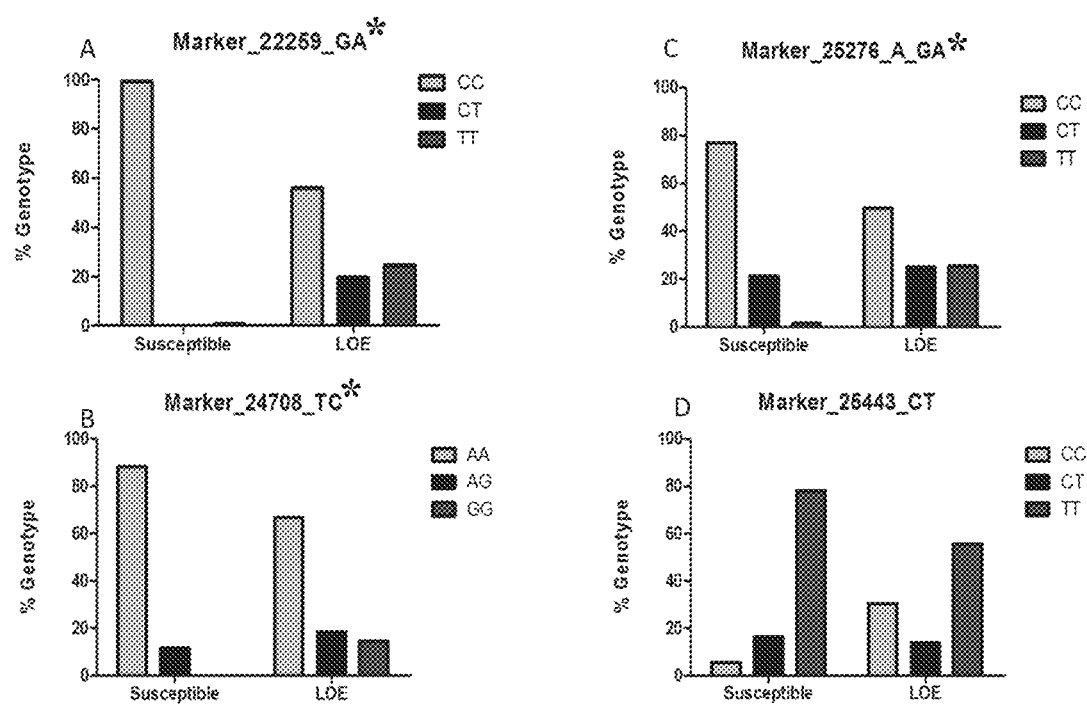
Figure 12:
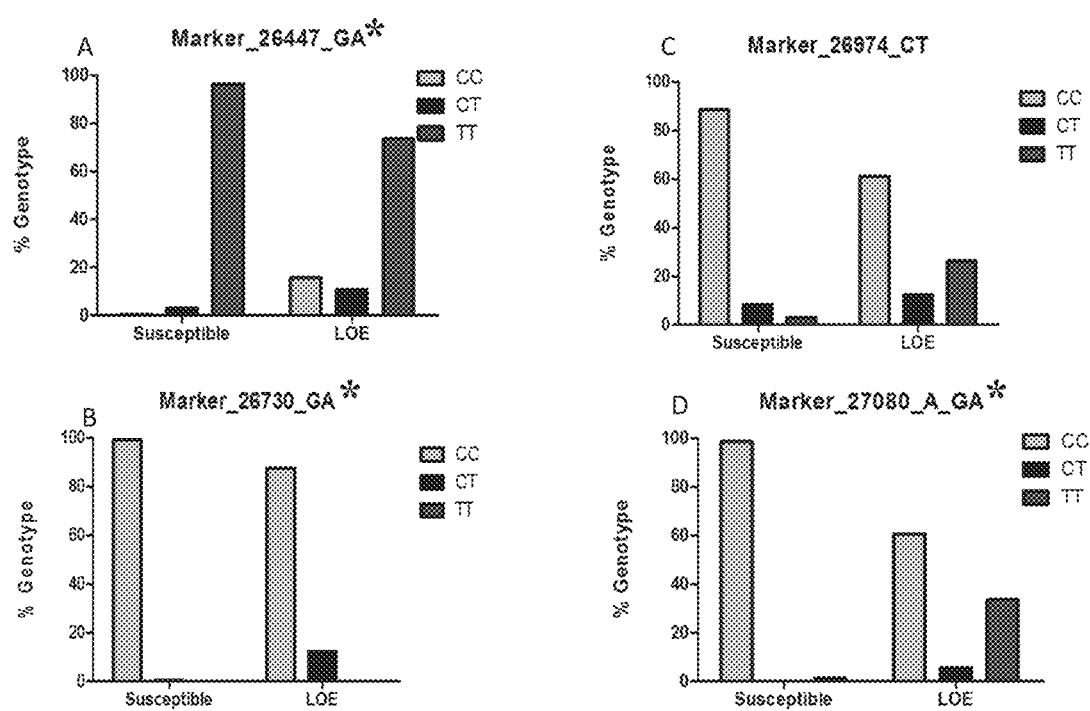
Figure 13:
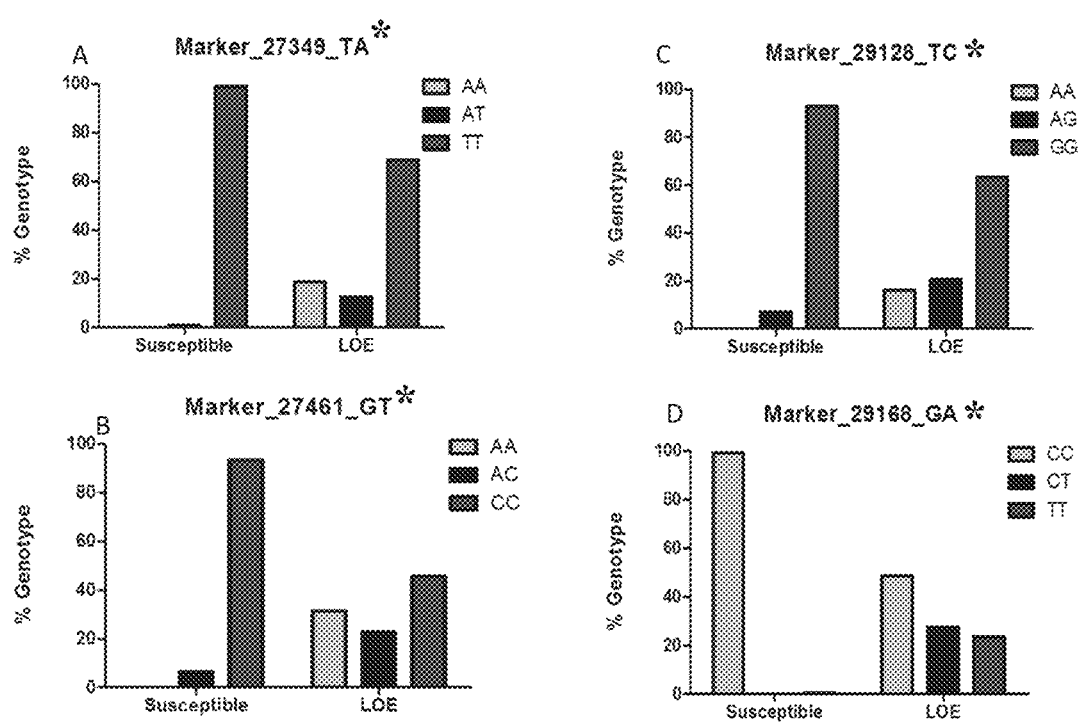
Figure 14:
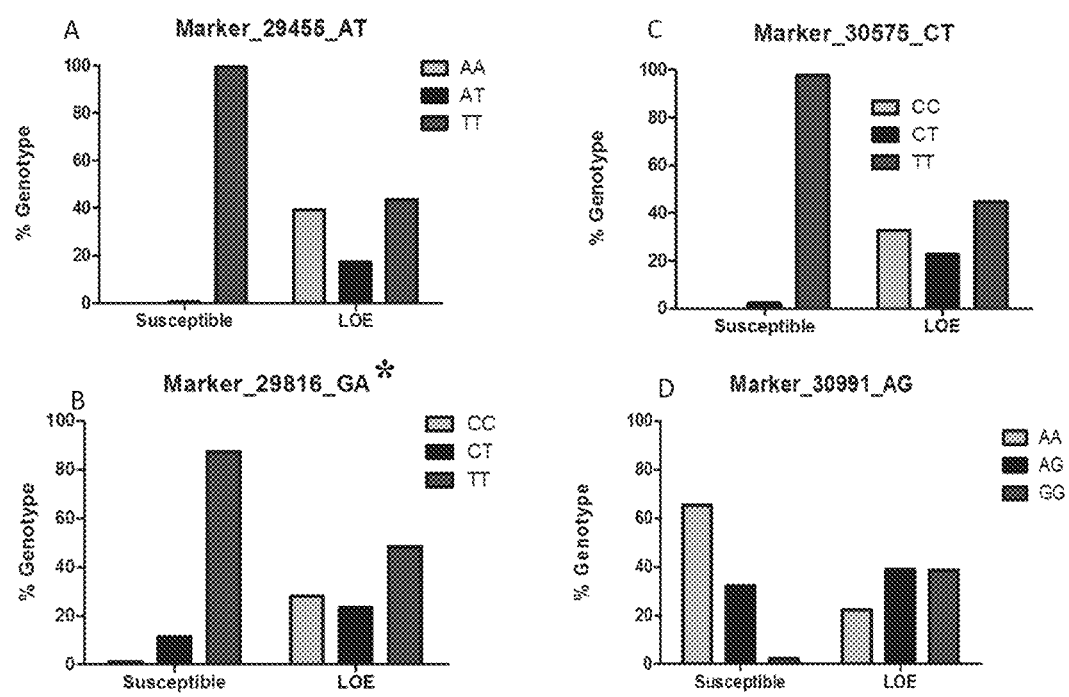
Figure 15:
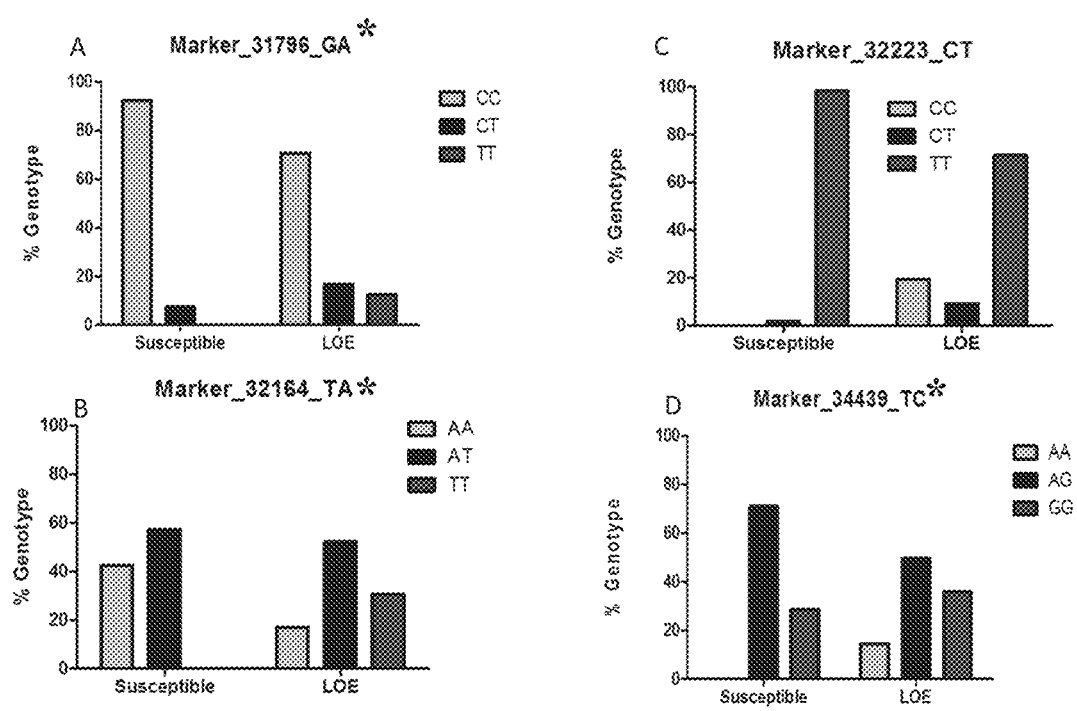
Figure 16:
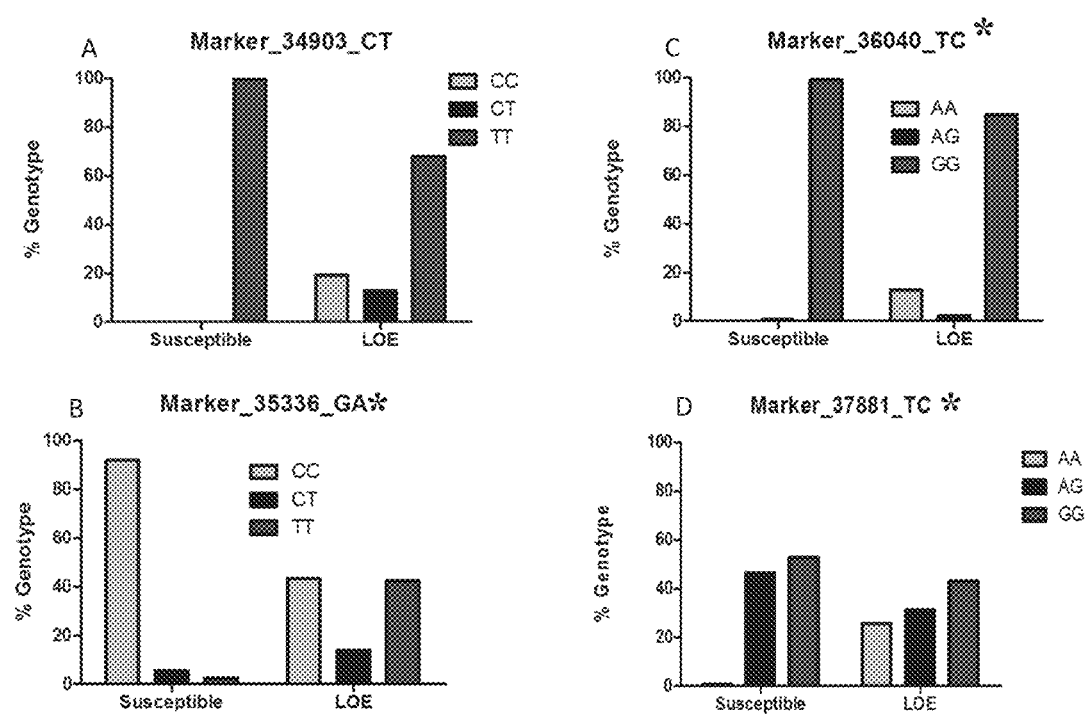
Figure 17:
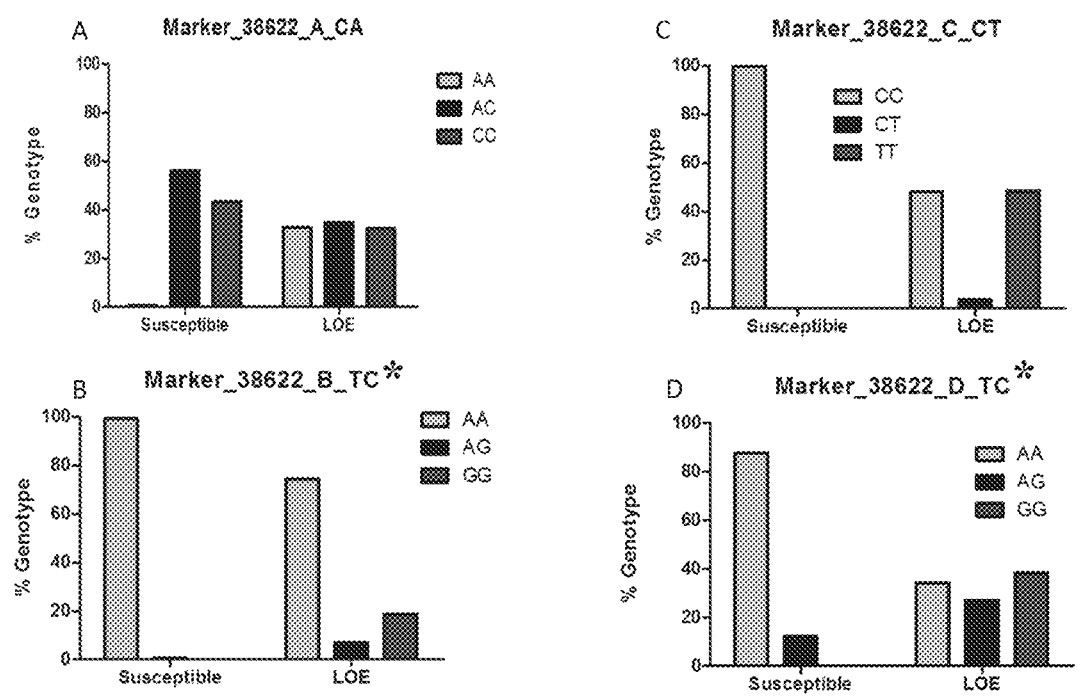
Figure 18:
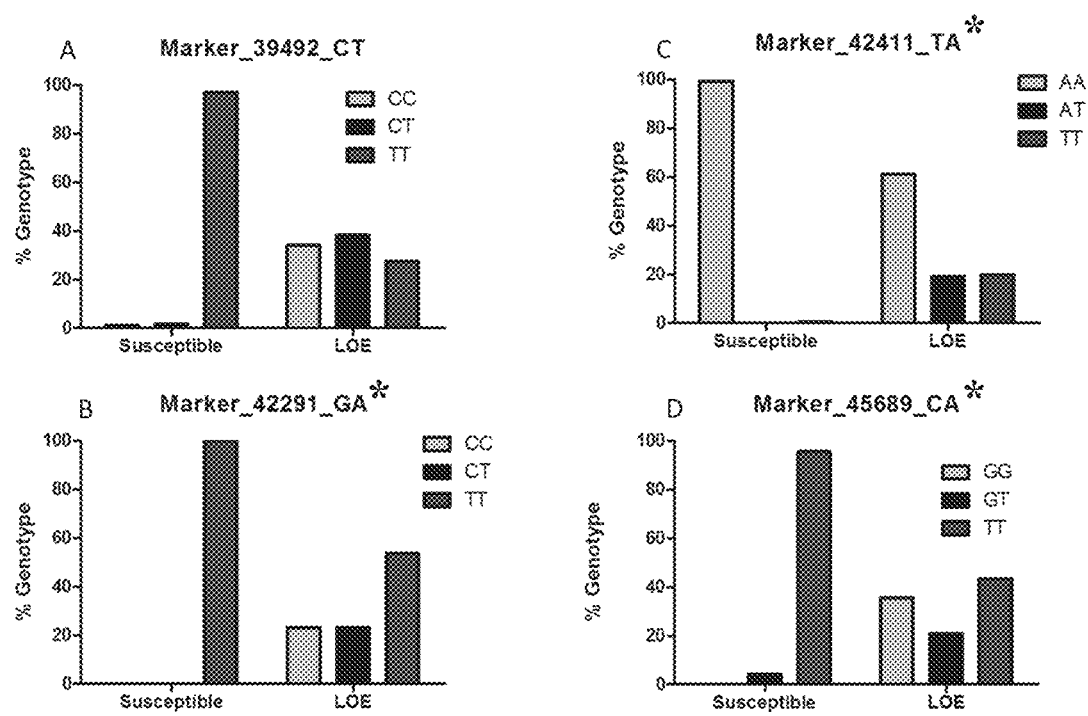
Figure 19:
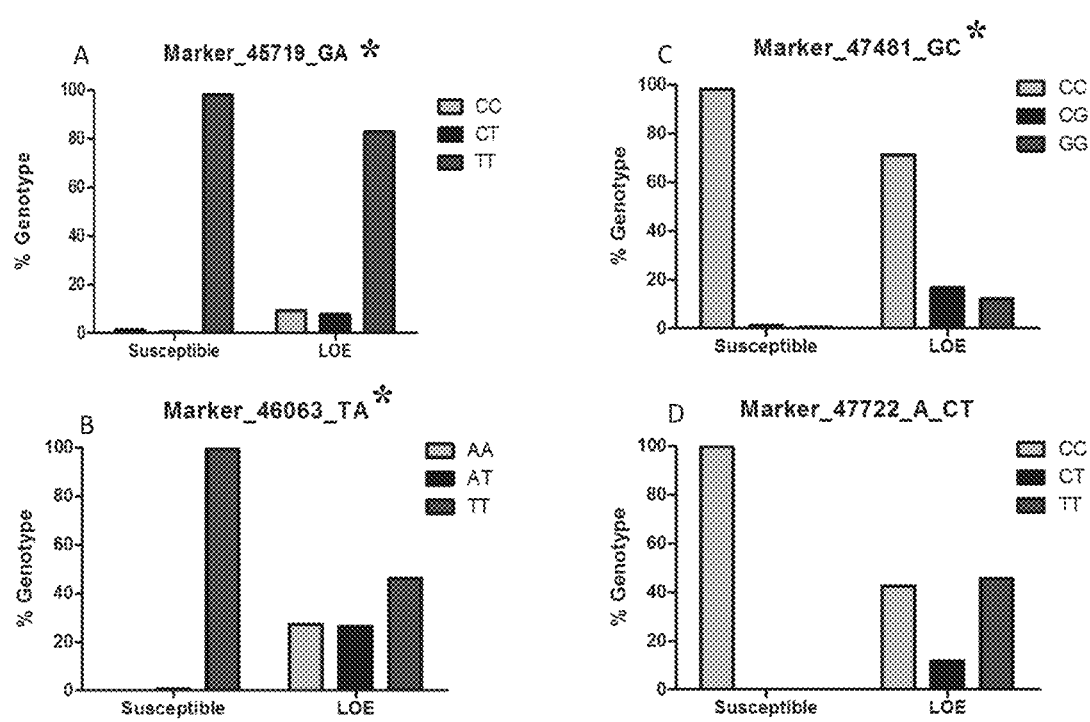
Figure 20:
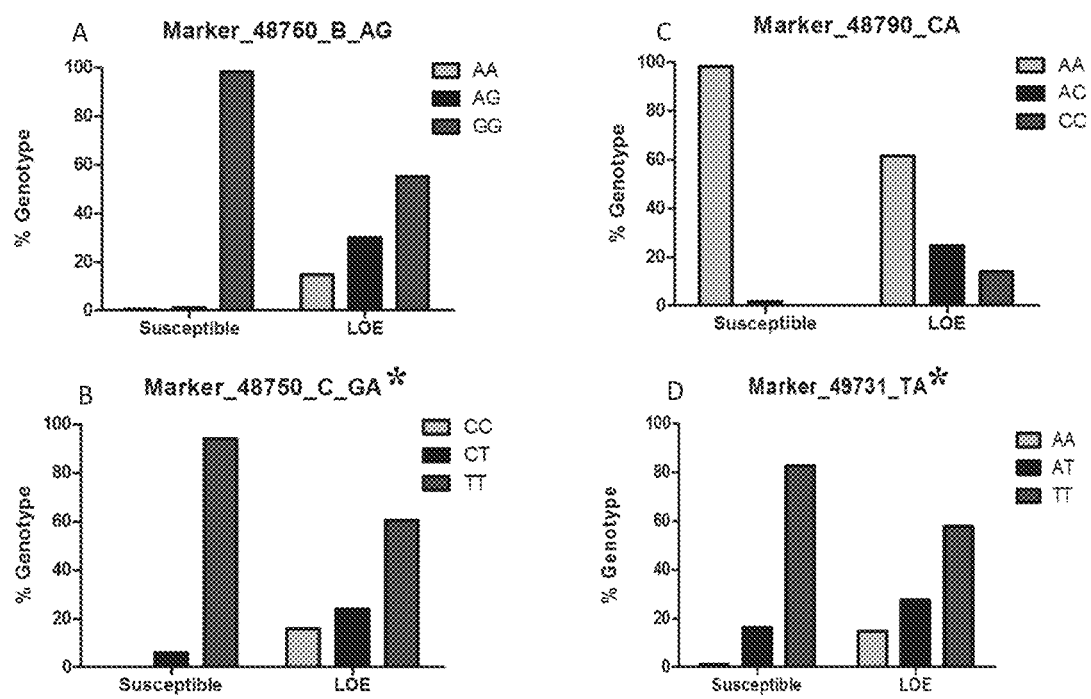

FIG. 20 illustrates the genotype frequencies for the SNP within Marker 48750_B (SEQ ID NO: 77), Marker 48750_C (SEQ ID NO: 78), Marker 48790 (SEQ ID NO: 79), and Marker 49731 (SEQ ID NO: 80).

Figure 21:
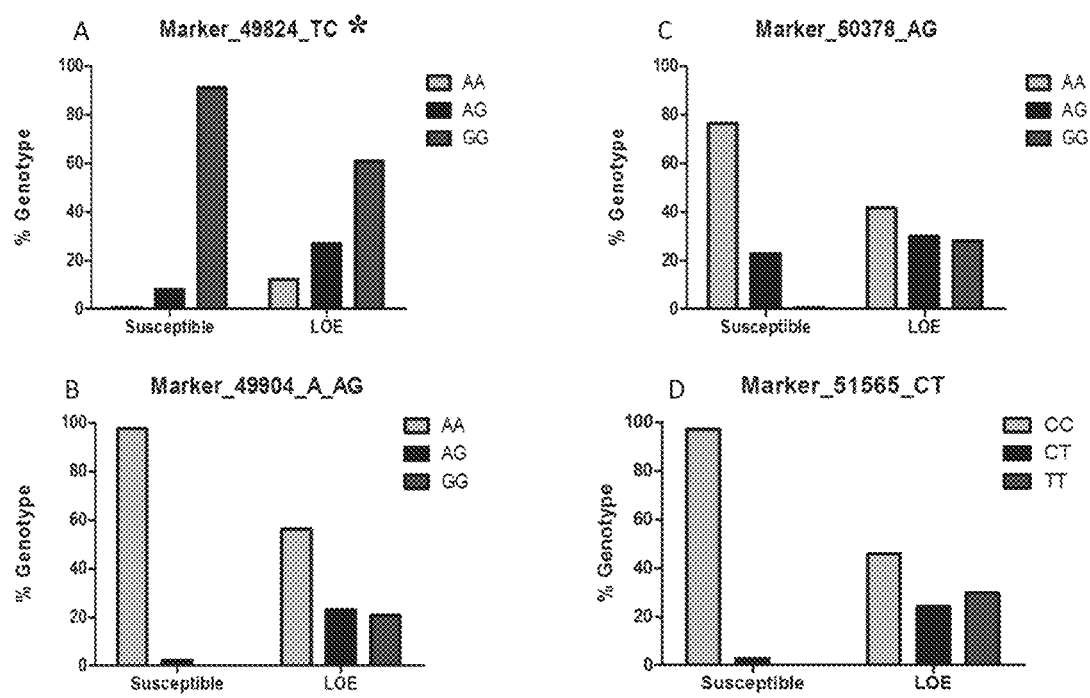

FIG. 21 illustrates the genotype frequencies for the SNP within Marker 49824 (SEQ ID NO: 81), Marker 49904_A (SEQ ID NO: 82), Marker 50378 (SEQ ID NO: 83), and Marker 51565 (SEQ ID NO: 84).

Figure 22:
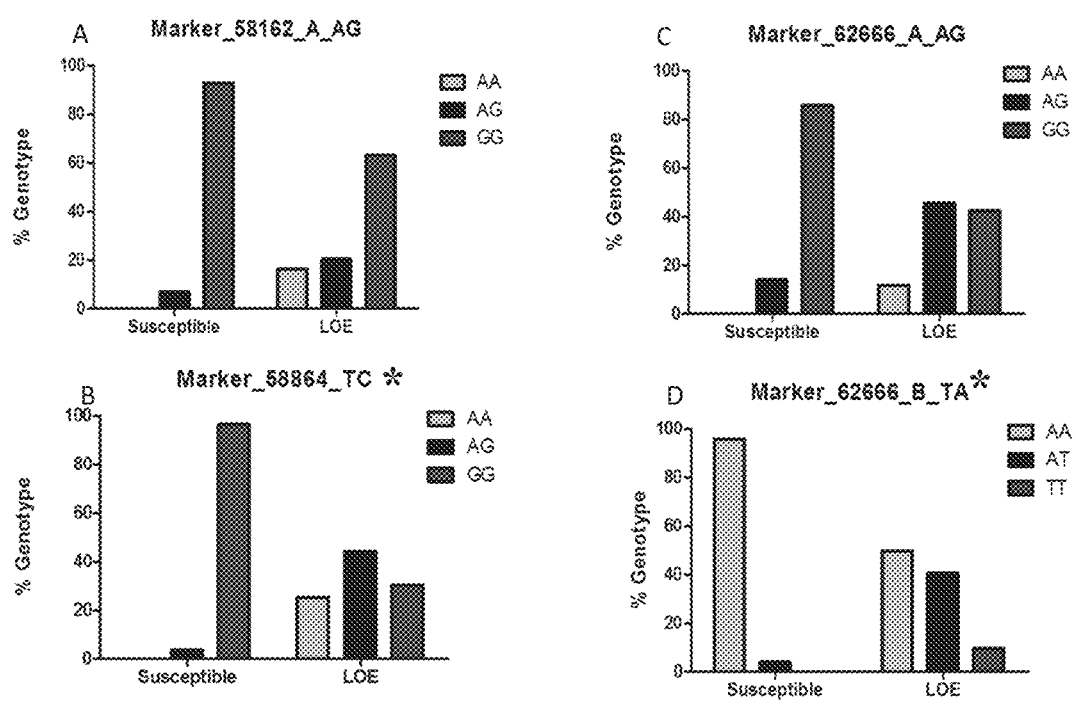

FIG. 22 illustrates the genotype frequencies for the SNP within Marker 58162_A (SEQ ID NO: 85), Marker 58864 (SEQ ID NO: 86), Marker 62666_A (SEQ ID NO: 87), and Marker 62666_B (SEQ ID NO: 88).

Figure 23:
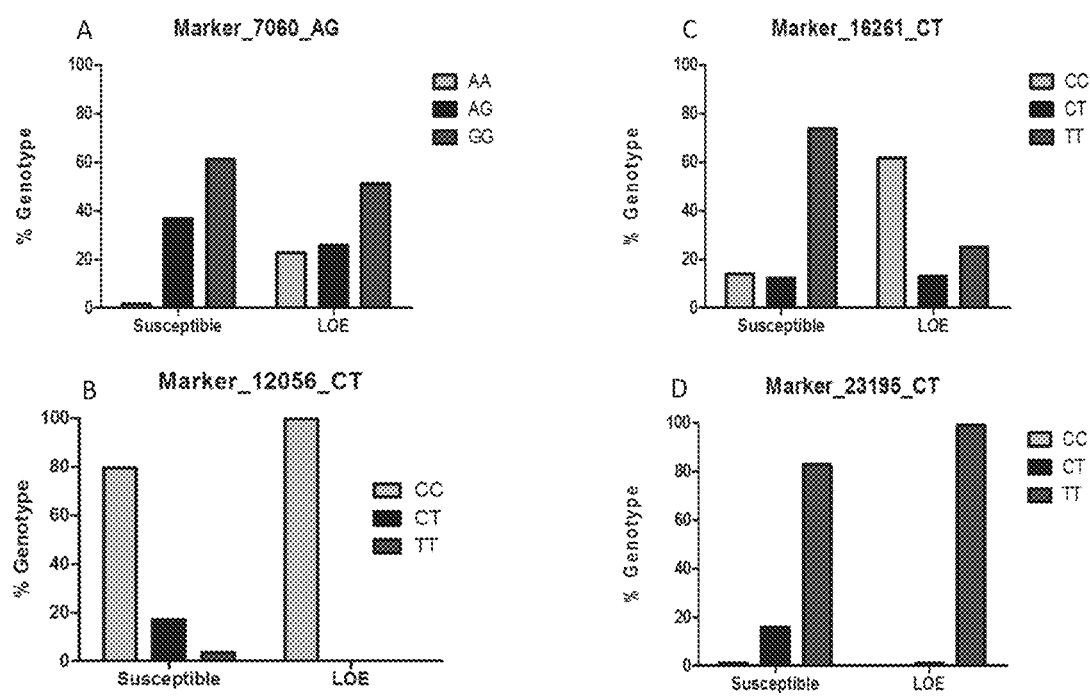

FIG. 23 illustrates the genotype frequencies for the SNP within Marker 7060 (SEQ ID NO: 89), Marker 12056 (SEQ ID NO: 90), Marker 16261 (SEQ ID NO: 91), and Marker 23195 (SEQ ID NO: 92).

Figure 24:
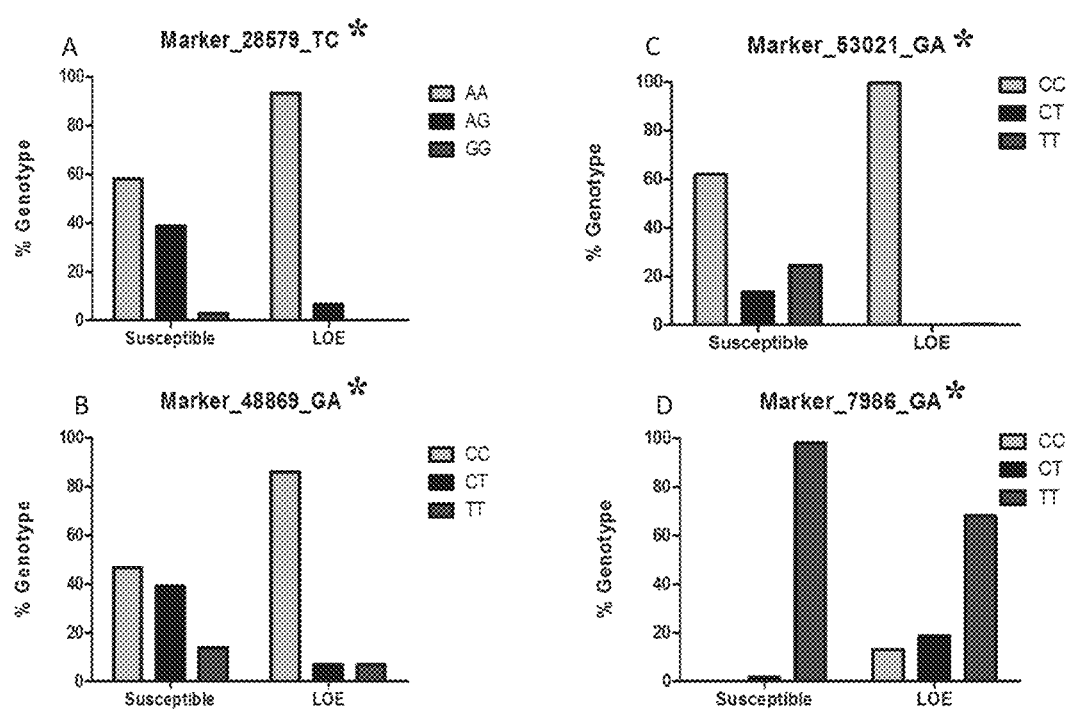

FIG. 24 illustrates the genotype frequencies for the SNP within Marker 28579 (SEQ ID NO: 93), Marker 48869 (SEQ ID NO: 94), Marker 53021 (SEQ ID NO: 95), and Marker 7986 (SEQ ID NO: 96).

Figure 25:
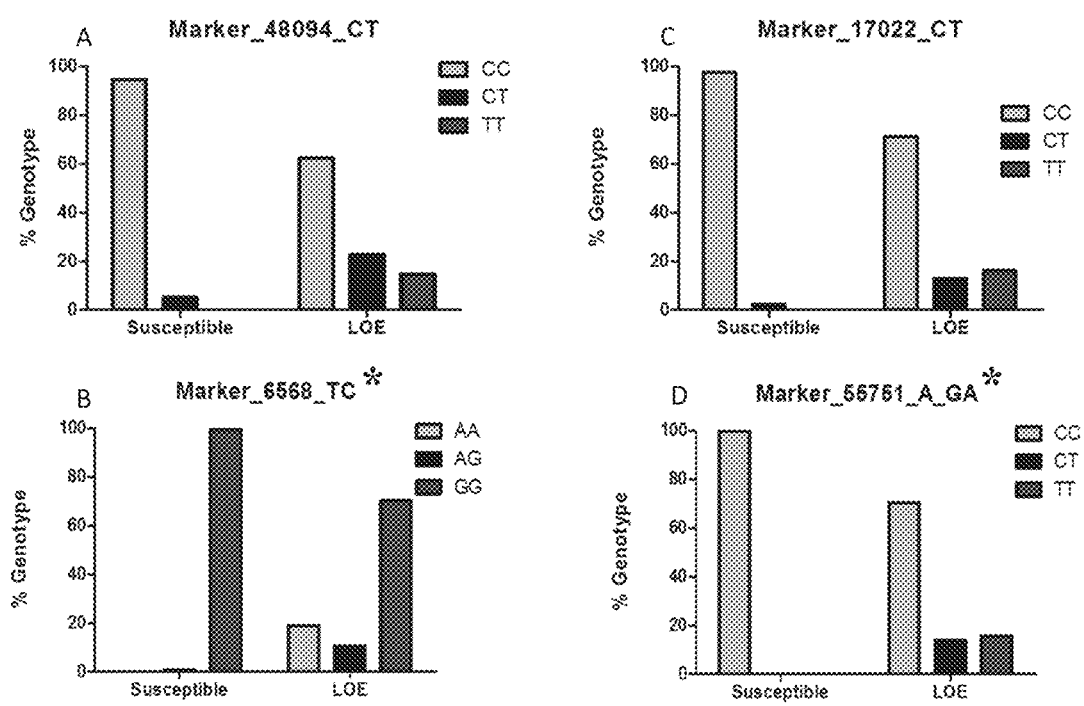

FIG. 25 illustrates the genotype frequencies for the SNP within Marker 48094 (SEQ ID NO: 97), Marker 6568 (SEQ ID NO: 98), Marker 17022 (SEQ ID NO: 99), and Marker 55751_A (SEQ ID NO: 100).

Figure 26:
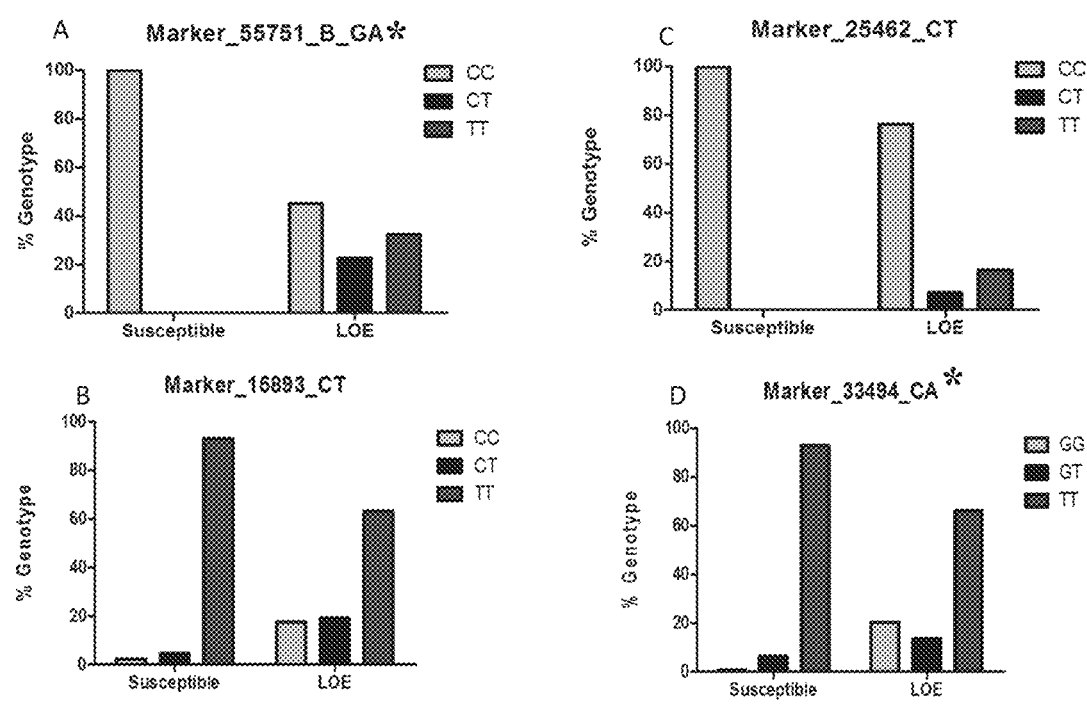

FIG. 26 illustrates the genotype frequencies for the SNP within Marker 55751_B (SEQ ID NO: 101), Marker 15893 (SEQ ID NO: 102), Marker 25462 (SEQ ID NO: 103), and Marker 33494 (SEQ ID NO: 104).

Figure 27:
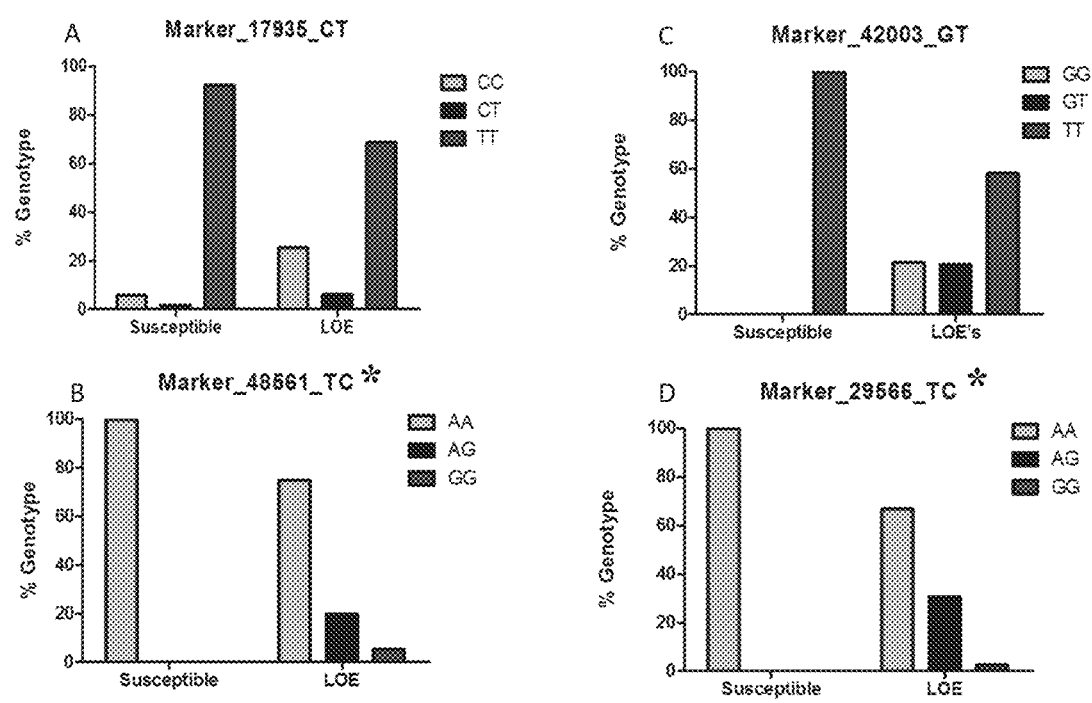

FIG. 27 illustrates the genotype frequencies for the SNP within Marker 17935 (SEQ ID NO: 105), Marker 48561 (SEQ ID NO: 106), Marker 42003 (SEQ ID NO: 107), and Marker 29566 (SEQ ID NO: 108).

Figure 28:
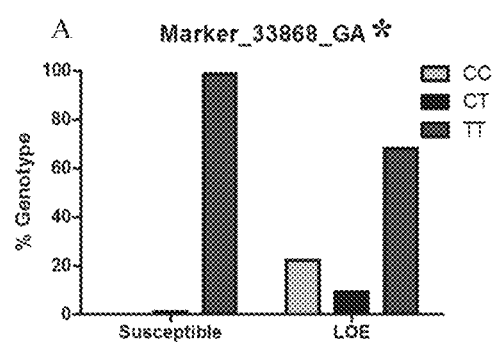

FIG. 28 illustrates the genotype frequencies for the SNP within Marker 33868 (SEQ ID NO: 109).

FIG. 29 presents Table 1 which displays genotype frequencies for markers representing SEQ ID NOs: 110-127.

DETAILED DESCRIPTION

Definitions

Herein, "macrocyclic lactones" or "MLs" means products, or chemical derivatives thereof, of soil microorganisms that belong to the genus *Streptomyces* including, but not necessarily limited to, avermectins and milbemycins. These molecules are used to treat species of endo- and ectoparasites in a wide range of hosts. Avermectins in use include, without limitation, ivermectin, abamectin, doramectin, eprinomectin and selamectin. Available milbemycins include, without limitation, milbemycin oxime and moxidectin. Macrocyclic lactones have a potent, broad antiparasitic spectrum at low dose levels. They are active against many immature nematodes (including hypobiotic larvae) and arthropods. A single therapeutic dose may persist in concentrations sufficient to be effective against incumbent nematode infections for prolonged periods after treatment.

Macrocyclic lactone (ML) heartworm preventatives were developed for the treatment of dogs and cats, which were not already infected, to prevent establishment of adult infections by targeting the developing L3/L4 stages. Macrocyclic lactones also have effects on the microfilarial stage (L1). Macrocyclic lactone endectocides such as ivermectin (IVM), milbemycin oxime (MO), moxidectin (MOX) and selamectin (SLM) are used during the transmission season for chemoprophylaxis for heartworm in dogs and cats.

Herein, "responsiveness" means that a nematode responds following exposure to a macrocyclic lactone (ML). In embodiments of the invention, a nematode may respond by being sensitive or resistant to a ML. Sensitivity or sensitive to a ML means that the macrocyclic lactone adversely affects the exposed *D. immitis* nematode. For example, a ML may be lethal or sub-lethal to the *D. immitis* nematode, shorten its life-span or inhibit its ability to reproduce. Resistance is the reduction in effectiveness of a drug, herein MLs, in curing a disease or improving symptoms (e.g., eradicating heartworm organisms from a dog). A *D. immitis* nematode may be ML resistant if the drug meant to neutralize it is ineffective, less effective or has reduced effectiveness. A *D. immitis* nematode may also be ML resistant if the drug, at a specific dose that is meant to neutralize it, has reduced effect. In embodiments of the invention, responsiveness of a nematode to a macrocyclic lactone may be determined in vivo or in vitro.

Herein, "loss of efficacy" or "LOE" means that there is at least a perceived decrease in responsiveness of nematodes to MLs. The perceived decrease in responsiveness may be perceived or may be actual. In one example, the decrease in responsiveness of nematodes to MLs may be real, in which case the nematodes may be said to be resistant to MLs. In another example, the decrease in responsiveness of nematodes to MLs may be perceived and not real. For example, in the case where a dog infected with heartworm is treated with MLs, for the purpose of eliminating heartworm from the dog, the dog owner may not be compliant in properly administering the MLs to the dog. In such a case, the heartworm infection may not be eliminated from the dog because sufficient doses of MLs were not administered, for example. The dog owner, or other observer, may mistakenly believe that MLs were compliantly administered to the dog (e.g., the owner believes s/he administered MLs as directed but, in reality, missed administrations, administered inadequate dosages, etc.) and, because the heartworms were not eliminated from the dog, the heartworm parasites are resistant to MLs. In at least some of these cases, heartworms are not eliminated from the dog because of the lack of compliance. In these cases, continued presence of heartworm may not be due to ML resistance of the heartworm organisms (i.e., the decrease in responsiveness of the heartworm parasites is perceived and not real). In cases of LOE, generally there is no confirmation that the heartworm infection is actually resistant to MLs.

Herein, "resistant" or "confirmed resistant" generally means that the heartworm organisms were shown to have at least reduced responsiveness to MLs. In one example, dogs infected with heartworm are treated with MLs, using a regime known to normally rid dogs of heartworm infection (i.e., compliance of the ML treatment is not in question), but the treatment does not rid the dog of heartworm organisms. Such heartworm organisms, which would normally be eliminated from the dogs by the compliant treatment, are not eliminated because of their reduced responsiveness to ML. Such heartworm organisms are said to be resistant to the MLs.

In one example, a *D. immitis* nematode may be said to be resistant to a ML if less than about 93%, less than about 91%, less than about 89%, less than about 87%, less than about 85%, less than about 83%, less than about 81%, less than about 79%, less than about 77%, less than about 75%, less than about 73%, less than about 71%, less than about 69%, less than about 67%, less than about 65%, less than about, 63%, less than about 61%, less than about 59%, less than about 57%, less than about 55%, less than about 53%, less than about 51%, less than about 49%, less than about 47%, less than about 45%, less than about 43%, less than about 41%, less than about 39%, less than about 37%, less than about 35%, less than about 33%, less than about 31%, less than about 29%, less than about 27%, less than about 25%, less than about 23%, less than about 21%, less than about 19%, less than about 17%, less than about 15%, less than about 13%, less than about 11%, less than about 9%, less than about 7%, less than about 5%, less than about 3%, less than about 1% or if 0% of nematodes died following exposure to a $LD_{95}$ (a lethal dose or concentration of a drug that should have killed 95% of D. immitis nematodes) dose or concentration of a macrocyclic lactone.

In another embodiment, a D. immitis nematode may be said to be sensitive to a macrocyclic lactone if at most about 5%, at most about 4%, at most about 3%, at most about 2%, at most about 1% or if 0% of nematodes survived following exposure to a $LD_{95}$ (a lethal dose or concentration of a drug that should have killed 95% of D. immitis nematodes) dose or concentration of a macrocyclic lactone.

Herein, "nucleic acid", "nucleotide sequence" or "nucleic acid molecule" may refer to a polymer of DNA and/or RNA which may be single or double stranded and optionally containing synthetic, non-natural or altered nucleotide bases capable of incorporation into DNA or RNA polymers. "Nucleic acids", "nucleic acid sequences" or "nucleic acid molecules" may encompass genes, cDNA, DNA (e.g. genomic DNA) and RNA encoded by a gene. Nucleic acids or nucleic acid sequences may comprise at least 3, at least 10, at least 100, at least 1000, at least 5000, or at least 10000 nucleotides or base pairs.

"Nucleic acids", "nucleic acid sequences" or "nucleic acid molecules" may be modified by any chemical and/or biological means known in the art including, but not limited to, reaction with any known chemicals such as alkylating agents, browning sugars, etc.; conjugation to a linking group (e.g. PEG); methylation; oxidation; ionizing radiation; or the action of chemical carcinogens. Such nucleic acid modifications may occur during synthesis or processing or following treatment with chemical reagents known in the art.

Herein, an "isolated nucleic acid molecule" may refer to a nucleic acid molecule that does not occur in nature as part of a larger polynucleotide sequence; and/or may be substantially free from any other nucleic acid molecules or other contaminants that are found in its natural environment. As used herein, an "isolated nucleic acid molecule" may also encompass recombinantly or synthetically produced nucleic acid molecules.

Herein, the term "identity" or "identical" refers to sequence similarity between two or more polynucleotide molecules, at one position in within molecules, or at more than one position within the molecules. Identity can be determined by comparing each position in the aligned sequences. A degree of identity between nucleic acid sequences is a function of the number of identical or matching nucleic acids at positions shared by the sequences, for example, over a specified region. Optimal alignment of sequences for comparisons of identity may be conducted using a variety of algorithms, as are known in the art. In one example, sequence identity may be determined using the well-known and publicly available BLAST algorithm (e.g. BLASTn and BLASTp). In another embodiment, the person skilled in the art can readily and properly align any given sequence and deduce sequence identity/homology by mere visual inspection.

Herein, "single nucleotide polymorphisms" or "SNPs" refer to genetic variations (or non-identity) at specific locations in a genome (i.e., polymorphic site). Generally, at a specific position in a genome, the identity of a nucleotide may be invariant or constant. At some positions in a genome, however, the identity of a nucleotide may not be invariant. At such positions, there may be a nucleotide present at the position at a relative higher frequency than other nucleotides, when the genomes of different individuals within a population are analyzed. The nucleotide most commonly found at such a position may be referred to as the wild-type nucleotide at this position. However, there may be one or more other nucleotides found at this position at relatively lower frequencies. These nucleotides may be referred to as alternative nucleotides. The frequencies by which the alternative nucleotides are found may vary. In one example, the SNPs described herein may play a role in responsiveness of nematodes to MLs. In one example, the SNPs may identify or tag a region of a genome that may play a role in responsiveness of nematodes to MLs (i.e., the SNP itself is not directly involved in the altered responsiveness to MLs but may be genetically linked to genetic changes that are involved in altered responsiveness). In one example, presence of one or more of the disclosed SNPs may indicate that the parasite whose genome contains the one or more SNPs is less responsive to MLs compared to parasites that do not have the SNPs.

As used herein, the term "polymorphic site" may refer to a region/specific location in a nucleic acid at which two or more alternative nucleotide sequences are observed in a significant number of nucleic acid samples from a population of individuals. A polymorphic site that is one nucleotide in length may be referred to herein as a "single nucleotide polymorphism" or a "SNP."

Herein, "marker" or "markers" generally refer to nucleic acid sequences that can contain one or more SNPs. These nucleic acid sequences can be of different lengths.

Herein, "genotype" refers to the genetic constitution of a cell, an organism, or an individual (i.e. the specific allele makeup of the individual) usually with reference to a specific character under consideration. In the context of this application, genotype generally refers to identity of nucleotides at positions of SNPs. In one example, a GG genotype may mean that at a specific position of a gene (e.g., a polymorphic site) which has two alleles, the nucleotide at the same location in each allele is G (guanine). Alleles are alternative DNA sequences at the same physical locus, which may or may not directly result in different phenotypic traits, but generally within the context of this application, correlate with decreased responsiveness of parasites to MLs. In any particular diploid organism, with two copies of each chromosome, the genotype for each gene comprises the pair of alleles present at that locus, which are the same in homozygotes and different in heterozygotes.

Suitable approaches for use in determining genotype are known in the art and may include, without limitation, PCR, RT PCR, qRT PCR, SSCP and hybridization with allele specific oligonucleotides. Other approaches may include nucleic acid hybridization to DNA microarrays or beads, restriction fragment length polymorphism (RFLP), terminal restriction fragment length polymorphism (t-RFLP), amplified fragment length polymorphism (AFLP), and multiplex ligation-dependent probe amplification (MLPA).

Herein, "consists essentially of" or "consisting essentially of" means that the nucleic acid sequence may include one or more nucleotide bases, including within the sequence or at one or both ends of the sequence, but that the additional nucleotide bases do not materially affect the function of the nucleic acid sequence.

Genomes and SNPs

In one aspect, the invention relates to isolated nucleic acid molecules possessing at least 80% sequence identity to SEQ ID NOs: 1-127, over their entire length, and comprising the alternative nucleotides at the location of the SNP (i.e., polymorphic site), the alternative nucleotides indicated by the underlined nucleotide in SEQ ID NOs: 1-127, as disclosed in this application. The alternative nucleotides generally have a lower frequency of occurrence at the indicated positions within the sequences, as shown in FIGS. 1-29. In one embodiment of the invention, the genome of a nematode parasite, or a population of parasites, may contain one or more of the alternative nucleotides at the polymorphic sites shown in SEQ ID NOs: 1-127. The presence of these alternative nucleotides generally correlates with reduced sensitivity of the parasites to MLs as compared to parasites that do not contain the alternative nucleotides.

In another aspect, the invention relates to isolated nucleic acid molecules comprising, consisting of, or consisting essentially of the sequence depicted in SEQ ID NOs: 1-127.

A nucleic acid molecule of the invention may comprise a sequence corresponding to that of SEQ ID NOs: 1-127 over their length, and containing the alternative nucleotide at the SNP site (i.e., polymorphic site). In embodiments of the invention, the nucleic acid sequence may be at least about 80%, at least about 81%, at least about 82%, at least about 83%, at least about 84%, at least about 85%, at least about 86%, at least about 87%, at least about 88%, at least about 89%, at least about 90%, at least about 91%, at least about 91%, at least about 92%, at least about 93%, at least about 94%, at least about 95%, at least about 96%, at least about 97%, at least about 98%, at least about 99% or 100% identical to SEQ ID NOs: 1-127, but that was isolated from a nematode having the alternative nucleotide at the position in each sequence shown by the underlined nucleotide as disclosed in this application.

In other embodiments, the nucleic acid molecule of the invention may comprise a part of, or fragment of, SEQ ID NOs: 1-127 that also contains the polymorphic site and the alternative nucleotide at the polymorphic site. In various examples, the fragment of SEQ ID NOs: 1-127 may be 5, 20, 15, 20, 25, 30, 35, 40, 45, 50, 60, 70, 80, 90, 100, 120, 140, 160, 180, 200, 220, 240, 260, 280, 300 or more nucleotides in length.

A nucleic acid molecule of the invention may be derived from a *D. immitis* nematode containing one or more of SEQ ID NOs: 1-127 as disclosed in this application. As used herein, "derived from" may refer to a nucleic acid molecule that was isolated from a natural source, e.g. a *Dirofilaria immitis* nematode. It may also refer to a nucleic acid molecule that is man-made, e.g. recombinantly or synthesized on the basis of a nucleic acid molecule isolated from a *D. immitis* nematode.

Detection of SNPs

SNPs may be detected by any method that can determine the identity of a nucleotide at a specific position in a genome (e.g., polymorphic site) and that allows for comparison of the identities of nucleotides at the specific genome position between individuals or populations of individuals. Differences in the identities of nucleotides at a specific position may be indicative of a SNP.

A variety of methods may be used to detect SNPs. In one example, hybridization-based methods can be used. Hybridization-based methods generally rely on hybridizing complementary DNA probes to the site containing the SNP. In one method, dynamic allele-specific hybridization (DASH) relies on differences in melting temperatures resulting from mismatched base pairing. By designing probes that differentially hybridize based on nucleotide changes in target genomes, SNPs can be detected.

In one example of a hybridization-based method, molecular beacons can be used. Molecular beacons are single-stranded nucleotide probes, with a fluorochrome at one end and a fluorochrome quenching molecule at the other end, that can form a stem-loop structure and place the fluorochrome and quenching molecule in close proximity to one another. In absence of hybridization of a molecular beacon to a genome region, the fluorochrome will be quenched, due to its close proximity to the quenching molecule. When the molecular beacon hybridizes to a genome region, the fluorochrome generally will not form a stem-loop structure. Under these conditions, the fluorochrome will fluoresce, due to the increased distance to the fluorochrome from the quenching molecule.

In one example of a hybridization-based method, oligonucleotide microarrays, which are high-density arrays containing hundreds of thousands of probes, are used for hybridization to SNPs. By comparing differential hybridization to redundant probes, it is possible to detect SNPs.

In one example of detecting SNPs, enzyme-based methods may be used. In one example of an enzyme-based method for detecting SNPs, restriction endonucleases are used to digest a genomic DNA. By determining the fragment lengths that result from the digest, it can be determined whether certain sites within a genome fail to be cleaved by the endonuclease due to a nucleotide change (e.g., alternative nucleotide) in the sequence recognized by the endonuclease.

In one example of an enzyme-based method for detecting SNPs, PCR (polymerase chain reaction)-based methods are used. In one example of this, two primer pairs are designed such that only one of them will function to amplify a site containing a SNP, depending on whether the SNP is present. The sizes of the amplified products are distinguishable, therefore informing which primer pair functions, and whether the SNP is present.

In one example of an enzyme-based method for detecting SNPs, nucleotide probes are designed to hybridize to a genomic site and produce a mismatch, whether or not a SNP is present at the specific genomic site. An endonuclease (e.g., Flap endonuclease) that cleaves one of the probes, depending on whether a mismatch exists, is used. Using fluorochromes and quenching molecules, attached to one or more of the probes, SNPs can be detected.

In one example of an enzyme-based method for detecting SNPs, primer extension is used. In this method, primers are hybridized to genome DNA immediately upstream of the SNP. DNA polymerase is then used to extend the primer in a mini-sequencing reaction. The sequencing reaction determines the presence of a SNP.

In one example of an enzyme-based method for detecting SNPs, the 5'-nuclease activity of Taq DNA polymerase is used. A TAQMAN™ assay is performed concurrently with a PCR reaction. The method is set up so the PCR reaction will extend through a site containing a SNP, and release a fluorochrome from a probe hybridizing to the SNP region, depending on whether the probe contains a mismatch due to presence of the SNP.

In one example of an enzyme-based method for detecting SNPs, DNA ligase is used to ligate two probes, one hybridizing to a SNP site in a genome, depending on whether the SNP is present, and a second probe hybridizing adjacent to the SNP site. If both probes hybridize to the genome without mismatches, ligase will connect the two probes, which can be measured.

Other methods of detecting SNPs exist, including for example, detection of single-stranded conformation polymorphisms, temperature gradient gel electrophoresis to detect duplex mismatches due to SNPs, denaturing high performance liquid chromatography to detect mismatched duplexes, high resolution melting analysis, use of mismatch-binding proteins, and others.

In one example of detecting SNPs, a biological sample comprising a *D. immitis* nematode may be obtained from a subject. The subject may be, without limitation, a dog, fox, wolf, coyote or cat. In the context of the invention, a biological sample may be any sample (e.g. bodily fluid, excrement, organ, tissue, etc) from a subject. The biological sample may be from a subject that is known to have, or is suspected of having, a *D. immitis* nematode infection. The *D. immitis* nematode may be isolated from the biological sample with standard separation methods and techniques.

A nucleic acid sample may be isolated or obtained from a *D. immitis* nematode prior to use. Methods of isolating nucleic acids from organisms and tissues are known. Such methods may include, but are not limited to, traditional DNA extraction, with proteinase K digestion followed by phenol chloroform extraction, sodium hydroxide extraction, and physical disruption, followed by purification, e.g. by cesium chloride centrifugation or high performance liquid chromatography (HPLC); or the use of commercial kits. A skilled person would appreciate that different approaches may be used to isolate a nucleic acid sample from an adult *D. immitis* nematode in comparison to a microfilaria. In an embodiment of the invention, the nucleic acid sample comprises genomic DNA.

The nucleic acid sequences of the nucleic acids from the parasite may be determined using any one of numerous methods known in the art. In some techniques, sequences of separate pieces of the genome are assembled into linear whole genome representations of the parasite using computer-based methods. In one example, massive parallel sequencing may be used. Massive parallel sequencing (also called "next-generation sequencing") may encompass various high-throughput DNA sequencing methods. One such method is the HiSeq2000 system from ILLUMINA®.

Through comparison of sequences from separate parasites or parasite populations (e.g., comparison of a consensus or reference genome obtained from parasites sensitive to MLs with a consensus or reference genome obtained from parasites resistant to MLs), presumptive SNPs can be identified.

The presumptive SNPs can be analyzed further. In one example, high-throughput SNP analysis using multiplex PCR and MALDI-TOF mass spectrometry (SEQUENOM® analysis) was used. Generally, this system uses extension of an oligonucleotide primer or probe using chain terminating nucleotides to product different sized PCR products for each allele of a SNP. The different sized PCR products are analyzed using MALDI-TOF mass spectrometry.

Disclosed SNPs

In one example, genetic markers from *D. immitis* include the sequences below (SEQ ID NOs: 1-109), where the underlined nucleotides (i.e., the polymorphic sites) indicate the nucleotide position within the fragment that correlates with resistance to MLs (i.e., the alternative nucleotide). In these sequences, the nucleotide at the underlined position is generally different than the nucleotide found at this position in organisms that are not resistant to MLs (wild-type). In the sequences below, the nucleotide underlined in the indicated sequence is the alternative nucleotide which correlates with resistance to MLs. In the heading for each sequence, the nucleotide change from wild-type to the alternative nucleotide (alternative correlates with ML resistance) at the polymorphic site is shown (e.g., C in wild-type and A in the alternative sequence is designated as C→A). The genotype frequencies for each SNP at the polymorphic sites are shown in FIGS. 1-28. In FIGS. 1-28, for markers designated with an asterisk (*), the graph presents the genotypes of the reverse complement sequence, as compared to the nucleotide sequence presented in SEQ ID NOs: 1-109.

```
MARKER 617 (SEQ ID NO: 1): C→A
AACATAAACATATTGAACTGAATCCTGCAAACAGTTCTCTTATAACGTGAACCATAACTAAATTTAGAGAAAATATG

AAAAAGAAAAATAAGTTGCTTTTGCTCGTGCACCAACTCTAATACCCAGGAAATCAAGAAGTGATAATGAGTAATGT

CATCATTAGATTCAGTAATTGGTGACACTATCAATATTATTATTATTATACTTAAAAATACGACGACCACTTATCGT

AACTTAAAGCATGCATAATACGACTGTCATCATATTACATTTCTTCAAGTTCGTATTGGACAAGTGATT

MARKER 714 (SEQ ID NO: 2): C→T
GACAAGCGTTGACGGGAGAGACGATATAATAATAAAGAAGGCATTGGGTATCAGAAGGCACAATCCAATTATAAATG

CCAAGGCAAAATGAATAAAATTTATGCTGACGATTTGATCAATTACGAAGAATTTCCGATCGGCTCGAATCTTTGTT

TGTATGTGCACTACTGTTAACTTAATCTTTGTTTATATACTTTTGCGTGTCATATATAATATATTCATGTCAACTG

ATACGTTATGATGTTTTTTGTAAATTAAGTTGATCGGAAACCTGAAGTCTATTTCAAATTTAAGAAAT

MARKER 814 (SEQ ID NO: 3): T→C
TTTTAGGAAAATGGTGACTGTAGAGAGATATTATCGGAACGACAAGGTCCACTTCGAACGGGTCTTTTATTGTCGAC

GGATTGTGAACCAAGTTTTGGCATTCATAATGACAGGTAGCTATTTTTCCATCATCCCATTTTTGTATTAGTGCAAG

CAAGTCATGAGTCGAAAGAAAATCTCAAAAGAAAAAAATGAAATTTCAGGTTCAAAGGACTGCGTCCATTATTCGCA

CTGGTTGATGAGAACGTACAGATTCCAGAGCGGCAATGCTGCACAGTATCTTTTGTTTCACTTCTGAAT

MARKER 887 (SEQ ID NO: 4): C→T
TCGATTAAAAATTATCATCGATAAAATTCTAAAATTTATTTTAGTAAAATTATTATTATTTTGATGAATAAGTTAAC

AAAAAAATTTTAATAACTTTTTGATTCGCCAAAAATCTAATTCGTTAAAAAGTCGTTCCAAACAGATATCGCTTGTT
```

-continued

CGATGAAAATGTCCGGTTGTTAGAAAATCATAAATTGGTTCAAATAATTTTCCAGAACGTTCGAAAAAATATTCCCT

TGTATCGGATAAATAACCATTACAATTTTCCACTCGTGTTGCATGTGTTTCTCGACAAAAATCAGCTAA

MARKER 1514 (SEQ ID NO: 5): T→C
TCAACAGAAATCGAGATTCCAAAAAGTTTCCTACAAATACTTAATTATCAATGGATATTTAGTTTTGTTATCTGTTA

TCATAAGTTCTGCTTCTTACACGATTAAAAATGTCCAAGAATTTTTTACTATTCAAATGAGGGAAATAAAAAACCAA

TGCCAATAATATCCAGAAACTACATACATCTTTCTTTTTTCGAAGCTCATCTATTCCGGCCGAAAACAATGAAGAAC

ATTAAAATTCTTAAAAGATAGTCTTAGCCTTTTCCTTGACCACTATCTTAACTGTCAGCGCTAAAATGT

MARKER 2557 (SEQ ID NO: 6): T→C
AATAGTCGTCTCATTACTTTTTGACTTTTATAATTCGAGAATCTTATGTAGTCCTTCACTTTACCCTTCTTCTGTCG

AACTAAGAATTACAGCATTATTTTCGAATTTAATGTGTAAAAGACAATAGCAGATTTTGTAATTTTGTGTTAACCTC

ACTTTATATTTCGCTTCATATCGTGACAGAGAATTACTATTTCAGAGAGTATTACTTGTCACCAGAGAATCTCCAGA

AAGATTTTTATTTACGTCGGAAAATGGACAAAAATGGTTTCTTATCATTAGCACTGATAGCTAGTTTCC

MARKER 3367 (SEQ ID NO: 7): G→A
TATCTCTTGTTGTGTGTTCTGCATTGTATCAAAGTGGGTAAATTTTGCTTTAGACGTTGACTTATTGTCTTTTTTAA

GTTATATTCTAGTCCATGTTTTTCTCTTTGCAAATATTTTTTTCCGCCGCCTATGATTCATTGTTTTGTTTGTAACT

CTCTATTAAGTTGCTTTTAGTTTGAATTGTATCAAAATTTCAAACATTTAAAATACGCACTAGCACTATTTTTTCTT

ATCTCAATTAAGCGAATCCCGGAACAAGATTTAATCGATTTCCGAATCACAATTAAATCACTGGAAAAC

MARKER 3488 (SEQ ID NO: 8): T→C
ATTTTCCTTAACAAATCATTTTCAAACGAAAAAACATTAAAAAGTGTTAAAATAAAATGGTGATATTGATAAGAAAT

TAATTCAACCTGCATATCAATTCTTGTAGCGGCCATTTTCTTAGCAAGTTCTATAGCAGCTCGATCCATATCACCTT

CTTGCTCTAATGTCAATTCCGGTTCCGGAATTTTTTTTATTTTGCCATTCTTCATCTTTTTTTTATTTTTTACTGAT

ATAGCTATAGACCCTTTCTCCCGTGCATGCCTGTAGGCCTGTTCTGATATACAGGCTTGTGAACCACTG

MARKER 4553 (SEQ ID NO: 9): C→T
TTCTGGGGTAGTTATACGGAAAATTAGACAATGAAGAGAATCAAAAAACATGCGATTTTCAAACAGAGGAACTTTGG

TACTTTTGCCTCGACTTACTTTATTTTAAAACCCATACAAAATAAATGTTTCATTTGATTGATATTGTCGTACTAAT

AATTAGAGCTTCAACATTAGGATTTTAATAACCTTCAATTTATTTCAGAATTTAAGAAACTTACGTATGGATGGAGA

AAATATAAAGAATGGCGATGACAAATAAGATTTGCTATGAAAAAACTAATGCCACAAGATCCGAATGCA

MARKER 5266 (SEQ ID NO: 10): C→T
TTTATGAACAAAATAATAAAAATTAGGATAACAGATATCAATTTCTTTTAGCTATAAATATACGCTTCGATTGAAA

AAAGCTTTCAAATTATAATTAAGGCATACGTTACGATATAGACAATTAAGTCGACATTAATTATTTGAAATATTTTA

AATTTTTTCTCTTTCTTTTTTTCTATTCTCTTCCAAAGTGTCAAATAGTTATGAAATTGTCAGAAGCTAAAATGAT

AATATTATTCAAGTTTATTACCTAATCTTTTATCACCTCATTTCTTATCATTTATCTGAAAATCTAATC

MARKER 5365 (SEQ ID NO: 11): G→A
ATGTTGAATTTTTAATGAAACTTTTTCGGTGCATAAGCATTACAGATCTGTAAGCTGTGCAAACCCTGTTTCTTTGT

AAATTGAAACAAAGATCATTTATTGTTTCCAGCGTCGATTTGACCTGGATAAATGTGGTACCAAAAGTAGATGACGA

GAGGTAAGTGCAAACAAAATGCACAAAAATGATTTTGATGCACTCAAATCATTTTTAAGTTTTGTGCAATTTTCCAT

TTTATAGTTTCGTGATCGGTTGTTATTCATCAACTTGATTTTGTTTGTTTTTTGTGACTTATATTTCAT

MARKER 5667 (SEQ ID NO: 12): G→A
TTTGACACTTTCAGATACCTTACAAACTCATCTCCAGCACCCAATTTACAATATCGCTGCCTAAATAAAGAATTTAT

TCGGATATGAGACTGTAGTTTTCATTCCGTACCAATCATAGTAGAACAGATCTATAGCATGGTGTCCTACTAAAGTT

GTGACTGGCTATTAAGTATGTGGGTGTTTTTACGTGTGCGTGGGTGTTTGTGCGTGTGTGCGTGTGCGTTTCTGCAC

ATATTTTCGTGCGCGGTGTCTGTGTGTGTCCGTTTGTATATGCCGAGTGTAGCTGTGTATGTTCTTG

MARKER 6568 A (SEQ ID NO: 13): G→C
CACTCATAATATACCTGTCAACAAACTCAGAAATCTGAATAAAATGACGCAAAAATGACAAAAACATTTTATCAACC

TTTTCTTCATCACTCCCCCGCATTTCCAATTTTCTTCCAAACTGTTTTTGTCGTGCTACAAAGTCATCAGCCACTTC

-continued

ATTTTCTTCAAGATGGTTCGAGACGCCATTCTTGGATTCACCCCTTATTTCAACTGTTTCCGAAGTCCCAGCAGTTG

AAGCTGAACCTAGCATTTATATCACCACCCGATGTCAAAAAATGACAGCGGTCAGAGAATACGACTTCC

MARKER 6568 B (SEQ ID NO: 14): G→A
GCTAGGTCAACAGTTGGTTTATTTGGACTTATACGATATTAAACATAATATCGCCTCATATACACAGAAATATCAAA

AAAACGAACACAGCTAAATCGAAGAATACGAACAAATGTTTTAAAAATTATATTAAATCTTTTAATGCTCTCTAC̲AA

TGTCGTATCTTCCCTTTTGTCTGTATTTCTCCTTTCGTTCCACCACTGCTATTTCTCATGCCTTTGAACTATGGTTC

TCGTTGCGTCGAATTGTCCTCGAAACTGTTGTTTCTGTCGAATTACGTCGAACTGCTGGACTTTGTCGG

MARKER 7633 (SEQ ID NO: 15): T→C
ATATCTCACTTCTGACATAAATTGAAGTGGCACTGATTTGAATGAAATGATAAATAAAATAAAGACGACAAGGTAGT

GGAAAAAAAAAGAGGAGAAAACACCGTTTAGTTTTGGATGCAAGCTCGAATCTGAGTTTTCTTGCAAACCGTAC̲ACT

GATCAATTTTCTTACACAAACATAAGAAAAAAAGAAGTGATTTTACTGTAGCTGTATCGTATAATTCAAATCATATA

TATATATGTTTCAATAATCTATACATTTATGTATATTTTTTTTTGAATGGAACAGTGAATGATTTTAAA

MARKER 9400 (SEQ ID NO: 16): T→C
ACAAATGCCATCGGAGAGAAATATCGTTGGCGTACTGATCACATTGGCGGTATCACTTCTTTGAAAACTCCAGCTG

GTATTGTGTATCATTTCATGCAATACGCTATTTTTGATCGAATATGTCGACGGCGTAGTGTTTCATTTTCCAAC̲GCA

TCTTACGTTGCGTGTATGGATGATGACGGACAATTATTGGAATATCAAACACCGGATCGATTGCATTCCGTAACCTT

GAAACGTGACATATATGGGAGAGTAGTGCAAATAACTTCAGATGGCGAAAATATTTTCTTCGAATATGG

MARKER 9473 (SEQ ID NO: 17): C→G
ATAATATATATTTCCATTGATAATATTTTTCATATTATGTGATGTTTGAAATTTTCTGCAATTGCTACATTCCGATT

AAAAACTTTTATTATCCGTACTGGAGAATTTTGCTTTTTTTTGACGGTTTGTTCAATAAGTTGTCAATATATTG̲TCT

GCCTTAGTAAAACCTTTCTAATCTATCCGTTCGAATTGGAAGTTGAAAGTTCAGCATCATTCTTTTAGTGAGGTGTT

TAAGTTGTTCAATAGATATTATTTAGAACGATCTCAATTAAAATCTTCTGAATGATTTTATGTTTTTAT

MARKER 9858 (SEQ ID NO: 18): A→G
GCAGCACATTGCACACAGTAAACTGCAAACTGAATTAAGAGATATTGGGTTGAATTATTTCTAATTTAAAAGGATAT

AATAAATGACTTTGATGATTGTTGATTTTAAGGTATCTCGGAAGACTCCATCAGTCTCAGTGCTCTAGCAATCG̲CTA

TAGGTACTAAAAGAAAAGAAAAGATGTCTCGTTATTCACTTTGAAATGTACATATCAAATCATTTTGTCGTATGAAA

TTAAGTATATTATGTCTAATCGTATCATTCGAAATGAATTTACTGTCACTGTTAGAACTATTTAGGCAG

MARKER 10349 (SEQ ID NO: 19): A→G
AGAGTTCAATCGCCAAGTTGTTCTTTTTCTCGCTCGCAGAGATCAAAACGGTGTTGGCTATACACTCATTCATCAGG

CTGTGATAGACATCTCTTAGAATTTCAGTGCTTTTCTGGATGAAAACATTATTTCTCAAACATGACACTTAAGG̲ACA

ATAGTGCGTGACTTCTTTGTTAACGTACACGAGAAAACAAAACAGATGATGCTTGTTATCTTGGTGATAAATGTGTA

TTCAGAATAATGTTATATATCTTTGCGTGACAAATATCATTTCGTTATACTTCGGATACGCCTTTTTAT

MARKER 10520 (SEQ ID NO: 20): A→G
AACTTTACTTGAACTTTTTTGGTGTTCAATTTTGAATATTATACCAACCATTCAGAAGACTGTATATAGAAATGAAC

CTTCAAGAATTAATCGAAATTTTTATTAAAATCTTTTATTTGAATATTTCATTATTTAAACTCATTACTATTTG̲CAG

TATATTATTAGATCTAATGTAGAAAAAAAAAATCAGATGGCAAAAATAATATCATAGGTTTGTTTTTAAAATTCATTG

CAAAATTCAGTGCGCCGTTCCAGTCGCTCGTAATTACCCTATCCCTGAGCTTTACAAAAAGAATGCTTT

MARKER 10678 (SEQ ID NO: 21): A→T
AGGTATCTAGATAGCATAATAAATTACTACACAAACCGATGGAAACGCAAGTTTGGCGTTGCGTGTTGATACAAAAT

ATTAGAGCCAAGGATGGTATCACATGTAAAACTGCAATTTTGCTATTTGTTTAAAGCAAATAAGAAATAAATAT̲TTC

GTTCTTATTCTTTAATTTATTTCATCAGATGGCTTTGTTATACCATAATTGTAAATCTGTCATATCTTAATTGCGCA

ATAGCCCAAGATTCTTGTATATTCTTACATTTCACAATTTATTTTCTTATTTCTAGTTTTAGAATTATA

MARKER 11676 (SEQ ID NO: 22): A→G
AATAGCTACTCACAGCTTAAGTTAACTAATGGATTCTTGAATTTATTTAAGCGTGTAGTTAAGCGATTAATATGATG

GATGCCCAGAATCGCTTTGTCTTATAGTTTTGTCTCGACAGAAAGGATGCATTGTTGTCTTGAATTTGTTCAAG̲GGA

AAATTAAATAGGTTTCTTTCAATGACTCCTATTAAATTTTTTTGAATTTAGGCTTGCATTGCGTGTTCTGATCCACT

ATTAGCACGTACGGGTATCGCAGTGCCATGTGATGCAGCACTATGCAAAAACCACCTCCATGTCACTTG

MARKER 11933 A (SEQ ID NO: 23): A→G
TCTGTTGTAAGTTTCACAATCCAGTTAATTTAAGCTCAGCTTATTTGAAATTTTCAACAAAATTACGAAAATTACTT

TCTCGGTTCATTTTTTTCAACCACCAAATATTTAGCATAATTGGCCTGAAATCGTCAAAGTTTACAAACTTTTGTTC

AGCAATCTTCTCTTACTCTTACAATAAACATGATTAACTTGTCGTCATACCAATCTCGTTTATAGCAAATTCTTTTC

AAAAAAACATTGCTACAAATTTTATATCGCATCATTTCAACACGCATAATTATTTTTCATATATGAAAA

MARKER 11933 B (SEQ ID NO: 24): T→C
TTCACAATCCAGTTAATTTAAGCTCAGCTTATTTGAAATTTTCAACAAAATTACGAAAATTACTTTCTCGGTTCATT

TTTTTCAACCACCAAATATTTAGCATAATTGGCCTGAAATCGTCAAAGTTTACAAACTTTTATTCAGCAATCTCCTC

TTACTCTTACAATAAACATGATTAACTTGTCGTCATACCAATCTCGTTTATAGCAAATTCTTTTCAAAAAAACATTG

CTACAAATTTTATATCGCATCATTTCAACACGCATAATTATTTTTCATATATGAAAAACCATATTATAA

MARKER 12716 (SEQ ID NO: 25): A→G
ATTAACTCTGAACCCAAAGACTGTTGGTTAAAATAAAGATCTATTTTAGTTATACATCTAACATTAAAGGTTTTCGT

ACGGAAACAAGTAGGTTTGATAATTTTCATGTAACTGTAAAGAACACCTGTGAAAGGGATCAGTAAAATTTGGGGGA

TGTAGCACGGAAATATGAAGCTGAGTGTTTTGTACCCAAAAGTTTTTCAAATCTGCGAAATAACGAGAGGTGTAATG

ATCGTTTTTAACCAAATTTTTTGATTCTAATCCTTCCCACAGTTTTGAAATTCAGTAAGCATTTCTTTT

MARKER 12925 (SEQ ID NO: 26): T→C
TTGCAACAAATCAATAATAAAAGACTTGCGGCTAACAATATATTTGATTCTTTTTTACCGTTATTATTATGACAGGT

AATAATAGTATTACAAGCATATTTGTAGGTGTCAATTTTTTCAATTCAAATTTTCTTAATTCATTATTTCTTCCTTT

CCTTAATAAATAGTCTTTCCATTTAAGAATTAACTTTTTGAAATCTTTAATGAGAAGACACAAAAGATTCCGGATAA

TTTTGCATCATCTTTTCTATTTCGCGTTAGTATTTTATGTTTTCAACAGATTTTTATGATTTAACTATA

MARKER 13063 (SEQ ID NO: 27): C→T
GATAAAATGGGTTCTTGTCAAGCTCATTTGGCATATCTTCGTCTTCTATATTTATATCCTTTAATATCTTCTCTTTT

TTCAAATTTTCCTTCCCGACGTTTTCCATATCGACCTCTTTCTTCATAAATTTATCTTCCTCATTTGCCTCATTTTT

TGACTTTTCATCCGTTTCATCCTTATTTTTCTTTTTTTCATCTCCTATTTTACCTTTTCCTTTATCAACTTCTATCT

TAACTTTCTCAATGTTTTTTTATTTTCTTTCATCTTTTTGTTTTCTTCTATTGACATACTATAACAAA

MARKER 15000 A (SEQ ID NO: 28): T→A
TTTTACGAACAATTATTTCATAAAAGATTCGTATTTTTGATTAGTTTTTAAGAATTTTTTTTATTATTTTTAGCCA

ACAAATATATTTTTCAAATTGTTAAATTTGAAATTATAAATTTCAACTAAAAAAAAGCAAAAAGCTAAGCCAATAG

AAATAACATACATGTGTAATATAAAATATAAAGTATTCGAAATGAAAATCAAAGTTTCATAACAAAAAACAAAAAAT

ATTCTAACCTTTTAGATTTCATCAAAACTTCACTAAAAAGTTAAATTTAAATTTTCAAATTGTTATACA

MARKER 15000 B (SEQ ID NO: 29): A→G
CGAACAATTATTTCATAAAAGATTCGTATTTTTGATTAGTTTTTAAGAATTTTTTTTATTATTTTTAGCCAACAAA

TATATTTTTCAAATTGTTAAATTTGAAATTATAAATTTCAACTAAAAAAAAGCAAAAAGCTAAGCCATTAGAGATA

ACATACATGTGTAATATAAAATATAAAGTATTCGAAATGAAAATCAAAGTTTCATAACAAAAAACAAAAAATATTCT

AACCTTTTAGATTTCATCAAAACTTCACTAAAAAGTTAAATTTAAATTTTCAAATTGTTATACAATGAT

MARKER 15709 A (SEQ ID NO: 30): T→C
TCAAAGACAAAATGAAGAACTTAACAAAAAAAAGGCCAATAAATAAAGGCTATTTCGTGAAAAATCTAAAAAAAAAA

AGATCTGTTCCTTTCGAATCAAGTGATTCTTCCTACTACATTCGTGTTGTAATTCTTACTTGTATACAGTCCCCAGT

TTTTCGACGATAAAAAACATTTCGATAAGTGAGTTTGAATTAATTGAATTTAAAAGATCATAAAAATAAAATCAAA

ATAAAAAGACCAAAATTAAGTCTGATAATTCCAGAAAACACAATAATAAATATACAAATAATAAAAACT

MARKER 15709 B (SEQ ID NO: 31): T→A
AAATAATTCACTAATTTCTCATCATCAAATTATTTCGTACAATCGATAAATCAACGATTATAATAGCGAAGAGAATG

AAAATTAATGTGGTGCACAGTATACGGACCCCATATACAATGTTCAACAGAGATGAACATTTTTTTTCTATTAAAGT

TTTCTGTTCGGCGAAAGAAAGACACTTTCTAACGATGCTTTCCTCCCAACTCCCCTTGCAATGATAGAGGATGCAGC

CAAGATTCGTCGACTCAAGCAGCATCACTCAACCGGCCATCACTTCGGGACCTTTTTCCCTGCCTTTTA

MARKER 17333 (SEQ ID NO: 32): A→G
CATTGCGAATGACCGCTATGGAATATCAATTAGCAGATATTAATCGTGAATTAAGCACATTGGTGGAATTTTTACGA

CCAAATCGAATTTCAAAAAATGCTACACTTGCAACATCAGCAACCATTGCAACATATAACAGTACTTCGATGC<u>G</u>TAA

TGTAAAAAAGAAATGTAATGCATCTGAAAGCTGAAAATTCATCTGATATATTGAAGCAAAAGGTAAGATTATTTTTA

AGATATCATTCTTGATGCTCTCATAATTTCTACATCAAATTTAATCAAACGATTCATTTATGTTCATTT

MARKER 18110 (SEQ ID NO: 33): C→T
TTCTTGTTGTACCTATCATAGATGATAACTTAAGTACCAATAGCAATAGTGCAACGATGCAAGGATTCTGATTAATG

ATTATAAAGTTTAACCAATCTTCTTCATTCCTTCTAATCAAGAGAAAAAAAATGAGAACATTTTTATGACA<u>T</u>TTG

AAGAAAGGCAATTTATCGCTGAAAATTCTACTGCGATATGGAAGTATCAGATAGAGAAATAAATATTAAAATATGG

ATTTCATACGAAAAATGATAAAAGATAATAATTTACATTTTGGTGCTTTACTGATATGATTGGAGTATT

MARKER 19999 (SEQ ID NO: 34): T→A
CGATATTTTTTGGACGAATCAAACCTTTTTGGGAAATCATTTGATGTCACAAGCATGGTTTGAGAAATTTTTTCCG

AATTAGTTCTGCTAAAAATACTCCAAATGAGTCTAGTGGAATTAAGCTAAGCACCTTAAGTAAGTTGAGAAAA<u>A</u>CGT

TTCCATTTGACTAACAAGGCTAGTATATCGACATGAGACAGAAATGGTTATTACTTCACTCACTTCATGAAGCGAAT

ACGAAATATCTGTTCACTTTAGTTTCAATCTACTATTTTACCAATAAACGTGTTCTTTTCCGGATAAAT

MARKER 20570 (SEQ ID NO: 35): T→C
TCTTAATTGATTTTCTTAACTCGAAACACTTGTCTTGATTACTGTGCTGTACTTTATCTTATTAAATTAAATAATTT

CCATGACCACTTCATACCATTGACCATCAAACTTTGATGAAGTTTATGTGTGAAGTGCCAAACAATCATTCAT<u>C</u>CCT

TCAGTTTAACTTATTGCTGGTCAAATTCATAAAAATGCAAATTATCAAGCAGATAGTAATTCAGTGAACGTAGCGTA

TTCTCGAAATTTCTTTCCTTGTATTTACCTTATATAGAACAACGTATATTTGTAGCATATATTCAATAT

MARKER 20587 (SEQ ID NO: 36): G→A
TTTCTGAGTTTGCGTTACAGCGCCAAATCTTCACGGAGATAGATAAAATACTTATCGTGAAATTTTGGCGCCATGAT

TTAAAAAACACGGAGATAAAAATAAAATGCTTATCGGTGATAATTTAGCGCCATAATATGAATGAATTGAAAA<u>A</u>ACA

ATTTGAGTAGAAACATGACATAGAGTTTTCGTTTTCTGGCTACGAAAATGGATGAATTTTTCTGGAATCGAATTCAG

TCAAAGAAATAGGAACGTTGTTACTAAATGATCGAAAAGCTTTCTAAAATTAAATTTATGACGTCTAAG

MARKER 20698 (SEQ ID NO: 37): T→C
ATCTAAATCTTCGTTTTATAGTGGTAAGACTTCCATTTGCTGCATTCTTGCAAATTAAGCTGTTGAAAATACTTTTT

TTTTTGATAGATTTCCAATTTAATCATATTATAAGAAGAATTAATTTCGAATAGAATTTTTAAATCATTTAAA<u>C</u>TTT

AAGTTTTAAAACTAATATAAGTTATGCAGATTTCGCGAAAAAGTCTCATTTGTTAATTCAATTATTCCAAAATGTAA

TAATTTTATAAATTCAAATTTAAACTACTACTAACTTCTGAAGTCAGGAGCCAGTAGCAACAACGTAAT

MARKER 21554 (SEQ ID NO: 38): A→G
AACTTTACATTTATATTCAATTTTTTTTTATTTTGTTTGTTTTTAGAAATTTGAAAATGGGTACTAATCAGTGTCAT

TTGCAGCCTCTTAGACCCTCTTTATAACGACCGATTCGATGAAATACGTCATCAATATGCCAGTTTATTGTTC<u>G</u>GGT

GGAGAATGTTTTCAAAAGTTGCTGAAGTGATGAAGTATAGTGAGAATGCACCTTATTCAGCACCATTAAGAAGTAAA

TTTTTGCTTTGGAATTTGACAAAGACAAAGCAGGAAGTTGACAACGATGTTCTGATGAAACGGTTTCGA

MARKER 22174 (SEQ ID NO: 39): A→C
GTCTATTTTGGCTGTCTTCTAATAATTCATTTTGTAACCTTTTGAAATATGATAAATGTAGAAATTTTTTCTTCCTG

GTCTATAATAGTTTAATAATGTGTTGTAGTAATAGTTTTGGTGCCGTTGAAATATTTCAATGATATGCTATCG<u>C</u>AAA

ATTAGGAATTCAAATCAAGGTTACAAGATAATTCAAAAACAAACAACGTAAAAATGAAATAATTTCTTCTTCTTACT

TACCAACAGGCATATCATCATCATCCTCAAATTCATGACTATATTTAACATTGTCATATTTGAATAATC

MARKER 22254 (SEQ ID NO: 40): C→A
CGACGCAAAATCTTTCAAATTGTCACCCAGTTCTCTAAGTGATTCCAATGATGTTGGTAAACATTCTGCATGATGT

ACCGGGTAATGAACTACCAAGTTGTTTTTTGCTTTTAATACAACTCGCAAAGATTCTGAAAACCATGAAATTA<u>A</u>GAA

AGATTAAAATAATCTGAACTCTTTTTTTCATTTTTCCTTGAACTTAGCAATATACTGAGTTGGATAAAATTTAGAAA

CGAAATTTCGCAAATTTATTCAGTAAATTCAGGAAAACTCGGTTTCGGTATTCTAAATATAAATAGATA

MARKER 22259 (SEQ ID NO: 41): A→G
GTTTCTTTGGTTTATCTCAGTAAGATTTGGGCGGAAATTTCAGTTATACTTTTCATTTCCATGTGCTGTTTTAAATT

TCTTCCATATTAGTATAATTTTCAAATAATTGTAGCGTCACTGGTTTATTTAAGGATAACAGGTTGGACTGCAGTGG

CTGAGAAGTGTCTTGCCGGTCAATTGTTTGTTGGTGATCAACTTGTACGAGTTACTGATATCGACATATATAATACA

CGGCAAATTCCATTCGTTTTCAGTACTGCATCAAAAACGGGATTATCGGTACTTTGTAAATCGCAGTAT

MARKER 24708 (SEQ ID NO: 42): C→T
GACCCCTGCTCACAAGGCAGTTCCCACAGACAATCACACATCTAATCACACACATCAACTCATCCGACGTAGGCTAT

CAATAAGGAAAATTGCATTGCTTTATCGTCTAACTGTAATAAACATCTACATAATGAAATTATTTCGCCACTATGAC

AACTAATATCGCCCAATGCAAATATTTGTCTCAGAGTTATTCCCTTTTAACAGCTGTTGAACGAATAGATAGGACGT

CATGTGGATGATCTACTTGTTTCAAAGGTTGAGGTAACACATGAAACACATGAAAACGGTAATTTAAAA

MARKER 25276 A (SEQ ID NO: 43): A→G
AAAGAATGGTCAGCAAGATGTGGAAAATCGATTACTATAGTTGAAGTATGAATCGAAGAGGTTTTTTTAAATTCTAA

GAGAACGAATAATCGGCAAAGAGAAAGTTGAGTAACCTTATTTTGCCTTGTTTTCAGTCAATTTATAATATGCGGTT

AATTGTGTTAAAGAAAGTACAAGGTATGAAATCTAAGCCAAGAAATAAGAGAAAACAGCTAATGATTATTTCTGCAT

TTTTTCTTTTTCGACACAAACTTGGAACCAGAATCAATTGAACTAGTAATCAGATTTTGATTATTGCTT

MARKER 25443 (SEQ ID NO: 44): T→C
TTAGATTTTGCTGAAGCATTGTTGGTTAGATCGATGAAAATATAATTATGAGAGATTTTGTTGAAATTCAGCAACAA

AATTATTATTCATGTCTTCATGCTGTCAGTTTTGTTTTTATTCTTCTTTGACATCGGTTATATTTTGTCTTCCAA

CAATATAAAAAAAAAATTATAATCAATTGGTAATCAAATTAAAACTCTAATTGTTAGCTCCCTAAATCAGCTTTAAA

AAAATAATTGCTTAATTGGTATTTGCTACTATTAGCAAACTGAAACTATCCTTTTCTCGAATGGTGAAC

MARKER 26447 (SEQ ID NO: 45): G→A
ATGAGCTGATATTTGATATGCATATTAAAAATAGGGTAAATTACATTAAGTTAGATATCGTTCGGATAAATTAATTA

GAAAAAATGTTTACCAATTAGATCGCAATGATGTAAAATTTCACGTATTTTTATTCTTAAGATTTATTTGCAAAATT

CAAAAATATGTCTTATGAAAAATAATATTTCTGTGTAAGAACAAGGGACCGATTCACTTGATTTATTCGCAAACAAT

CGAAATTCAAAATTAGTAATTTTAAATATTGCTTTATTCAAACCATACCAATAATAATTTGAGAGATTT

MARKER 26730 (SEQ ID NO: 46): A→G
ATTGATTGATTCAAATAAGAAATTTAAATTATTTCCCCTTTTTTTCAAAAGATTTAACAAATATTATTTATTTGATC

TCCTCGTTCGTTCTTATCTTTTTGATTATCAATCCATCCTCCTCCATCATATAGCTAATTTATTTTTTGCATCGTAA

ATCAATTGATGTATGATTGATTTCTTGATTATAAAAAGTTAGAAGAATTGAATTGCTTAAATTTAATTATTGATAAT

GAAATATTATTATATTTCAAAATGATACGAAGAAATATGACGATGATAAGAGAAAATATGATATTTATC

MARKER 26974 (SEQ ID NO: 47): C→T
TACGATAAGTTATTTTATTTTACACATCTCCATCCTTGACTAGTGTCCGTGCCGACTGTCGGACTTGAACCGACAAC

CTACTAATTACAAGTCAGTTGCTCTACCCAATTGAGCTAAGCCGGCCATCTAGAATGTGCGACCCCGTCGTGGTACA

TCTTCTATAATCGTTTGGTATTCAGGACTCTCTTCTTTCGTGGGTGGAGGATCTTGATACAGTTGACTATTAAAAAT

AGGGCCTTTGTTAGTCTGTTACAACTCATAGACAAAGGCGACAATTTTAGCTTACATCTTACGTTATGC

MARKER 27080 A (SEQ ID NO: 48): A→G
ATGGTAGAAAATTATATGAAAAAATATCATACTAAAAATATAACAGATTGTTATAAGGTATGGTTTAAGAATTTACA

ACAATTGATTATTTATGATAAAAAAAAAAAAGTAAATCAGTGAATCATTAAGATAGTTATGATAAGCAGTTTGTAT

TCGGTAAAGCGAATGATTAGAGGAATTATGGGACGAAACGTCTATAACCTATTCTCAAACTTTTAATGAGTATGACG

TGTCTTGCTTGCTTAAAATTATTTCAATGATCATTTCACTTTACCAGTATGATCATGATTAGACTTGAA

MARKER 27349 (SEQ ID NO: 49): T→A
TTAGTATCGATATTATCACAAATGATATCACTTTCATCAATACTGGATACGATTTTATTAGTATCATAATTTTGTGG

CTCGCATTCCGAAAGTTTTACACGTAGAAGATTAACCTGCAATATGATTTATTTTATCATTTTCGAATATCCAACTT

-continued

TGAAATAATTCGAAAATGTTGAAAAATTTTGAAAAATTGTTAACAAAATATTACAAAAATATCAAATGAAATTAAAT

AACTGTCCATTTCAAAAAAAGAAGAAAAATTATGAAATTACCAATTAAAAACAGGACTTATTAATTAAA

MARKER 27461 (SEQ ID NO: 50): G→T
TGTGGAAATAAAGTACAATTAATTGCTGTTCGCTTAATAATATTATTTTCATTCTTGGCTTTTTTTTCTTTCCCCG

TGATATTATAAAATATAGTTTTTTAATTTTAACAAATCGTCATAATTATTTAAAAAATACTGAGGTGAGTAAA<u>T</u>GTA

ATTGGTTGCTGGAAAAAAAGTGGGTGATGAGAGGTGAATGAAAGCAGAATAGTTTATGATTGCATCAAATTTCCTCC

TTAATCTGTGATTAAAATCAAACAAAACCCGAAAAGTTTCTTCTTCGCCTTTTTCTTCTCTTTGTTTCA

MARKER 29128 (SEQ ID NO: 51): T→C
CGAAATCCGCCGCGTGCATTACTTTGCGCTTGTTGATTACGACGCATTTGTTCGTCGTTGATAACCTTATCAATCAT

CATACGTCCGTTACGTATGCAATCAACATCGCCAGTTAGGCTGAAATCAAATGGATGGCGATGATATCAAAAA<u>C</u>AAA

AATAAGGAGTATTTGCTGAATCATTTCTTTTTCTGTATTATTATCAAAATTTTCTCCTTTCCATTGTTTCCTTCTTA

ATCAAGTGAATGCTCATTTCATTTTGAAATAATCCAACGTAATAATTCCCCATATTCCCAATTACTTTC

MARKER 29168 (SEQ ID NO: 52): A→G
AGAAATATTAAACTTTGAAAAGATGTGACATGTTCTGTAACAAAAGCCCAAAATTTCGACTGCTGCGGCTTGAAGTA

AAATTTTGGAATATGCTACATCAGTAGTGCAACAGATGGTTCGATAAATAGTGGTAAGTGATGGGAATCCTAG<u>G</u>AAT

AGATGGGAATTGTATTTCAGATATAAATTTGATGCATATTTTCATAGTTGATTATATCTACGATCACACGTTGAATA

TTCTAAAAGCAAACTGTAATTAACTAATTGAATTTGAAAATTTCCAAGAATTAAAATTGGTAACAAAAA

MARKER 29455 (SEQ ID NO: 53): T→A
ATTGTCAGGAATGAGAAGCAAGTTTTGGATACTTAAGGGATGAATGGAACACATACATGGCAGAAAATGTTAGTAAT

CAAACCATTTAAATTACTTAGCCACTATGCTAAACTTTCTAGAAGTATGGTTGAACGTTTAAAAACCTTCGCA<u>A</u>AAA

TTGTATTAGATTATCTTAATCTTCCCTACATCAAAACAGAGAATTTTTGTTCTACGACGTGAGTCTGCATGTATTAA

GGAAGTTCGTATCATGACGTAAATATCCTGAGTGATTATTGAATTCAGAAAATGAGCTTTTTCATTTGG

MARKER 29816 (SEQ ID NO: 54): G→A
ATATGAGTGTTACATGTGTACGTTACATGTAAATATTATATGTTATATGTAAAAATGTCATGTATAGCATCTATTCA

CGTGTACGTACACGTGTATATACATATACATTGATACTTAATACGTATACGCATGAATGAACAGATATTATAT<u>A</u>TTT

ACGTACACTAGACTCACATGTACCTCTGTATACGCATACATGTACAGATATATGTTTGACATACGTAAATTCATATA

TGCTTTTATTTATGCTTATATTAATTGTCACATACATGCCTTATATTTTCGTTGTTATAAACACATAAA

MARKER 30575 (SEQ ID NO: 55): T→C
GAAAATAAAATTAGCTGAAAATATATGCGAGGTAAAGCACACAGAAGAATTAACTTAAGGTAATATATTGTAAGAAT

TTTTATATTCGGCGCACCTAATAATTTTTAGACCGCATATGCCCAGTATTTGAAACTGGTAGCGCTGTTCGTA<u>C</u>TTG

CTGTTGTCCATGTTATGTATATGATACCATTCCTAAATACTTTTGCGGCTGTGGTTTCCAGTGTTGATGTGACTGGT

ATGATGCCTAACACTGGATCCTTCCATCTGCGGCATTTTGTTGAAATTCTTATTGATGTGAGCTGTTTA

MARKER 30991 (SEQ ID NO: 56): A→G
CAACTGTGAATCATAAACATTACTTAAATTAATGAAGCTAGTTAACGACAAATATATTTTTTATGTATCAGTGCTA

TCATATAACATAAAAACTTACTTTCATTAATAAATGAGCTCAAATATTGACTTTTGTCCAAAATGCTCAAAAT<u>G</u>TCG

TCATAATATTTGAAATGAAGATAATTTCACGCTTTTCGAAGCCTCCTCTCACGTCTTTTAATCTTCTTTTCTTCTTC

TTGCTCTAATGGTTCTGCGAAAAACCACGGTGCAATAATCACTTTCCATAATTTATACAGTACATAAGC

MARKER 31796 (SEQ ID NO: 57): A→G
CTGCTTAACTCTTTTCATTTTTCAGAGAATCTTCTCTAAAATTGTGAATTGATCCAAACCAAAGAATATGGATAATG

TGATTCGAATTCCTGGAATTTAGATTTTGAGAGTTTTGAAGTTTTTAAAGAGATTGAATTTCTGTGACCTTCT<u>G</u>GTA

TATTTGATGTCATTTCGGGATGCGTATTTTTGCCGAAAATTTTTGGCCTCACTGCAATCTTGTTAAAAGTCAAAAA

ATTCAATCGTAGAATTTCGGGTTTACCTGATATTACTGGAAATCTCTGATCTTTGTTCTAGATTGCTGT

MARKER 32164 (SEQ ID NO: 58): A→T
ATAAAGAATTTGCAACTCTGTATACCTTTTTGCAGTGCAAAAGCGGATGAATTCTTCACTGCAGTGTGACAGATTCC

TTTGATAAAATTGCTTCGTTCTTATGTAAACTTGGAAATTCTCGGTAGTTATGCTTTTGCTAGTTGAAAATGT<u>T</u>CTG

CTCTTGTAAAACATGCAAAAAGAGATTATCTTTGTTCTATTATGGAAAGATTCTTTTGAAATTTTGACGACTGAGAA

GACAAATTTTATCCCAACTTGTCATCTGCAATAAAAATTTTTCCTGACCTGTTTCTTAACCTTCCAAGT

MARKER 32223 (SEQ ID NO: 59): T→C
AAAATCAAATCAATATGATCAGATAACTCATACTTATCTTACTGAAAATTCCTCATTCAAGGGAAATAAATAATTGC

AATTCTTGATTCCGATCATGGATGATTTTCAAGCAAATTACCAATGATATCTATCGATAACGATTACAGCATACAGC

TATAACTTATTATTGATTGAATTGATGAAAATAATTTTACCAGAAATTTATCAATGTTTATCTCATTGCAGTATACG

ATGTTTAGTGTGACAACACTTTTTCTTGGAATAATTGTGCATAAATCATTGATTGCATTTAGTATTGGA

MARKER 34439 (SEQ ID NO: 60): T→C
TCCTGCCCACATTCTTTCTACTTTAGATAATCAACAGGAGTTAGTTGAAAGAGAAGACTAGGAACAGTTGCAACTTC

TGAATCTTTCTGACTTTCTTTCGTTTTGTAAATTATTTATTTGTATAAATTTAAAATTCGAAGAGAAATAATCCAAG

GTCCAACTTCTTTTTCTGTTAGTTCTTGCGAATGCTCCATCAAAATGCAAAAATATGATTAGAATTCTGATGGAAAT

TAACAAAATCGATTAGATAAGAAAAGTACAAAACAGAAACTAACTTTTTCTCCCATTTTCATATTATAG

MARKER 34903 (SEQ ID NO: 61): T→C
TCATTGCTTTAATACTTTTTAACGAGAATTTTCTCGATCAAAATAAGATCTGCAATTGATATACGTCAATAAGCGAA

CATTAGCTGTATTACACGCTAATATTCACATATGATGAACGTTGTAAGCGTCATACATCAACATATATCCATCCGAT

AAATAATGACCACTACACATTGCTACCAACCATCCTATCCCGCCACTATTTGAAATGAACTGAGAAGGAGTTATCGA

CACAGGCTTCCTAGCAACCAAACAAAAGACGAGACAGATGAATAGATAGACAGACAGACGAACATACAA

MARKER 35336 (SEQ ID NO: 62): A→G
AGATTCTGGTTATTATTGTATTTCTGATTTATTTAATCCCAACTTAAAGATTCATTGGCTATTGTTTAGCATCTATA

TCAATTTTATAAATAAATAGTAATACCTGATGAAAAGCAATAAATAATTAGATGCAAATTTTAATTAGATACAGTTT

GATGGAAAACATTGAAGCCATGTACAACTAATTTATGCATGTTGAATTATGCATGCATAATTAATTTATGCATGACA

GCAAGTTTGGTATAAAATTAATTTTGTATGAAGATAAAATTTTATAAATAATGATAATAATGCTGGTAA

MARKER 36040 (SEQ ID NO: 63): T→C
ATTATTGAAAAGAATAATGTAGCTAATTAGTTGAAGCTGTTAAAAGTAAAGCTAAAAGATGATGGAAATTATTCGT

ATAAACATTCTTTGTAAACAAACAGTCATTTCTGTGAATAAACAATTATAATTATAAACAATACTTTTCAAGACAAT

AAAAAAATTAGGAAGCATTGTTGTGATAATCAATAGTTGATAGACTGTCAATGTATTTTATCAGTCGTGCTGCTTT

TTTTCCCTTTCTTGACTCATTTATTTTATTATTTATTGATAGAATGTCAATATTCTAGTCATTTGTTAT

MARKER 37881 (SEQ ID NO: 64): T→C
ATCTTAACTTGCTTTAAACAAATAAATTAAAACAGCCCAATGTTCCAAGAAAAAAGATAAGTTAAAGTGGGGTGT

CCAAAAATTTATGAATTGAATTGGACAGTTATTCAGATCCTGAAAATACGCTTCTCTGATCACTGCAAATATTCCCG

ATAAATAAGTGAACATTAGGTTAATCTTAATTTTCCCTTAACTTTCCTTAGCCTTTTTTAAATTTTTGGATTATTCA

AGCATTTTTATTGCGGTATCGTTTTTGTAAAAAAAAAAGTATAATTCAACATTCAGGCTCGACGTTATG

MARKER 38622 A (SEQ ID NO: 65): C→A
AATTAATAAAAGAAAGGAATACGATAAAATATCTATTTTTTGAAACTAATCAAACATATTCCTCACTGCTCACCGG

ATAGTTGCTTTCTAATTTTACATTAAGAAATATATTTTTTTTTTCAATAAGGAAAGTTATGCAGACTAGGAGAATT

CTACTCTGAAGAAGAGATAAGCATGTTAGAATTATTAAAATCTATGGAAATATCCTTAAAAGAATGCCTATAGTAGC

TCTGATTTCGAAAAAAAAGCAAAAAACAAAATAACAAATTCTGCTCAATTGAAATAAAAAACTTTCCT

MARKER 38622 B (SEQ ID NO: 66): C→T
TAAAATATCTATTTTTTGAAACTAATCAAACATATTCCTCACTGCTCACCGGATAGTTGCTTTCTAATTTTACATTA

AGAAATATATTTTTTTTTTCAATAAGGAAAGTTATGCAGACTAGGAGCATTCTACTCTGAAGAAGAGATAAGTATG

TTAGAATTATTAAAATCTATGGAAATATCCTTAAAAGAATGCCTATAGTAGCTCTGATTTCGAAAAAAAAGCAAAA

AACAAAATAACAAATTCTGCTCAATTGAAATAAAAAACTTTCCTTCAACTTCCAGCATCACTGCTGTGA

MARKER 38622 C (SEQ ID NO: 67): C→T
AACTGCTAAAAAATTGAAACTAGTGTTAGATTGATAAGTGGGCAGATTAAAACCAATTGTGTTATTGGCCCGTTAAT

TAGTGACTCTGAATAGCTATGGCGAATCGTATAGTGTTGTACCGACGACGTATCTATCAAATGTCTGCCTTGTTAAA

TTTCGATGATAGTTTATGTGCCTATTATAGTTGTAACGAGTAACGGAGAATAAGGTTTCGACTCCGGAGAGGGAGCC

TGAGTTGCCACATTCAAGGAAGGAAGCAGTCGCGAAGATTACCCACTCTTAGAATGAGGAAAGAGTGAC

MARKER 38622 D (SEQ ID NO: 68): C→T
GAAAACTAAGAAGTAAGTGAAATTTCTAAGTTCTTTCCCAGAAAGGTTAGATCCAATATTTGTTTTCATTTTAGCAT

TTTTATCCAATGAAAAATGTGCCCAATAAATACTTGTATATAGTATTGCATTTAAAAACTTCAGAAAGCACAATGAG

ATCTAAGCTCAGAAATATGACGAATACCAATCCTTTTCCTAGTCTTACCGCTTCTTAACTTTTGTGTCGCTTTATAA

AAATTAAAAATAAAAAGTTGAACAATGGGAATTACATCATTTTCATCTGAATGGTTTATTTCCTATTCT

MARKER 39492 (SEQ ID NO: 69): T→C
CTTCCCTAGCTATGCCTTTTCGTCACTTAAGCTTCNNNNNNNNNNNTCTAGCTACGTATCGTTATCATTTATGCTTCT

TTAGCTACGTTTCTCCATCATTTATGCTTCCTAAGCTACGTATCTTCATCACTTACGCTTCCCTAGCTATGTCCTTT

CGTCACTTAAGCTTCTTTGGCTGCGTGTCTTCATCATTAATCTTCTTTAGCTACGTATCGTTATCATTTACGCTTCC

TTAGCTACGTCTTTCCATCATTTATGCTTCCCAAGCTACGTATTTTCATCATTTATGCTTCCTTAGATA

MARKER 42291 (SEQ ID NO: 70): G→A
GATCTTAAAATTCTATGAAACTTCTTCTGCATGGTATTGTTTCCAACAGAATATAATGACAATAGCAACAGTATTGG

TTATATAAAAATATTGACTGCAGCAGGATTATATTTCAAGTTCTTTTAATTTCATTTATTTATTCTTTCATTTACTT

TTACTGTTTTTATGTTTTTCTTCTTTAAAAAATATGATTTCTCTCACTGTTCTCTTTCATCTATCTATATTTATTTG

ATAATTGCTTATATGATAACTAGCTAAAGGGAAATAAACTTTCAGTCATCATAGCTTCATTTTAGTAAA

MARKER 42411 (SEQ ID NO: 71): A→T
CTATACTAATCAGTCCACTATCCATTTTTAGGTTGCAAAAGTTGCAATGACGGTTTGATTTCATCCTCCAATGCAAT

TTTGAGTCTCAATCTCGAGAGATAGATCGATCGCTTTTAGCTTGATTTAGCTTGGTTAATGTTGTGAGGGATATTGG

GCAGAAATTCTGTCAAGCGTTACTTAATGAAATAGTAAATGATCACTGATATTTATTGTTAATGATACTTGAGCTCT

CTAGATTATGAACTGGAAGGTTTTCGATAGAAATAATCGATACATATATTAGAATCGACTTCTTTTTTC

MARKER 45689 (SEQ ID NO: 72): A→C
TCATCTTTTTCACATTTCATTTAATCATCATTTTATCAATTCCTATTTTTAAACAAATTCTTTTCAAATATTCTCTC

TTTCCTTCTCTTTTTGTTTTCCGCTTATTCATTCTAATGATGAACAGATGTAGAAAATTTGCATTCTATTGCTCACT

ACAATTTTGAGTAGAATATATTTAATTATTTGATTCGAGACAGATGGTTATAGCCTTTAGCTTCAGCTTCTCGTTCA

AATTAAGTACTTGTGACCTTTCCAAGTACCATTAAAGCTTTCCTGCGTTTCCTAATTAGAAAAAAAAGG

MARKER 45719 (SEQ ID NO: 73): G→A
GCATTTTAAGTTAAAAGTATCACGCTGCATGACACCTCACGTTTGCTATCTCAAATTGAGTAGGTTAGAATCTTTTT

TTGGCTACTATTCAAATATTAATAATAAATTGCTGCAAACAGATTTCACACCGGAAAAAAATTAAATTTTTCTAGCA

ATGTTTTAACTCCCTTATTAAATATTTATAGAAAATCGACTACTTAAAAAGAATTGACTAACATTTCTGAATCTCTG

CAGAGATTTATAGATGGATTAGCATCCTACAAGTTTTTATCTTTTTGCTATATTTCCATTATTTTTTA

MARKER 46063 (SEQ ID NO: 74): T→A
GATAAGACGTCTTATTTTGTAATAATTCAAAAATTAATTAATATAGAAGTAAGATCTTGATAATAATTAATATGCTC

AAATTTCTTAATGAGAATATGTTCAGGATGAAGATGAAGTGAAAGAAATTGATAGATTGAGGAAGCAATTGCTAATT

GAAACAGAACAGCTCGTTTCCAATTCTCTTAAAGATTTACTGAAGAAAATTTATTATCCACTTGAAGAAGCTATTGA

TCTCAAAATTCATCAGAAATTAATTCAACAAATTGCTGCCTTGTTGAAGTGTATTAGTATCTTGGATAA

MARKER 47481 (SEQ ID NO: 75): C→G
ACCGCAAAATACCTAAAAATTTCTATAACAACGATTAACACGGCCTCGAACTGGAAGCATATTAATCCATGCGTGGC

TCAAACTTCAATCATAAAGACAAGATCTAGAGATCAACACAAAATGGTGAATTGTTACCCTATCGTTGCTAAAGTTT

GAGAGAAAAAGTGCTAAATCAAGTAGTACACCAAATTTAGTTAATATTAAGAAATCAATTTAGTACTGAATTTAAA

CAAATGAAATTTTACGATAAAATAAAAAAGTACCTGATCAAACAGCGTCCTCCCGTTATTCCCATTGCT

MARKER 47722 A (SEQ ID NO: 76): C→T
TATAAGACTAGTAAACAGATCGTAATATAATAAATATCGATTTTATTTTAAATTTTCGAAAACTTCCAAATCTATCG

ATATGAAATTAAAGATCAATTTTTAATTTCCATAATATATTTAGATTCTATCCCAACATCACTCATCTTTATGTCAA

CTTATTTAATTCTCTTATTAACATTATATTTCTTGTTTACAATGATAAATTTTATCAATTTTCTAATATGATAGAAC

ATCTTCATCATCTGAAGATATGCTTTTCTCATCTTTGTAACAATTCGTATCGCTTCTGATTTTACTTTC

MARKER 48750 B (SEQ ID NO: 77): G→A
GTTTTATTATTGCTTATTGAATAGTGATAATAACACTTTGATATGATATTGTTTTGTTGCGATCATTGTATTGATTA

TAACCTTAATTAAACGAGGATATTATGGGAAATGTATTTATTACAAAATTAAATATGAAAGGTTGAAGTCTTGACGA

AACTTTCAAACACATTTCTCGAATTTTCTCTGCAAAAATATCGTTACGATTTTTGGAAATTATGAAGTCCAAGAATT

CAATCGAGAGTTCGCCATGTCACTTTGGCTAGTTTCGTTTGTTTTTAATATTTCAATCAAAAGTCAATT

MARKER 48750 C (SEQ ID NO: 78): G→A
CCTTGGATATTGTTCTTGACATCGTTGATCAGAAGGTCACCGTAGTGTTCGGTGAGCGAGATGGAATTGGACTCAGG

TTTATTCTCCGTTTTTTTCATGTTTTTGAATTTTAGAGAGAAAATAATGTTTGTCTGAATGGTTAGCAAACTAATTA

GTTTTTAAGTTATCAGGAACTCGAAGTATCTTCTTTTGCACTTCTTTAACCTTTTTCATCAAATTTTTTAACAGTAA

CAAGATTTTTTGAGAATTTTCAAAATATTTTTGACTTCTGATGATATTTGATGAGAAAACCATCACTG

MARKER 48790 (SEQ ID NO: 79): A→C
AGAGTATTATTATACATGATGATGATGATGATGATGATGATGATGATGATGATGATATGATGATGATGATGATGATG

ATGATATGATGATGATGATGATAATGATAATGATGATGATGATGATTAATTGCTTATTTTTAATGATTGATAACTTT

AAAAGAAATCATTGAAATTTGATCGAATAAAAATTTTCTTAAAAAAAGCATTTGCTATTTATATAGTAAACCTATAA

AAAATTACTTATTTTTATTACTAATATTCATTTGATTGTATGAAAGAGAAGAGAAAAAAAACCTTTGCA

MARKER 49731 (SEQ ID NO: 80): T→A
TGGTATCACAGCACTGGGTTTAATTTCAACAATCGGTTGACGATCTTTTCGGGATATGCCTATACCCAGAAATGAAC

GTATGCCAAACGATGGTATGTTTGATGCAACAGACGACGTCAACTTAAAATGTGTTTTTTTTCAAAAATTCAATAT

TTTTAGTTTAAAATTGCACGTCAGTAAAAATTAATTCATAATAAATCTCTTTGATTTCTTCGTTCTCCTTTTTTTC

AGAAAAAATTGAAATTTTACATACCTGATTTCCAAGAGCATATAAAGCATCACTTAAAGCATTCTGCGA

MARKER 49824 (SEQ ID NO: 81): T→C
TCCTTTTCATGATTTGTAGCTAACCAATAAGATGTGTATATGTTCATATATTTACTCTCCCCTGACTCTTTTACACT

CTCATTCTCTCATTTGTTCATTTAGATAAGTAATATGCGCCTTTCTCTTCCTGATTCTCTCAATCTTTCATCCCTTC

ATCTCCTCAATCTTTCTCCCATTCTCTCAATCTTTCCTGCATTGCATTCATTGATGAAACACGATAGTATTAATAAG

CATAATTTGATAAATTGAAATAATTTTTTTTNNNNNNNNNNNTCATTCTCTCAATCTTTCCTGCATTGCA

MARKER 49904 A (SEQ ID NO: 82): A→G
TTTGAATTAACAAAATATTAACAATTACAACTATTTCGGAATTTAATTTAAGAATAATTTAATTAATCAATTTCCTA

TTTTGTATTTTAAAAATTACCACAATAATTATGTAATTTTTGGGATATTTGAAACTTTGAAAAAAGTGGTATTGTAT

TTGAGAATAAATTAATTAATGTAATTCTTGCTGCTCATCGTTCCATAACTTACAAATATTTCTCGGTATTTTATTTG

AGATAATTCTTATCATTTCTTCCATAGCTTTCAATATATTTATAACTTATTTGTAATCACTCTTATCAC

MARKER 50378 (SEQ ID NO: 83): A→G
TTGAGATATCAAATCAAGCGTTGCATATTTATAGTACACTGGTGTAGCTGAAATCGCGAAGAGAACACGAAAATCAG

AGAAGTCAATGGTTCCTTTGTGTTGGATTTCACATGAAAGCATCCTTATGTTGTACATGCGTGATTACAATATGATA

CAAGATGTAAGCTAAAAATTGTTTTATCTTTGTCTATGAGATGTAGTTCATACTCTATAATAAAGTCCCAACCCTTA

ATTCTCATATTCACAACCGTATCAGAATCCAACACCAAACCATTATAAAGAATGTTCTTCGTCGAGGCG

MARKER 51565 (SEQ ID NO: 84): C→T
CCACTATCGCTTACACTTTCTTTATCCTGTTCTTCTTCATCTTTCGTTTTGGACTTTATTTTACTGTCAGGTGACAA

GCAAAGTAACGATGTTGGACTTTGCGAAGATGTGGATGGTACGCTAGAAAAAAAATGAGGATTGGTTAATATGTCTA

ATTATTACATCGCTTTTTTTAAATCTTTTCTAAAATTAAACTGAATAATCAACTTATTTGCTATTCAGTTTATCTT

ATTTTTTATCAACAAAATTCGAGGAAACAAATCGCTTATCAGAATAATTGTTTTGATCAACAAATAAAG

MARKER 58162 A (SEQ ID NO: 85): G→A
CAATCCCACAAATTCAGTGTGTCGGCGGGTCAGCGAAGGGAAAGTTTGAACCGAGGGTATGTACAAATTGTGATAAT

TTTGTGATGACGTAGTAAATTTCATAGTTTTGCATGCTTTAATGTTGATAGTCGCACAATCCTACGTTGATTAAATT

TAGCTATTAGATATCCTACTAAATTATGTTGTTCATAATTTTTGTTTTTAAAATGCTCCACTTATATTTTCAGGTTG

TGCAGTGCTACAATAGGGGTTATGACGGCAATGATGTCCAATGGGAGTGTAAAGCGGAAATGAGCAATC

MARKER 58864 (SEQ ID NO: 86): T→C
TCAGATAAATTGTATTTGATGTTAATTCAAAGAAGAAAAAAATAATCAGTAGAATATGAATCGAATAATATTCATAC

AACCAGTTTATTCATTATTATTCACTTTTAACGTCTAAATGACGTAGCTACGCTTTTTTTCTCGCTTTCAAGCCTTT

ACTGACCAAGATTAATGTACATTCTGTTGAACAAGATTAATCGACATTCTATCGATCAAGATCAAGCTTTTACTGAT

CAAGATTAATAATGACATTCTTCTGTTGATCAAGATTAATCGACATTCCATTGATCAAGATTAATCGAC

MARKER 62666 A (SEQ ID NO: 87): G→A
CTCTCTAAAACCTATTGGTCACTAAACTTGCACTGACTAAAAACTATTGGTCATCAGACTTGTGATTCATTGAAAAG

ACCGTTAGCCGCTAAAATTATGATTCACTAAAAAAAATCTATTGATCATTAAATCTGTAATCATTGAGAAACTACAA

TCATTGGTCATTAAGTTTGTGCTCTCTAAAACCTATTGGTCATTAAACTGACTAAAAACTATTGGTCACTGAACCTA

GAGTCTATTAAAAAAAAAATCATTGTATCAATAAATTTATTGTTTACTATCAAATCCATTGATTACTGA

MARKER 62666 B (SEQ ID NO: 88): A→T
TCTAAAACCTATTGGTCACTAAACTTGCACTGACTAAAAACTATTGGTCATCAGACTTGTGATTCATTGAAAAGACC

GTTAGCCGCTAAAATTATGATTCACTAAAAAAAATCTATTGATCATTAAATCTGTAATCATTGAGAAACTGCATTCA

TTGGTCATTAAGTTTGTGCTCTCTAAAACCTATTGGTCATTAAACTGACTAAAAACTATTGGTCACTGAACCTAGAG

TCTATTAAAAAAAAAATCATTGTATCAATAAATTTATTGTTTACTATCAAATCCATTGATTACTGAATA

MARKER 7060 (SEQ ID NO: 89): G→A
AAAATGTATCAAATTCTTCGATGCCATAAATTATACAGACTTGATTGGCATTTTTCTAACTTTCATCATGAACCAT

TCTATTTCTAAATTGATCCATTACAAAATCAACTTTGTGATATCATCAATCTCAGTCATAACGAGAAATAATGATAA

TATAAAGCGACTATCATTTGAATTTCCTGAATATTCAAGATGTAATTACATCTTTTTTTTAATGTAATCAAAATTTC

TTGCCATCAATAATTTTTCAACATATGCTTTCATCGACTGCCTTATGCAGATCGTAATGATGACAGCCA

MARKER 12056 (SEQ ID NO: 90): T→C
ATTGATTAAAAGAATCAACATTAAATTTTTGATATAGTCGAGAAATCCTTCGTGATAATTCTTTTAGAACAATTCT

TTACACTAAACTTGTATTTACTTGCTTATTATTTGTCTAAAGATACTAACTATTTGTCAGTGGAATTTATGATCTTG

GCATTATTGCATATAACGCTTTCCTAAAATCTGAAATTTTTCAGTATTTTAAAAACTAAGACGATTATTAAATATTA

CTCAAAGCTTAGAACTTTGATTATACTAATCAAATCAAAAATTTCATCAGCGATTTTTGTTGTGTCATT

MARKER 16261 (SEQ ID NO: 91): T→C
ATTTTTTCCAGCAGAATTGTCATCAAAAATCCCATTTTTGATATCCTCTTCATCGAAACTTGCTCCTGAATCCAGAG

AACAACGAAGAATGTGTAAATCTATTTCAGTAGCCTGCTCATTGTGCAATTCAGCGACTTTATTTCTGTGCTTCAAG

CTAACTTCTTCATTATGCCACTCCTCTTCTCTCGCTATTTTTTCGCTATCTAATTCAAAATCTTCGTCTGAAACGGA

ATCAACTCCTGACGATGTACTCGACACTGATAATATTTTCATGCCGATTTTCTCTCAAACGAATCTTT

MARKER 23195 (SEQ ID NO: 92): C→T
GAATGAAGAGCAAAAAAATAGTCACGACCACCTGCAATAAAAACAGCATCTCCGTAAAAATGATTGAATTGATTCCC

GAAATACGAGTTTATCAAATTGAGAATTATGCAAATTAATTATCAGCATGCAGATTTACTGATTTTATATCTCTCAT

ACCGAAATTAAGGTGATGTTTTCCATTTCTTTGTTTCCACAATGTCTTCTTTGTGAATCGTTTTGGATCAACTATTA

ATCCGATCGAATCAATCCTCCAAATATGAGTTTATTCAACGTAACAAAACATTGTCCGAGATAATCAAA

MARKER 28579 (SEQ ID NO: 93): T→C
TGGAAATTTCGAAATCGAAAGGATGAAGAAAAAGGATCCTTGATCTATACATTAAATATCACCATATCAACTAGCAT

GGCAAGTCAAAGTAATGTTATCATTTAAATAAAAAAGATGAATAGTAGGACTACAGGTTATATTGTTAAAAGTCGAC

AAATTTGGAGTAATTGACAGAGATCAACGATTAAATGTAATGGATGATCTTATCTTCTTTTTTCAACTACGCCAAAA

TGAAAATAACAATTGAATTTGTCGAATAAGAAACTAACATTTTGAAAATAAGATTGAACATTTATAAAT

MARKER 48869 (SEQ ID NO: 94): G→A
GGTTGGATCATTATCGACAGAACTTTAGAAGTTTCTTGATAAGGACGAAAAGAAGCAGCACCATTGCTGATCTAAAC

AAGGAAAAAAGACCTTTTTTGGAATATTGAAGTTTTTACTGATAGGTGCGTGCTGTGTACTGTGGGCATAAGTACAA

GCTTCATGCTCCGCAGCGTGAATACGTGCTGCATGCATACTATGCAGTAAAGGTGCGTGTCGTATTGCTCAATAAGT

GTATAAATTGCTGCTTTTCTTGCATAGTTAAATATTTTGTTTTCATTTTTTCCGCTATTCAAAATAAAT

MARKER 53021 (SEQ ID NO: 95): G→A
GTTGGGATTTCAGACTCTCACTCGGTGTCGTTTCACAGTGATATCTGAATCGAAGTCACAAGCAGGTATGAATGCAT

AACAACTAATATCCATTGCAGAAACAAGGCAAAACTGAGAAGCTCGAGCAATATAGCTATAGAAGCTGGTACC<u>A</u>CAG

ATGACATTACATGGTATTTCCATTTCAGCTTCACAAACATTGTAAATAGCTTGCTTCGATGATTCAATATCTCGTTC

TACGATATTCTTAAAGTAATTTTTATTTATTTGAAGTATAGATTACATCCATGTTCTATCTATCATTTC

MARKER 7986 (SEQ ID NO: 96): G→A
TGTTCTGAACATCTCTTTTTGATTATCTTTTTAATTCCTCCATTATTTTCGTTTTTTTCGTTGTGAATTAATATTG

TTTGTCTTTGATTCAGATGATATTTTCGGATCGTAAATAGATGGCATCGGCATAAGCGTATTGAGAAGCATTC<u>A</u>ATG

GTGCACTCTTGCTTCTTTTTTTTTGAAATCTTTCTCGATAATCAAATAAGTGCAGGATGCCAATCATTAACAATTT

CGTTCCACTTTTTCAGTTCTTATTCTTATAACACCACATCTCATTTGCAATTTTGTCGCCAATGATTTT

MARKER 48094 (SEQ ID NO: 97): C→T
TTTTTTCGAGGTCACTCTGGAAAAATAAATCATATTTTAAAAAGACATAAAATAAAAAATATGTATATATAAGAAAA

TTTTTACTCTGAATTTCTTAAGAAAATTCTCGATTCTGTTTTCCATAAATTCCGGAATATGTTGTCCCTGAATT<u>A</u>AG

AATTCGATTCCTTGCACACCATTATTTCGTCTAGTTCCTGTGTGAACAATGTAACCTGGAAATGAACACATAAACTG

TAATATTTTGAGCTTAAAATAATTATGAGGATGCGAAACTGAAGATATTCATAAATGTTTAAAAAAAAA

MARKER 6568 (SEQ ID NO: 98): T→C
GTCCATGCATTGCTTTTCGGAAGTTAGTGTAGATTCAGTGAATATTTAATACCAGTCTCTTTCTAATTCAAAAGAGC

CTCCCATTTCTTTTTTCAGTTTCAGTCTCTGAATCAGAGCGTGTAATCTACCACTCCATTGCCGAAAACAGCT<u>C</u>GAT

GTATTTCCTGCTACGTAGTGTTTAGAATTGGCGTATGCCACTTGCTCATTATTCGCGCATGAAGTGTAACTGTGAAT

AGAATGATACTACTGTTAGAAGAGAATGCGTTCACTTTATTTAACATTATACTGATTCATTTCTTCTTT

MARKER 17022 (SEQ ID NO: 99): C→T
AGTGAACGAGAAAAAACAGAAGAAGAGATAGCACATCAAGATCGTGAGAAATTAATTAGACAAGAAAAAGCTCGTCT

TACACAAATATATCAGGTTTTCTTTTTCTTGCTTTCGAAAGTTATTTGAATTATCTCATTTCTTTGAATTTTAT<u>A</u>AG

AAATAATTTAATTTTTTTTGAAATTTTGCCTATTGAGCTCTAAATTTTGTAAAAAGTTTTCTAGGATGATGTTAGC

AAAGCAAAAAAGAAATCCAAAAGTGATGGTAACAAACAGGAAGATTTTATAGTGAGGTACGATAATACG

MARKER 55751 A (SEQ ID NO: 100): A→G
TAGACAATATCATCCTTCCTTTTTTTTTGCTCAATTTCTCTGCTCATTGCTTTGATGATAATGGTAGGTGGTATAAT

GAAACGAATAGATAATTGATGTTCGCAAACATTTGCTGTTAAATTTCAGTAAAGAAATTGACCTTTTTGCTTT<u>G</u>TGT

TGGATGTTTAGCTTCATTTTCTTCTTGTTCATTGTCATATTCATTCTCTCAAAACTTCTTGCTTAGCGATGCTAATA

TAAATACTGGAAGAATGCCTTTGCTTTGTTTTAGTTGTAAATCATCACCAAGGTATTTTTTTGCAAAAT

MARKER 55751 B (SEQ ID NO: 101): A→G
AAGATGAAACTAAAAAAAATTATTTCGAAAAAAAGAAAATAAAATTAATGAAATAAAAGCAAAAATGAACAAACCGT

ATTAATTTTAAACAATAAACAATATCGAAATCGAAAAATGGACTATTATTGATGAACTATATTTTCAAAATGT<u>G</u>AAA

GGTCAAAGTTTGTTTCAATTATGATAAATACAATTTAAAATAAGATTAAGCTAACAAATAAGTTGAGCAAATTGATG

AAACAAACAAATCAGAATATATTACAGAAAATGATATAACATGAAAATATATTAGACCAATTATTTTTA

MARKER 15893 (SEQ ID NO: 102): T→C
TTGAAGTTTTCAGATAAACTTTGATAAAAAATTGTTCTATGAATTCTCAAATTTCAATTAGTGATACTTATTTCGAA

GGTAATTATGCCTGATTGAATCTTCAATATCAACAAAATGAAAATTTTAGTATGATTGTTAACTCATACACCT<u>C</u>TAA

TTAAAGGTATTTTCTTTATCCCATGAAATGAAAATTTATTAAGAACTTAGAAAGCTACGGTATGCCTTTGATGCAAA

AGAAAGATTCATTTTCATTAAATCATGTTTAAAAAAAAGAGCAAAGAGCAAAAGGTGATGAAAGTTTTT

MARKER 25462 (SEQ ID NO: 103): C→T
TTCTATACGAAATATTTGTCTGCCATAAATCTACTCAGGAACTCGATACATCAAAACATAAGTACGCTTGCTCTTTA

TTTTTCGTTTGAAAAATAAATAGATCATTTTCGCACTTACATTTCAATTTCAATTGCTTTATTCATATCTTTC<u>T</u>GTT

TTTACTTACTGGTATTTAACAGTCGTTGTTCACAATTTAATGATCTATGAAACACCATTTAATTGTATTTGGACTAA

CTTTTCGACAAGCAAAAGATTAAAATTGTCTTCAGATACAGTTATAAATTTACATTGAAGATAAATGAA

MARKER 33494 (SEQ ID NO: 104): A→C
TAACGATCTGTATATCAATGGAATAATATTCAGTTCATGTTGTACTCGATATGAGATAGAATTACAATTTTGGAACA

AGATAATCTCAACAGCTATTTTCAAGAATAGTTAAATTAGGATACCATTCAAAGAAACTTTAAAAAATGATTT<u>C</u>CAT

ACATTAATGCTTTTTGTGTTTTCGCTCTCGACCAGAATCCAGGAATTGTCCATTATCATCAATTTGATTAACTTTTA

TCTTTATTCTAATTCTTCAACATTTCTCTAATTGATATTAGTTTCAATATTTTAATAAGTAAAAATTTA

MARKER 17935 (SEQ ID NO: 105): T→C
ATAATGTGTTATTGATCAAAGGATTTTTAGTTACCTACCAGATGGAAAAAAAGCAAGTTTACGAAAACAGAAGTTAG

CATCAACTTTCATCCATGGTTACACCGTATATAATCCAATCGACTCATACTTTATGTTGATCTGATTTTATAG<u>C</u>AGA

TAACTAGTTACCTTGCTCAGCAGCAGCTAAATCCTTTCTATTTGCTTAATAACAGAAATATTTTTCATTAACAAAGA

AATTATACTCCGTGTTTGACATTTCATTTTAATTTCGTTCCAAAAATGAAAAAAGCTTCGTCCGGAAAT

MARKER 48561 (SEQ ID NO: 106): C→T
ATTATTTTGTAGTTTTTCATTTTTTAGTTCAATTTTCCTTTGCTTATTTTAAATATGCCATTCTTTATTCAGACTCA

TAGCGAATGCATATGTTCATTAATTTTTTTAGTTACAGTTACAAATTCTCAATTTCTCTTTAATCATTTTTTT<u>T</u>TCC

AAAAATAGTCTGAGCACTCAACCATTCATTCAACAATTGCAGCTTTTTTTATTGGAGCCTTGTCAAATTATCAATTC

GTTTCCATGTTTATTATTGAAATAATAAACGGTATTTAGGATAACGAAGTTCGCTTAGCTTCTTTGACT

MARKER 42003 (SEQ ID NO: 107): T→G
AAAAATTCAGGTAATGAGATCAGTAATTTTTTTTGGTCACTTTGCTGTTTCTTATCAGCTCATTGTTATCCATATCA

AATGAGCGAAAGTGTGTATCACATATTGGCAGAGTGTAATCTATGAAGATTTTGCGTATCAAAGTAATTATGA<u>G</u>AGA

ACTGATAATTTTATTTTAAAGTAGTAGAAAACTCGAATTAAGCTAATAAATAATCGGTTGATATCCATGAAATGAAT

TACTAATGAAATGGATAATTGAGTAATAACAAATGATATTCATGAAGAAAGGCAGGTTTTTTTTAATAG

MARKER 29566 (SEQ ID NO: 108): C→T
TATACTTAAAACAAGAAATACAATTAATGCCAATAGCAGAGTGAAACTTCTGAAAAATAATGAGTTGAAACTGGTAA

AATTAACATTTTATTAGAAATTTCAGAAACTTATGACTCCTCATGGCACTATCACAAAATGTTTGAAAAAAATT<u>T</u>GAC

AGCTCGCGTCGATTGCAAAAATCATGATTCCTGATATTTAGTATCGAACATGTGACAAATAATATAAAGACCTAACC

ATAAAGCACTGAAACAACTCGCGGAAACAAAAAATTAATTTGCATAAACACGGAATACGATCAGAAAAT

MARKER 33868 (SEQ ID NO: 109): G→A
GAATTTTTTAGAAGGCTTGAAGTCGAGAATATTAGAGACTATATCGAAGACTTAAATAATCCTGGTAATCTTCTGT

ATGAATCAAAATTACCTCGAACAGAACCATTCAGCACATCACGAGATAATTCATGGAATGAAACTAGCCAATC<u>A</u>GAG

CGTTGTAAAAGAAGAAAGTTATGAAATGACCTTAAAATCAATTTAAAGCATGTCCTCGCCATATAAGCGTTGAAAAG

TTAGGATAGAATCAATTATCAAAAAAATATGTTAACTAGATCTTATCAATCAAAACATCAGAAGGAAAA

In another example, genetic markers from *D. immitis* include the sequences below (SEQ ID NOs: 110-127), where the underlined nucleotides (i.e., the polymorphic sites) indicate the SNP nucleotide position within the fragment that correlates with resistance to MLs (i.e., the alternative nucleotide). Those markers were identified after genotype frequencies comparison between susceptible individuals and confirmed ML resistant individuals. In these sequences, the underlined nucleotide at the SNP position is generally different than the nucleotide found at this position in organisms that are susceptible to MLs (wild-type). In the sequences below, the nucleotide at the SNP position in the indicated sequence correlates with resistance to MLs. In the heading for each sequence, the nucleotide change from wild-type to the alternative nucleotide (alternative nucleotide correlates with ML resistance) at the polymorphic site is shown.

MARKER 31307 (SEQ ID NO: 110): A→G
ATATGATAATAGTGAAACAATTCCATCACAATAAATATTATCGATTAGG

AGATAAATTAACATTGATGCCTCAATTTTGGTCAACAATATATATTTGC

TATTAGCATTTTTATTAAATCGTTTTTATCTGACTTGACATAAATTGAA

ATA<u>G</u>AAAAAATTGAATCTGTTCCTTGTTAGATTTTCTTCTAAAAATTCT

TGAAATACAAATAATTTCTTAAATTTCAATATTTCTACATAATGTATTG

CGACAAAAATGCTAATGATTGGCTTATTATTATTTCGAATAATTTTTA

ATCAAA

MARKER 26225 (SEQ ID NO: 111): A→G
AGCTCGAAGATCGGACAAAATTTGTTCAGCTTGTTGCCTTGAGGCTTTA

GTCTGAAAAGACACTTAAAAGTATAAACAAATTATATTCAAAAAATCTT

ATTTTGCATTTGCGTCTTAATTTTTGCTTTTTGCAAAGTTTTTTCCGAG

CAAGTTTTTCTATCTTCGAAAAGATTATATCAATTAAAATTTCAATTTA

AGCAATCATTGCCTCTTCGAGTTTCTGTTTCAGCAAATAAATATCACCA

CCACGACGCTGTCGGAAGAAAGAAACGCCTTTCCCAATTTCTCGTCTCA

ACTTTT

MARKER 47722 B (SEQ ID NO: 112): A→G
TAAGAAAGCTGGGAGATTTTCCAAAAACACTATTTCCCACGATTTGTTG

TTTTCTATGATCAATTCTTAATCAAACTCTGAAATTCTCAAATTTTCGA

TTTCTATCCAACTTCTACATATTTTTTTAGAAAATTCATATTTAGCAAA

GCTGAGTGTAGAAATAATTCATACTTGCAATTCATTTTTCTTAAATTTT

CGAATTTCTTAAAAAAGTATTTCAAATTACCTACCAATTTTGATTGGAA

AATTCGTGGATGCTAAAAATTCAAATCAAAATAGTTAAACAGTATTCCT

AATTGT

MARKER 58162 B (SEQ ID NO: 113): T→C
AATTTAAAAAACACATCGACATTTTGCGGTACGGTAATGATTGTTTACA

GTAACTAAATGTGTCCTACGGTAGTAATACTCGTGTACGTAATGAATGA

GTATAGTGACCGGATATTTCCTTCACTAGTAGGCAATATTAAGAAGTAT

TTTCATTTTCATATTCTATCTAAAATAAACCGATAAAATGGTTTTTGAA

TTATTACTTTTTGATTGTTATTTTTTGATCCTAAATTGTAAAATACTGT

AATAATTTAGCTAATTTCTATGATTCTATTCAATATGCTTAAATTAAAA

TTCTAA

MARKER 17709 (SEQ ID NO: 114): T→C
TCGTATTTGTTGTATGTAATATAGAAATATTGTTTAAATTCAATATGTA

GAAAAAATTTCTANNNNNNNNNNNAATTAATTACATATTAACTCGTATTT

GTTGTATGTAATATAGAAATATTGTTTAAATTCAATATGTAGAAAAAAT

TTCCATAATAAAGACGAACAGCATTTATAATTATCAATGATAAGTTGAA

ATTAATTCATCAATGATAAGTTGAAATTAATTTATTTGAAATAATTTCT

TTGAAATTCGAATATAGACGAGAATTTTTTTTTTTTGCTAATCGTTTA

TCAAAT

MARKER 47141 (SEQ ID NO: 115): T→C
TCTAGCAATATAAATTACAAGAATATGCCGTCCAAGTATTTCAGAATTT

ATTATTAATTTGGATAATAATACATTGTAAATACTGCGTATTCTGGATT

ATTATGCACTGCATAATAACATGCAATTTCGTCTACATATCGCGAATAA

ACGCCAAAGATTTCTCGATAAAGAAAATATAAGAATTCGTAAATGAA

TGTTGTGTCAGAGATATGTGTTAATTCATAAGTCAAGATGTTGTAAATC

GATCCATATTAGTAATCATATTTACGTGCTCGTAAATAAAAGCGGTGAT

TCTTGT

MARKER 48750 A (SEQ ID NO: 116): A→G
ATCGAAAAAGATGATCTGATGACGGAAGGCGAAATGTCTGCAGAAGCT

AAGATGACGGAAGAAAAAGTGAAGAAATGAAAGAAGAAGCTGGTAAAA

CTCAGAAGGAATGTAAAACTGGAGAATCGAAAAAAGATGATCTGATGAC

GGAGGGCGAAATGTCTAAAGAAGCTAAGATGTCGGAAGAAAAAAGTGAA

GAAATGAAAGAAGAAGCTGATAAAACTCAGAAGGAATGTAAAACGGAAG

AATCGAAAAAAGACGATCTGACGACAGAAGGCGAAAAATCTGAAGTAGA

TGAGCC

MARKER 63962 (SEQ ID NO: 117): A→G
ACTAATGATAAGAAACGGAGCCGACGATTTTAGGAAATGAATAATAACG

ACATTGACAACCATTGTTAGAAAATTGATAGTACTGATAATAAAAGCTA

GTTATAGAAAATTGATAATAATAATAAAATTGCTGGTAGCAAATGTCTA

GAAGTGATAATAAAATTAATGATAGCAAATGGATTAGCAATGATAATTA

AACTGATGATAGCGAATGGATTAGTAATGATAATAAAATTGATGATAGC

AAATGACTAATAATGGTAATAAAAGTTAATGCTAGTGATAACTTGTATT

TTAAGT

MARKER 6372 (SEQ ID NO: 118): A→G
ACAGTTTATAGTTACAATATTCTCCGGTGACTAACTGTATTTTACAACT

TATAATTATAGATTACAAAATATATTATAGTAGTTTATAATTACAGTA

TTCTTAAGTGAATAACTATACTTTACAGCTTACAGTTACAGTAGTTTTC

TATGTTTTTGAATATTAATTTTACATGGTTTTTCCTAGTTTCAGTTTCA

AAATTTTCAGATATTTTATGTGTTAAAGCAAATTATATTCGAGATATAA

AAAGTACTGGTCATATCTTACAATTCTCATCCTTCTATATTGGAAAGAA

TTGAGT

MARKER 15611 (SEQ ID NO: 119): T→C
GTATTGGGACCGCGTATCGGGAAATCTGAAAGAAGTCTTTAACAGTATT

TTAAATGAATAATTCAAATCGTTACTTCTTAATATATTAATTTATGCGT

ATATATGCAGTACATAGCATTGCTTAAATTCTTATTTTTCCGCGGTTAA

AACCCTATGTAAGATAAGGGAGGTGATTGTATCTGCGCCGTACTCCTTG

TTTTTAATCTACCTGCTTGTTGTATATCCTCCACATATTGTAACTGCAGC

TTCACATTTGCATATATAGTAAGGGCATCGTTGTCTCCAGAAGAGATAT

ATTATC

MARKER 46432 (SEQ ID NO: 120): T→A
GCTGCCCGAATGTTACAATTAGGACGAAAGTAAAAGTAGTTGACTGTAG

GTATGACGATAAAGGAAAAATTTGTATCTTAAGACTTTACAATTTCTAA

ATATTACGTGTTTTATCGTGCTAACATCACGAATTCCATATTCACAAAA

AAAATTTTGTAGAACTCCATCTGGTTTGGATGAATTTGCTACAGTTGAA

CTGGATGATGGAACGAAATTGCAAACATCTCTTATTGTTAGTATTTTCT

AAATTCTGTGAAATTTTGCAACGGCATTCATGTTTAATTATTAATTTGG

AGAAAG

MARKER 29594 (SEQ ID NO: 121): T→A
AAATAAGCAAATCCGAAAGTATTACATATACGGACTAAATATTGCCATT

CATTCGGGAGTATACCATTGCAACCATTGGTATTTCATTTGATCGAGAA

AACTAGTTTTTGTAGTTTGGGATAAAGAGAAATGGAGAGAGGAACTTTC

ATGATCAATTTCTTTACGTACTGAAATTCATTTCTATGGATGTTCTTTT

TCTATTTCATTCTCCTCAGCAAATACAGTCCGAACAGTCATCAAATAAG

TCTAAAAGGCATGAATAATATAAACATCAGCAACTTTTTAAATGAATGC

TTATTA

-continued

MARKER 26784 (SEQ ID NO: 122): G→C
ATTTCTATAAACATCTCTTGCATTGATTAATTTAACATGTTGCAATAAA

TATTTCTTACTTTTGAATGTATCATTTACTAGAAAAAACTTCAATCGAG

GAAATAAGTTTTAAAATAAATTCATATTTGAATTCATGTCAGTTCAAAA

ATTCTATTACTATAATACATGTCTCTTGGTTGTATCTTTTTTTCTTTTG

AAATAATACAATCAAACGGTTTCCTAAATTTTCATAGACATCATATTTT

AAAAAAAAATGCATTTGAAAATTTTCGAAAATCAATGAACTTAATTGAT

GAAAAA

MARKER 51661 (SEQ ID NO: 123): C→G
GCATGTGTATGTAGTATTTCTTTGTAAACAACATATCTAATCTGTCTGT

CCCTTTAACATTATAGAATAGTCAGTTAGTCCGCTATTTATTTTAATAA

CAAAATATCTCACTTAACTTCCATTTCTTTCCTAAATAATTTTGTTTCG

CTAGATCTTTCCTATAATTTTCAAATTTTCAAAAATGAATTAATCTTTT

ATTTATATATGTGTATGTATGTGTATGTATGTATGTGTACGTTGCATAT

ATGTATATGTATGTGTGTATGTGTGTATATGTATATGTATATGTGTGTA

TGTGTG

MARKER 7819 (SEQ ID NO: 124): G→C
TATGCATAATGTGCGACCAGCCAATAATGTCTTCAAACCATAATTATGC

AGAAATAAATTTTTTCCAGAAATAATTTTTTTTTTTTACATATACTTC

CGATCTGTGAGAAAATACATTTGAAGTGAAGTGTGAAGCAATGCTACTT

TTTCAAACAACATTGTGAAAATGGATTAAAACGCACCAATGGAGCAAGA

GATCGTAAGTTTCGTTCCGCATGTCCTGTGGCAACGTGTAAACCATCCG

TTAACGATATATGATGTAAAAGCCGACACACCCAAATTAAAATCCATTA

TAAACA

MARKER 26704 (SEQ ID NO: 125): G→C
AAATGGATCGTATTCACTTCGTAAGAACTTAGTGAACGAAAAATCAAAC

CATCACAATAACTTTACTTTTTTTCTTTTTTTACTAAACACACTATCCT

ATGAAAACAAAATGTCCAAATAGATTCATATGATAATGAACTGTGAAGT

TATCCAATCTATCAGTTCTCGAAGAGGGAATAAATAAAAACATTAAGCA

ACCCACCGATCTTCGCTGACCATCTCCTTCTTCATTAGCAAGAAGCAAA

TCTTGTGGTGATATTTCTGCAACCATCTGCAAAATAAAGCACGAAAAAT

TAAGGA

MARKER 14329 (SEQ ID NO: 126): C→A
TTTGATATGCAATCAACTAACCAAATCAGAATTCAATGCATTCTGATAA

ATTTCTTCAATATCGTGCATCAATTCGACATCATATTTTGACAGTGATG

CTACCTTTTTAGCCGTATTTCGGAAAAATATGAATTCAACCAGCTGCGT

CCCAAAATTTAAGGCTGTAGCAAGTCCAGCAACAACCAGCCCTACAACT

GAAAATTCTAAAAACTGGTTCACGTGCTTATCATTAATAATTTCAACAC

TATCACTATCTCCACATGAACTTGATCGATTATAATTTAGTAGAACTGA

AAAAAA

MARKER 56169 (SEQ ID NO: 127): T→G
ACAAATTCGTTTTAATATTGGATTACATTGAAATTGCTGAAATAAAGTG

GAAATATTGAAAAGCATTTTACAATATTTGTTAACAACATTATATTTAA

AGAATATACACCTTGGTTTAAATGGTAAAATAATCTCAAGAATTTTCAT

TAGGTTAATTTTTTTTATTTATTTATATTCACAAAAAATTGTAAAAGA

AAACAAAAACAACAATAATAACGGTGACAACAACAACAATAATAATAAC

AAAACTATTTGTTGTGATTTTGCAGCATTGATGTAGTGGGGATCTTTTG

GAGCGA

The genotype frequencies for each SNP (SEQ ID NOs: 110-127) at the polymorphic sites are shown in FIG. 29 (Table 1). In one analysis, genotype differences of susceptible individuals were compared with confirmed resistant individuals. In a second analysis, genotype differences of susceptible individuals were compared with grouped confirmed resistant and LOE individuals.

Kits and Methods

In embodiments of the invention, probes of the invention may be provided to a user as a kit. A kit of the invention may contain one or more probes of the invention. For example, a kit may comprise a probe capable of determining the genotype of a nematode at a SNP position in one of the fragments disclosed herein. The kit may further comprise one or more reagents, buffers, packaging materials, instructions for using the kit and containers for holding the components of the kit.

A probe of the invention may be one or more molecules that are capable of binding to, or associating with, the nucleic acid sample to determine the genotype of the nematode at one or more specific positions (e.g., polymorphic site) in the fragments disclosed herein. For example, probes may be used to determine whether a wild-type or alternative nucleotide is present at the SNP position of one or more of the fragments disclosed herein. An example probe may be a nucleic acid molecule or oligonucleotide. Example probes may contain a label or labels. Example labels may include radioactive labels, enzymatic labels and/or fluorescent labels.

An oligonucleotide used as a probe or primer may comprise any size, shape and composition that is suitable for use in the context of the invention. Preferably, an oligonucleotide of the invention may comprise DNA, RNA, synthetic nucleotides, non-natural nucleotides, altered nucleotides, or combinations of one or more thereof. In one embodiment, an oligonucleotide of the invention may comprise locked nucleic acids and/or peptide nucleic acids.

In embodiments of the invention, an oligonucleotide may comprise a sequence of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, or more nucleotides.

In embodiments of the invention, an oligonucleotide may encompass, without limitation, a primer or more than one primer, e.g. a primer pair, such as a forward primer and a reverse primer.

A primer may be an oligonucleotide that may be used to initiate DNA replication. Typically, a primer is a short oligonucleotide that may be about 10, about 15, about 20, about 25, about 30, about 35, about 40, about 45, about 50, about 55, about 60, about 65, about 70, about 75, about 80, about 85, about 90, about 95, about 100 or more nucleotides.

A primer may be used as part of an approach to detect the genotype of a nematode at a specific location of a gene. For example, a primer may be useful in amplifying DNA such as by PCR, RT-PCR and qRT PCR, for subsequent analysis, such as by Southern blot, sequencing, HRM (high resolution melt) or SSCP (single strand conformational polymorphism).

As used herein, an "aptamer" may be a nucleic acid or a peptide molecule that binds to a specific molecular target. For example, in solution, a chain of nucleotides may form intramolecular interactions that fold the aptamer into a complex three-dimensional shape. The shape of that aptamer allows it to bind tightly against the surface of its target molecule. Because of the diversity of molecular shapes that exists for nucleotide and amino acid sequences, aptamers may be obtained for a wide array of molecular targets, including, but not limited to, nucleic acid molecules, enzymes, membrane proteins, viral proteins, cytokines, growth factors, and immunoglobulins.

A probe of the invention may be prepared according to standard techniques known to a skilled person. For example, a probe may be produced synthetically, recombinantly or may be isolated from a natural source. In one embodiment, the source may be a biological source, for example, from a microorganism (e.g. a bacteria or a virus), an animal (e.g. a mouse, a rat, a rabbit, a goat, or a human), or a plant.

In the context of the invention, "a probe" may mean one probe or more than one probe. One or more types of probes may be simultaneously used in methods of the invention. Probe design and production are known in the art. Generally, a probe may be produced recombinantly, synthetically, or isolated from a natural source, e.g. from a cell, an animal or a plant. However, a skilled person would appreciate that probe production may depend on the type of probe at issue. A preferred probe may be a nucleic acid molecule (e.g. a primer), with or without a fluoroflor or dye. A probe may be linear or in the form of a hairpin, with a fluoroflor, with or without a quencher or another fluoroflor (e.g. for FRET analysis). It could also be an antibody that specifically recognizes the DNA (or protein) sequence. Another probe could be based on a RNA molecule. What would be preferred may depend on technical considerations, stability, cost, ease of use, etc.

In embodiments of the invention, probes of the invention may be provided to a user as a kit. A kit of the invention may contain one or more probes of the invention.

Uses of the Methods and the Kits

Methods of the invention and kits to carry out the methods may have research, medical and industrial applications. The invention finds broad application in the management of heartworms in infected animals and in detecting ML resistant *D. immitis* nematodes in an area. Representative, non-limiting applications of the invention may include the detection, quantification and/or diagnosis of the existence of individuals or populations of *D. immitis* that are not susceptible to normal doses of ML for prophylaxis or therapy. In one embodiment, the ability to detect and quantify nucleic acid molecules of the invention is valuable insofar as it will instruct a practicing veterinarian to alter chemotherapeutic regimens for animals infected with *D. immitis* nematodes that have decreased responsiveness to MLs. Identification of ML resistant *D. immitis* nematodes may instruct a veterinarian to switch from ML therapy alone to therapy that may include an alternative agent or alternative agents, such as an adulticide (e.g. arsenic based drugs), diethylcarbamazine, antibiotics such as tetracycline, and combinations of one or more thereof in order to achieve cure and/or to minimize the spread of the resistant strain. Alternatively, a veterinarian may adjust the dosage of a ML and/or treatment regimen using a ML in the treatment of an animal infected with a ML resistant nematode. Typical recommended dose rates for ML preventatives include, for example, 6 μg/kg for ivermectin; 500 mg/kg for milbemycin oxime; 3 μg/kg (monthly) moxidectin; and 6 mg/kg for selamectin. A veterinarian may also combine one or more of the treatment approaches and therapies noted above in any combination suitable to treat an animal infected with a *Dirofilaria* spp. nematode, e.g. a ML resistant *D. immitis* nematode. For example, a veterinarian may treat such an animal with an adulticide, such as an arsenic based drug, and then follow up with a microfilaricide, such as a ML or diethylcarbamazine.

In one instance, an arsenic based drug may be used to treat an animal infected with a ML resistant *D. immitis* nematode. An arsenic based drug may include, but is not limited to, melarsomine dihydrochloride. Melarsomine dihydrochloride may be used, for example, at a dose of 2.5 mg/kg, twice, 24 hours apart. This may be repeated in 4 months depending on the response to the first treatment and the condition, age, and use of the animal. However, a skilled person would understand that the dosage may vary depending on the severity of the infection. For example, an infected animal such as a dog with severe (class 3) disease may receive one dose and allowed to recover for a few months before receiving the complete set of 2 doses.

In another instance, diethylcarbamazine may be used to treat an animal infected with a ML resistant *D. immitis* nematode. Diethylcarbamazine may be used, for example, at a dose of 25 to 50 mg per pound of an animal. The duration of administration may depend on the condition being treated, response to the medication and the development of any adverse effects.

In another instance, an antibiotic may be used to treat an animal infected with a ML resistant *D. immitis* nematode. Said antibiotic may include, but is not limited to, tetracycline. A tetracycline, such as doxycycline, which targets the *Wolbachia* endosymbionts in *D. immitis* may be used, for example, at a dose of 10 mg/kg/day for 40 days.

In a further instance, another anthelminthic agent may be used. Such other anthelminthic agent may include, but is not limited to, acaciasides. An acaciaside may be used, for example, at a dose of 10 mg/kg/day for 7 days.

In another embodiment, the detection of *D. immitis* nematode populations with the above mentioned genotypes may instruct the use of alternative agents, such as diethylcarbamazine as a prophylactic to protect susceptible animals, e.g. dogs.

In one instance, diethylcarbamazine may be used to prevent an animal from becoming infected with a ML resistant *D. immitis* nematode. In this regard, diethylcarbamazine may be used, for example, at a dose of 3 mg per pound of an animal once daily.

In another embodiment, a kit of the invention may be useful in as a commercial product in the detection of ML resistant *D. immitis* nematodes. Such a product may be suitable for use by, without limitation, a veterinarian, a physician, a pet owner, a farmer, a zoo keeper, an epidemiologist, or another consumer in need thereof.

EXAMPLES

The examples are tor the purpose of illustrating an example and are not to be construed as illustrating limitations.

Example 1

Susceptible and LOE Populations of *D. immitis* Parasites Used in the Studies

The various susceptible and LOE populations of *D. immitis* used in these studies are described below.

a. Susceptible isolates from Missouri, USA. Thirty five (35) *D. immitis* adult specimens were obtained from two dogs originating from an animal pound in Missouri. The history of the dogs prior to the animal pound is not known. The dogs were not subsequently treated. The *D. immitis* isolates were believed to be susceptible to ML heartworm preventatives.
  b. Susceptible isolates from Grand Canary, Spain. Seventy-one (71) *D. immitis* adult specimens were obtained from 12 dogs originating from a shelter on Grand Canary. The dogs were never exposed to ML heartworm preventatives and heartworm prevention is not practiced in this region of Grand Canary.
  c. Susceptible isolates from Grenada, Wis. Ten (10) *D. immitis* adult specimens were obtained from 2 dogs originating from Grenada. The dogs were recruited from poor, remote areas of the island where ML heartworm prevention is not practiced.
  d. Susceptible isolates from Italy. Six (6) *D. immitis* adult specimens were obtained from the Po Basin in northern Italy. *D. immitis* seroprevalence in dogs from this area is reported to be approximately 60-70%. ML heartworm preventatives are commonly given to dogs in this area. But, there are no reports of LOE (loss of efficacy) in Italy.
  e. Loss of efficacy (LOE) isolate case 1. Microfilariae (mf) were isolated from a dog that was previously described (see Bourguinat et al.; WO2011/120165). The dog was a male neutered Labrador mix, born in February, 2006, that weighed approximately 31 kg. He was a rescue dog from New Orleans, La., U.S.A., collected by the Boudreaux Rescue Crew, New Orleans, and subsequently transferred to Canada where he was adopted in January, 2008.

The dog was brought to the Main West Animal Hospital (MWAH) in Welland, Ontario on Jun. 6, 2008 (day 1) for a check-up. Blood collected from the dog tested positive with a heartworm antigen test (PETCHEK® PF; IDEXX Laboratories, Westbrook, Me.) and contained microfilariae of *D. immitis*. On Jun. 11, 2008 (day 6), initial work-up (bloodwork, thoracic radiographs, physical exam, urinalysis) was performed. Auscultation revealed a mild increase in bronchovesicular sounds in the lungs and a grade III-IV/VI heart murmur. The remainder of the physical exam was unremarkable. Thoracic radiography revealed moderate right-sided heart enlargement and an interstitial lung pattern in the caudodorsal lung field. These examinations indicated a diagnosis of class 2 heartworm disease.

Adulticide treatment was initiated on Jun. 11, 2008 (day 6) with 2.5 mg/kg intramuscular melarsomine dihydrochloride (IMMITICIDE®; Merial Inc.). The treatment was followed by two intramuscular treatments with 2.5 mg/kg melarsomine dihydrochloride on Jul. 9 and Jul. 10 (days 34, 35). Over the following 90 days, in order to eliminate circulating mf, the dog was treated on one occasion with milbemycin oxime (MO) and on two occasions with IVM (see Table 2). On days 159 and 160, four months after the last dose of adulticide, the dog was again treated with 2.5 mg/kg melarsomine dihydrochloride intramuscularly. The subsequent diagnostic testing and microfilaricidal treatments are summarized in Table 2. During the treatment of the dog, several heartworm antigen tests were conducted, including DIROCHEK® (Synbiotics Corporation, San Diego, Calif.) and PETCHEK® (IDEXX Laboratories, Westbrook, Me.), which are microwell ELISA tests, and SNAP® PF (IDEXX Laboratories, Westbrook, Me., a membrane format test designed for rapid in-clinic use (see Table 2).

To perform the Knott's test, 9 ml of 2% formalin and 1 ml blood (collected in EDTA) were mixed in a centrifuge tube. Centrifugation was performed in a LW Scientific EZ Swing SK centrifuge at 3000 rpm (604 m/s2) for 5 min. The supernatant fluid was discarded. A drop of 0.1% methylene blue solution was added to the pellet at the bottom of the centrifuge tube, mixed, and a drop of stained mixture examined under the microscope for *D. immitis* microfilariae. Table 2 indicates when this test was carried out and, when determined, the level of microfilaremia.

The dog was treated as follows. Two days after the last of three doses of melarsomine dihydrochloride in July 2008 (i.e., on day 37), the dog showed transitory signs consistent with death of adult heartworms (elevated rectal temperature, lethargy, cough, increased lung sounds). Beginning on day 41, these signs were managed with prednisone (Apo-Prednisone; Apotex, Toronto, ON, Canada), 1.3 mg/kg bid for 6 days. Following the administration of milbemycin oxime (MO) per os at 0.74 mg/kg on day 74, IVM per os at 50 ug/kg on day 95, and IVM per os at 200 ug/kg (4× the normal microfilaricidal dose rate) on day 125, the dog remained continually microfilaremic. On day 207, six weeks after the second treatment regimen of melarsomine dihydrochloride, on days 159 and 160, a Knott's test was still positive, so the dog was again treated with 200 μ/kg IVM per os. One month later, on day 242, a *D. immitis* antigen test was negative, which confirmed that the dog was free of adult worms. However, the dog was still microfilaremic. Thus, beginning on day 243, the dog was given MO per os at 0.74 mg/kg every 2 weeks on four occasions (see Table 2). Despite this, the dog remained microfilaremic on day 298. It was therefore administered MO per os at 1.1 mg/kg on days 298, 312, 326, 340 and 354. On day 356, blood was collected from the dog and examined: microfilariae were still present, and a *D. immitis* antigen test was still negative. On day 375, a blood sample was sent to Animal Health Laboratory, University of Guelph (AHLUG): microfilaremia was 6530 mf/ml, and an antigen test was still negative (see Table 2). As a result, beginning on day 384, the dog was administered MO per os at 2.0 mg/kg once daily for 7 days. On day 420, the dog had a microfilaraemia of 355 mf/ml. On day 420, the dog was again treated with MO per os at 2.0 mg/kg, and this was continued once daily for 8 days. Despite this second high-dose regimen, on day 480, while still testing negative with a heartworm antigen test, the dog had a microfilaremia of 1810 mf/ml.

Blood was collected from the dog on day 706 and DNA was isolated from pooled microfilariae.

TABLE 2

Diagnostic testing and treatment history for dog between 2008 and 2009

| Date (day) | Antigen test Name-result (+ve or −ve) | Adulticide (melarsomine)* dosage | Microfilariae concentration in blood (mf/ml) | Microfilaricide drug dosage (PO) | Comments |
|---|---|---|---|---|---|
| 2008 | | | | | |
| June 6 (1) | PETCHEK+ve[a] | | Knott's test +ve[a] | | |
| June 11 (6) | | 2.5 mg/kg | | | Classified as Class 2 heartworm disease |

TABLE 2-continued

Diagnostic testing and treatment history for dog between 2008 and 2009

| Date (day) | Antigen test Name-result (+ve or −ve) | Adulticide (melarsomine)* dosage | Microfilariae concentration in blood (mf/ml) | Microfilaricide drug dosage (PO) | Comments |
|---|---|---|---|---|---|
| July 9 (34) | | 2.5 mg/kg | | | |
| July 10 (35) | | 2.5 mg/kg | | | |
| August 18 (74) | | | | MO, 0.74 mg/kg | |
| September 3 (90) | | | Knott's test +ve[a] | | |
| September 8 (95) | | | | IVM, 50 µg/kg | |
| October 6 (123) | | | Knott's test +ve[a] | | |
| October 8 (125) | | | | IVM, 200 µg/kg | |
| November 10 (158) | | | Knott's test +ve[a] | | |
| November 11 (159) | | 2.5 mg/kg | | | |
| November 12 (160) | | 2.5 mg/kg | | | |
| December 12 (190) | | | | MO, 0.74 mg/kg | |
| December 29 (207) | | | Knott's test +ve[a] | | |
| December 30 (208) | | | | IVM, 200 µg/kg | |
| 2009 | | | | | |
| February 2 (242) | SNAP −ve[a] | | Knott's test +ve[a] ≥100[b] | | Interpretation: no adult heartworms |
| February 3 (243) | | | | MO, 0.74 mg/kg | |
| February 17 (257) | | | | MO, 0.74 mg/kg | |
| March 3 (271) | | | Knott's test +ve[a] ≥100[b] | MO, 0.74 mg/kg | |
| March 17 (285) | | | | MO, 0.74 mg/kg | |
| March 30 (298) | | | Knott's test +ve[a] ≥100[b] | MO, 1.1 mg/kg | |
| April 13 (312) | | | | MO, 1.1 mg/kg | |
| April 27 (326) | | | | MO, 1.1 mg/kg | |
| April 28 (327) | | | Knott's test +ve[a] | | |
| May 11 (340) | | | | MO, 1.1 mg/kg | |
| May 25 (354) | | | | MO, 1.1 mg/kg | |
| May 27 (356) | SNAP −ve[a] | | Knott's test +ve[a] | | no adult heartworm |
| June 8 (368) | | | | MO, 1.1 mg/kg | |
| June 15 (375) | DIROCHEK −ve[c] | | Knott's test +ve[c] 6530 | | no adult heartworm |
| June 24 (384) | | | | MO, 2.0 mg/kg daily for 7 days | |
| July 30 (420) | | | Knott's test +ve[c] 355 | MO, 2.0 mg/kg daily for 8 days | |
| September 28 (480) | PETCHEK −ve[a] | | Knott's test +ve[c] 1810 | | |
| 2010 | | | | | |
| May 12 (706) | | | | | Microfilariae collected for DNA isolation |

MO = milbemycin oxime (INTERCEPTOR ®);
IVM = ivermectin (IVOMEC ® Injection for cattle, sheep and swine, Merial Inc.);
*Adulticide = IMIMITICIDE ®;
[a] = Main West Animal Hospital (i.e. test carried out in house);
[b] = Idexx Laboratories;
[c] = Animal Health Laboratory, University of Guelph.

f. LOE isolate case 2. Approximately 9000 pooled mf were obtained from a dog from Mechanicsville, Va., that had been treated with INTERCEPTOR® from 2004 to 2008. In May 2008, the dog was heartworm antigen positive and was placed on HEARTGARD® Plus (IVM/PYR) for slow kill treatment. In 2008, the dog was still positive for heartworm antigen and was still microfilaremic. From Dr Blagburn's (Auburn University) in vitro assay: $LD_{95}$ concentration for susceptible mf produced only a 10.5% kill, and 2× $LD_{95}$ produced a 13.6% kill of mf.

g. LOE isolate case 3. Pooled mf were obtained from low responder mf from an in vitro ivermectin susceptibility assay. The dog was a naturally infected client-owned animal, from Monroe, La., selected because it had been on ML heartworm preventative treatment. The veterinarian was convinced that compliance was not an issue. Patient records indicated that proper amounts of product had been provided to the client, based on numbers and weights of target animals in the household. The dog was microfilaremic despite the fact that it had been under ML heartworm prophylaxis.

h. LOE isolate case 4. Pooled mf were obtained from a dog that had the history as described below. This stray dog originated from Haywood County, Tenn., USA, and presented as heartworm antigen positive to a local clinic on Jan. 21, 2011. The dog was neutered on Jan. 26, 2011. On Feb. 1, 2011, doxycycline (200 mg orally twice per day) and prednisone (1 5 mg tablet orally every other day) therapy was initiated and continued for 30 days. On Feb. 2, March 3 and Mar. 4, 2011, an injection of melarsomine dihydrochloride (IMMITICIDE®) (2.5 mg/kg) were given. On Feb. 2, March 3 and Apr. 1, 2011, an oral dose of milbemycin oxime (INTERCEPTOR®) (11.5 mg/tablet) was given. On Apr. 5, 2011, a Knott's test was performed and was positive; ivermectin was administered subcutaneously at a dose of 0.26 mg/kg. On Apr. 11, 2011, Knott's test was again positive; ivermectin was administered subcutaneously at a dose of 0.39 mg/kg. Knott's tests were again performed on both Apr. 19 and 26, 2011 and were both positive. On May 2, 2011, Knott's test was again positive and a blood smear showed microfilariae; ADVANTAGE MULTI® (2.5% imidacloprid, 10% moxidectin) was administered to the dog. On May 5, 2011, a blood smear was positive for microfilariae; at this time, microfilariae were collected. The repeated adulticide treatment led to the assumption they the dog was free of adult parasites. On Jun. 11, 2011, 200 mg of diethylcarbamazine was administered to the dog. No side effects of the treatment were noted. Within 7 days, the blood smear showed no mf. The dog was adopted on Aug. 18, 2011 and moved to Massachusetts.

i. LOE isolate case 5. Pooled mf were obtained from a dog originating from West Monroe, La., USA. This was a veterinarian's dog. The medical history implied compliant use of milbemycin oxime and there were several negative heartworm antigen tests at annual check-ups, until a positive heartworm antigen test and presence of mf in the blood on Sep. 25, 2008. An in vitro microfilaria sensitivity assay was performed (B. Blagburn laboratory, Auburn University, Alabama) on Nov. 19, 2008. The results of the assay indicated drug-resistant organisms. Mosquitoes were fed on infected blood samples from this original dog. L3 larvae were used to infect a second dog. At the time of infection, the second dog had been under treatment with ivermectin. Thereafter, at weekly intervals, the second dog received 1 dose of 3 μg ivermectin/kg, followed by 11 doses of 6 μg ivermectin/kg, followed by 4 doses of 12 μg ivermectin/kg, followed by 8 doses of 24 μg ivermectin/kg (interrupted for one week after the 4th dose). During the entire period of weekly dosing with ivermectin, the dog was remained positive for mf. Microfilariae were collected at 1 and 2 weeks after the last treatment were used in the analysis.

j. LOE isolate case 6. The samples correspond to the second passage of parasite that came from a dog originally from Earle, Ark., USA. The original isolate LOE-6 dog received milbemycin oxime in 2004 and 2005, ivermectin/pyrantel in 2006 and 2007, and ivermectin/praziquantel/pyrantel (IVERHART MAX™) in January 2008 and at the beginning of July 2008. The owner stated that she had been consistent with prophylaxis. This dog tested negative for heartworm antigen at annual check-ups in 2005, 2006 and 2007. This dog was positive for heartworm antigen and microfilaremic at the annual exam on Nov. 4, 2008. Results of the in vitro microfilaria assay (B. Blagburn laboratory, Auburn University, Ala.) on this dog suggested resistance. Dog-LOE-6, was experimentally infected on Nov. 16, 2009 with L3 larvae derived from mosquitoes fed with blood from the first passage. The first passage dog was experimentally infected on Feb. 24, 2009 with L3 larvae derived from mosquitos fed with blood from a naturally infected dog (the original isolate LOE-6 dog).

Example 2

DNA Isolation from Parasites Used in the Studies

Genomic DNA for the individual adult worms was extracted with DNEASY™ kit from Qiagen (Qiagen Inc, Mississauga, Canada). The genomic DNA extraction of individual mf was extracted using QIAAMP® DNA Micro kit from Qiagen. To obtain enough DNA for analysis, the mf DNA was amplified using a REPLI-G® kit from Qiagen which allow amplifying the full genome from a very small amount of DNA. Mf were isolated by filtration through polycarbonate membrane filters from freshly drawn blood.

Example 3

DNA Sequencing, Analysis and Identification of SNPs

The goal was to identify genetic changes (e.g., nucleotide variations) present in LOE heartworm populations that were not present in the susceptible heartworm populations. Nucleotide variations in any of the LOE populations, as compared to a reference genome obtained from the susceptible isolates, would indicate potential SNP markers.

Initially, the genomes from the heartworm populations identified in lettered paragraphs a-h of Example 2 above (susceptible isolates from Missouri, Grand Canary Island, Grenada and Italy; LOE isolates cases 1-4) were sequenced using the HISEQ™2000 system from ILLUMINA®. Table 3 shows the number of reads and the number of bases that were sequenced for each population. Not included in Table 3 is information from heartworm populations identified in paragraphs i and j (resistant isolates from LOE cases 5 and 6).

TABLE 3

Read information on isolates used for whole genome sequencing

| Isolates | Number of reads | Number of bases |
|---|---|---|
| 1 - susceptible | 85,097,000 | 17,019,400,000 |
| 2 - susceptible | 78,242,862 | 15,648,572,400 |
| 3 - susceptible | 80,687,895 | 16,137,579,000 |
| 4 - susceptible | 75,515,617 | 15,103,123,400 |
| 5 - LOE-1 | 82,417,743 | 16,483,548,600 |
| 6 - LOE-2 | 74,261,369 | 14,852,273,800 |
| 7 - LOE-3 | 79,894,844 | 15,978,968,800 |
| 8 - LOE-4 | 75,477,318 | 15,095,463,600 |

The data generated from the ML susceptible samples (susceptible isolates from Missouri, Grand Canary Island, Grenada and Italy) were used to assemble the genome which was then used as the reference genome for the project. All of the individual fragments from the 4 susceptible populations were pooled together. Velvet aligner software (European Bioinformatics Institute) was used to assemble the genome. Reads were filtered by having the adaptor sequences removed/clipped, if found. Reads were trimmed at Q30 length 32 base pairs. A length of 32 base pairs is the Aligner seed default value and the number of reads was consistent with the default value. Table 4 describes the assembly of the reference genome used for the study.

TABLE 4

Information about the *D. immitis* genome assembly

| | |
|---|---|
| Number of contigs | 22 96 |
| 50% of the contigs are longer than | 28 928 bp |
| Length of longest contig | 250 211 bp |
| Total bases in contigs | 94 611 006 (94 Mb) |
| Number of contigs >1 kb | 6654 |
| Total bases in contigs >1 kb | 90 045 376 bp (90 Mb) |

Once the reference heartworm genome was obtained from sequences of the susceptible isolates/populations, then the genomes from the LOE populations were compared to the reference genome, to identify differences and possible SNPs. As part of this analysis, genetic loci containing the potential SNPs were shown not to be significantly different between the individual susceptible populations (i.e., between the susceptible isolates from Missouri, Grand Canary Island, Grenada and Italy), as well as not to be significantly different between the individual LOE populations (LOE 1-4), but were significantly different between the susceptible populations and the LOE populations. To perform this analysis, the software program called PoPoolation2 (Kofler et al. Bioinformatics 27: 3435-3436, 2011) was used. The program required the use of other programs, such as Perl, R, bwa, and Samtools. First, a synchronized file was generated, which contained the nucleotide frequencies for every population at every base in the reference genome, after filtering for base quality, in a concise format. The synchronized file generated with the PoPoolation2 program contained detailed nucleotide count information on loci for each of the populations. P-values were generated with Fisher's exact test for all the possible comparisons between populations. To identify loci associated with ML resistance, p-values needed to be simultaneously not statistically significant (>0.05) within all susceptible samples and within all the LOE samples, and statistically significant (<0.05) between all susceptible versus all LOE samples. Three hundred thirty eight loci met these criteria, including 12 that had a p-value of $10^{-5}$. Flanking regions of 1000 bp including each locus that was statistically different between the susceptible and LOE samples were analyzed by Blast (BlastN and BlastX) in NCBI and in the Broad Institute filarial genome database to remove loci located in mitochondrial, *Wolbachia* or *C. lupus famillaris* DNA. Loci located in reads with very high polymorphism (>2 nucleotides and/or indels) or low coverage (<10×) were removed from further analysis. Nucleotide counts for each locus of interest were analyzed individually for the pooled populations to ensure that the increase or decrease in nucleotide frequency was in the same direction for all the susceptible samples or for all the LOE samples. The loci that best met the criteria were retained for further genotype analysis on individual parasites to assess actual allele frequencies in populations that had been characterized in terms of ML response.

From these analyses, 186 loci were found to be significantly different between the susceptible and LOE samples. As this approach was based on reads and nucleotide frequencies of pooled samples, these loci were further studied (SNP genotyping) using individual (not pooled) populations. For this purpose, SEQUENOM® SNP frequency analysis was used. Table 5, below, shows the origins of the DNA used in this analysis.

TABLE 5

Description of isolates used for SEQUENOM ® analysis

| | State and/or country of origin | # Individual adult worm | # Individual microfilaria | From # dogs |
|---|---|---|---|---|
| Susceptible samples = 181 isolates | | | | |
| Sus1-Missouri | Missouri isolate, USA | | 49 | 1 |
| Sus2-Missouri | Missouri isolate, USA | | 45 | 1 |
| Grand Canary | Grand Canary, Spain | 71 | | 11 |
| Grenada | Grenada, WI | 10 | | 2 |
| Italy | Northern Italy | 6 | | |
| Low responder samples = 244 Isolates | | | | |
| LOE-1 | New Orleans, LA, USA, moved to Ontario, Canada | | 56 | 1 |
| LOE-2 | Mechanicsville, VA, USA | | 35 | 1 |
| LOE-3 | Monroe, LA, USA | | 51 | 1 |
| LOE-5 | West Monroe, LA, USA | | 54 | 1 |
| LOE-6 | Earle, AR, USA | | 48 | 1 |

SEQUENOM® analysis is based on multiplex PCR and MALDI-TOF mass spectrometry. The SEQUENOM® analysis was used to evaluate the 186 loci using 425 individual samples (5 panels with 36-38 SNPs in each panel). Primer design for each SNP marker was based on a requirement that elongation primers be located in a non-polymorphic region 15 base pairs before or after the SNP of interest. All the genome calls were performed blinded (i.e., the sample origin and dog treatment history was not known during the analysis). A total of 79050 genotypes were analyzed. From the 186 potential loci, 109 were observed to have technical advantages to predict for ML loss of efficacy. The susceptible population carried more than 90% of the wild-type genotype while the LOE population had a significant lower genotype frequency of the wild-type genotype. These 109 loci are disclosed herein as SEQ ID NOs: 1-109.

Example 4

Additional SNPs from Confirmed Resistant Organisms

LOE samples, as described in Example 1, were presumed to be resistant to MLs because of the history of treatment of the dogs with MLs and the continued presence of heartworm organisms. However, despite the history of treatment, an alternative explanation to true ML-resistance of the parasites is owner non-compliance of ML treatment. Therefore, a study was performed under controlled ML treatment conditions, to eliminate the possibility of owner non-compliance in ML treatment, as a possible reason for presence of heartworm organisms in dogs.

Heartworm organisms used in the efficacy studies were derived from one identified as Jd2009 from Earle, Ark., USA. Jd2009 received monthly MO in 2004 and 2005, IVM/pyrantel in 2006 and 2007, and IVM/praziquantel/pyrantel in January 2008 until early July 2008. Jd2009 tested negative for HW antigen in 2005, 2006, and 2007. This dog was heartworm antigen positive and microfilaremic on Apr. 11, 2008 despite a history of compliance with HW preventatives. Mf were obtained from the dog at this time with the consent of the owner and were sent to Auburn University, where the mf were examined for sensitivity to IVM in an in vitro concentration-response assay measuring migration (Blagburn, B., American Heartworm Society-13th Triennial State of the Heartworm Symposium, 2010). These mf were significantly less sensitive to IVM than mf obtained from a dog infected with a laboratory strain of *D. immitis* that was fully susceptible to the drug. The mf were used at Auburn University to infect mosquitoes to produce L3 that were used to infect dog Jd2009-1, which developed a patent infection. Mf from this dog were shown to be as resistant to ML as mf from Jd2009 in the in vitro migration assay.

L3s derived from mf harvested from Jd2009-1 were used at Auburn University to infect a second dog, Jd2009-2 and the dog was treated monthly with HEARTGARD PLUS® (0.006-0.013 mg/kg IVM) 9 consecutive times. Adult worms were recovered indicating that the Jd2009-2 isolate was resistant to IVM prophylaxis. In a second study, dogs were challenged with Jd2009-2 L3 on day 0 and treated monthly for 5 consecutive months with HEARTGARD PLUS® (0.007-0.009 mg/kg IVM; Study 1b). At necropsy on day 188, efficacy was 71.3%, confirming resistance to IVM prophylaxis in the Jd2009-2 isolate.

In another study, dogs were challenged with L3 on day 180 after PROHEART6® injection. At necropsy on day 150 after infection, efficacy was 21.6%, indicating that the Jd2009-2 was also resistant to the PROHEART6® long acting formulation of MOX, which has a claim for 100% protection for 180 days after treatment.

In another study, the confirmed IVM-resistant isolate Jd2009-2 was used to determine whether the resistance extended to other ML heartworm preventatives. None of the other ML heartworm preventatives (MOX, MO and SEL), given as monthly chemoprophylaxis as recommended, was fully effective, i.e., at least one dog in groups of four to six dogs on these heartworm preventatives became infected with *D. immitis* following treatment with each of these MLs used as recommended.

DNA from individual organisms from two Jd2009 isolates were used. DNA from individuals from one group, called RES-1, came from 4 dogs from the PROHEART6® study, described above. DNA from individuals from another group, called RES-2, came from 6 dogs from the HEARTGARD PLUS® study, described above.

DNA was isolated from 115 adult worms and 79 mf from the RES-1 and RES-2 populations, as described in Example 2, and were analyzed using SEQUENOM® SNP frequency analysis, as described in Example 3. From this analysis, 18 additional loci (out of the initial 186 loci) were significantly different between the susceptible and RES samples. These loci are disclosed herein as SEQ ID NOs: 110-127.

While example compositions, methods, and so on have been illustrated by description, and while the descriptions are in considerable detail, it is not the intention of the applicants to restrict or in any way limit the scope of the application. It is, of course, not possible to describe every conceivable combination of components or methodologies for purposes of describing the compositions, methods, and so on described herein. Additional advantages and modifications will readily appear to those skilled in the art. Therefore, the disclosure is not limited to the specific details, the representative apparatus, and illustrative examples shown and described. Thus, this application is intended to embrace alterations, modifications, and variations that fall within the scope of the application. Furthermore, the preceding description is not meant to limit the scope of the invention. Rather, the scope of the invention is to be determined by the appended claims and their equivalents.

What is claimed is:

1. An isolated nucleic acid molecule comprising 25-300 nucleotides of SEQ ID NO: 118, or a reverse complement thereof; wherein the isolated nucleic acid molecule includes a polymorphic site at position 151 which confers resistance to a macrocyclic lactone, wherein position 151 is G; and wherein the isolated nucleic acid molecule further includes a detectable label selected from the group consisting of radioactive, enzymatic, and fluorescent labels.

2. The isolated nucleic acid molecule of claim 1, wherein the nucleic acid molecule has at least 35 nucleotides of SEQ ID NO: 118, or a reverse complement thereof;
wherein the isolated nucleic acid molecule includes a polymorphic site that confers resistance to a macrocyclic lactone.

3. The isolated nucleic acid molecule of claim 1, wherein the nucleic acid molecule has at least 50 nucleotides of SEQ ID NO: 118, or a reverse complement thereof;
wherein the isolated nucleic acid molecule includes a polymorphic site that confers resistance to a macrocyclic lactone.

4. The isolated nucleic acid molecule of claim 1, wherein the nucleic acid molecule has at least 100 nucleotides of SEQ ID NO: 118, or a reverse complement thereof;
wherein the isolated nucleic acid molecule includes a polymorphic site that confers resistance to a macrocyclic lactone.

5. The isolated nucleic acid molecule of claim 1, wherein the nucleic acid molecule has at least 45 nucleotides of SEQ ID NO: 118, or a reverse complement thereof.

6. The isolated nucleic acid molecule of claim 1, wherein the nucleic acid molecule has at least 30 nucleotides of SEQ ID NO: 118, or a reverse complement thereof.

7. The isolated nucleic acid molecule of claim 1, wherein the nucleic acid molecule has at least 40 nucleotides of SEQ ID NO: 118, or a reverse complement thereof.

8. A kit for determining a genotype of a *Dirofilaria* spp. nematode, the kit comprising at least a first isolated nucleic acid molecule comprising 25-300 nucleotides of SEQ ID NO: 118, or a reverse complement thereof;
wherein the isolated nucleic acid molecule includes a polymorphic site at position 151 which confers resistance to a macrocyclic lactone, wherein position 151 is G; and
wherein the oligonucleotide further includes a detectable label selected from the group consisting of radioactive, enzymatic, and fluorescent labels.

9. The kit of claim 8, wherein the isolated nucleic acid molecule is a probe, a primer or an aptamer.

10. The kit of claim 8, wherein the kit further comprises one or more of reagents, buffers, packaging materials, and instructions for determining the genotype of the nematode by DNA sequencing, hybridization-based methods including with allele specific oligonucleotides, microarray analysis, enzyme-based methods, single strand conformational polymorphism (SSCP), high resolution melt (HRM) or approaches based on PCR, RT-PCR, or qRT-PCR.

11. The kit of claim 8, further comprising at least a second isolated nucleic acid molecule having a length of at least 10 nucleotides of a sequence selected from the group consisting of SEQ ID NOs: 1-113, 115-117, and 119-127, or a reverse complement thereof;
wherein the at least a second isolated nucleic acid molecule includes a disclosed polymorphic site that correlates with resistance to a macrocyclic lactone; and
wherein the at least a second isolated nucleic acid molecule further includes a detectable label.

* * * * *